(12) United States Patent
Kozlowski et al.

(10) Patent No.: US 10,220,020 B2
(45) Date of Patent: Mar. 5, 2019

(54) POLYMER-DES-ETHYL SUNITINIB CONJUGATES

(75) Inventors: Antoni Kozlowski, Huntsville, AL (US); Sean M. Culbertson, Gurley, AL (US); Xiaoming Shen, Millbrae, CA (US); Samuel P. Mcmanus, Guntersville, AL (US); Mark A. Wilson, Burlingame, CA (US)

(73) Assignee: NEKTAR THERAPEUTICS, San Francisco, CA (US)

( * ) Notice: Subject to any disclaimer, the term of this patent is extended or adjusted under 35 U.S.C. 154(b) by 868 days.

(21) Appl. No.: 13/995,819

(22) PCT Filed: Dec. 23, 2011

(86) PCT No.: PCT/US2011/067240
§ 371 (c)(1),
(2), (4) Date: Oct. 10, 2013

(87) PCT Pub. No.: WO2012/088522
PCT Pub. Date: Jun. 28, 2012

(65) Prior Publication Data
US 2014/0039030 A1  Feb. 6, 2014

Related U.S. Application Data

(60) Provisional application No. 61/426,893, filed on Dec. 23, 2010.

(51) Int. Cl.
*A61K 47/60* (2017.01)
*A61K 31/404* (2006.01)

(52) U.S. Cl.
CPC ............ *A61K 31/404* (2013.01); *A61K 47/60* (2017.08)

(58) Field of Classification Search
CPC ............................ A61K 31/404; A61K 47/60
See application file for complete search history.

(56) References Cited

U.S. PATENT DOCUMENTS

| | | | |
|---|---|---|---|
| 4,810,646 A | 3/1989 | Jamas et al. |
| 4,992,540 A | 2/1991 | Jamas et al. |
| 5,028,703 A | 7/1991 | Jamas et al. |
| 5,607,677 A | 3/1997 | Jamas et al. |
| 5,741,495 A | 4/1998 | Jamas et al. |
| 5,932,462 A | 8/1999 | Harris et al. |
| 6,573,293 B2 | 6/2003 | Tang et al. |
| 7,026,440 B2 | 4/2006 | Bentley et al. |
| 7,053,144 B1 | 5/2006 | Immel |
| 7,125,905 B2 | 10/2006 | Tang et al. |
| 7,211,600 B2 | 5/2007 | Lipson et al. |
| 7,214,700 B2 | 5/2007 | Wei et al. |
| 7,744,861 B2 | 6/2010 | Zhao et al. |
| 9,827,326 B2 | 11/2017 | Culbertson et al. |
| 2005/0009988 A1 | 1/2005 | Harris et al. |
| 2005/0079155 A1 | 4/2005 | Marshall |
| 2005/0281781 A1 | 12/2005 | Ostroff |
| 2006/0293499 A1 | 12/2006 | Bentley et al. |
| 2008/0044438 A1 | 2/2008 | Ostroff et al. |
| 2014/0331425 A1 | 11/2014 | Baker |

FOREIGN PATENT DOCUMENTS

| | | |
|---|---|---|
| WO | WO 01/60814 A2 | 8/2001 |
| WO | WO 01/90068 | 11/2001 |
| WO | WO 03/35009 | 5/2003 |
| WO | WO 2005/028539 A2 | 3/2005 |
| WO | WO 2005/107815 | 11/2005 |
| WO | WO 2005/108463 | 11/2005 |
| WO | WO 2007/098466 | 8/2007 |
| WO | WO 2008/082669 A2 | 7/2008 |
| WO | WO 2009/073154 A1 | 6/2009 |
| WO | WO 2009/099670 A2 | 8/2009 |
| WO | WO 2009/126333 A1 | 10/2009 |
| WO | WO 2009/141823 A2 | 11/2009 |
| WO | WO 2010/019233 | 2/2010 |
| WO | WO 2010/091187 A2 | 8/2010 |
| WO | WO 2010/120387 | 10/2010 |
| WO | WO 2010/120388 A1 | 10/2010 |

OTHER PUBLICATIONS

Bacchi, et al., "Novel Synthetic Polyamines Are Effective in the Treatment of Experimental Microsporidiosis, an Opportunistic AIDS-Associated Infection", Antimicrobial Agents and Chemotherapy, vol. 46, No. 1, pp. 55-61, (2002).
Brinkley, "A Brief Survey of Methods for Preparing Protein Conjugates with Dyes, Haptens, and Cross-Linking Reagents", Bioconjugate Chem., vol. 3, pp. 2-13, (1992).
Blanche, et al., "Synthesis of potential prodrug systems for reductive activation. Prodrugs for anti-angiogenic isoflavones and VEGF receptor tyrosine kinase inhibitor oxindoles", Tetrahedron, vol. 65, pp. 4894-4903, (2009).
Greenwald, et al., "Poly(ethylene glycol) Conjugated Drugs and Prodrugs: A Comprehensive Review", Critical Reviews in Therapeutic Drug Carrier Systems, vol. 17, No. 2, pp. 101-161, (2000).
Pasut, et al., "Protein, peptide and non-peptide drug PEGylation for therapeutic application", Expert Opin. Ther. Patents, vol. 14, No. 6, pp. 859-894, (2004).
Rygaard, et al., "Heterotransplantation of a Human Malignant Tumour to "Nude" Mice", Acta. Path. Microbiol. Scand., vol. 77, pp. 758-760, (1969).
Sun, et al., "Synthesis and Biological Evaluations of 3-Substituted Indolin-2-ones: A Novel Class of Tyrosine Kinase Inhibitors That Exhibit Selectivity toward Particular Receptor Tyrosine Kinases", J. Med. Chem., vol. 41, pp. 2588-2603, (1998).
Voller, et al., "Enzyme-Linked Immunosorbent Assay", Am. Soc. of Microbio., Man. of Clin. Immun., $2^{nd}$ ed., pp. 359-371, (1980).

(Continued)

*Primary Examiner* — Theodore R. West
(74) *Attorney, Agent, or Firm* — Jacqueline F. Mahoney

(57) ABSTRACT

The invention relates to (among other things) polymer-des-ethyl sunitinib conjugates and related compounds. A compound of the invention, when administered by any of a number of administration routes, exhibits advantages over des-ethyl sunitinib in unconjugated form.

21 Claims, 2 Drawing Sheets

(56) References Cited

OTHER PUBLICATIONS

PCT International Search Report and Written Opinion corresponding PCT Application No. PCT/US2011/067240 dated May 30, 2012.
PCT International Preliminary Report on Patentability corresponding PCT Application No. PCT/US2011/067240 dated Jul. 4, 2013.
Enzon Pharmaceuticals, Macromolecular Engineering Technologies, 16 pages, (2004).
NEKTAR™—Transforming Therapeutics, Nektar Molecule Engineering: Polyethylene Glycol and Derivatives for Advanced PEGylation, 24 pages, Catalog—2003, (Jul. 2003).
NEKTAR™—Transforming Therapeutics, Nektar Advanced PEGylation: Polyethylene Glycol and Derivatives for Advanced PEGylation, 27 pages, Catalog—2004, (Jul. 2004).
NEKTAR™—Transforming Therapeutics, Nektar Advanced PEGylation: Polyethylene Glycol and Derivatives for Advanced PEGylation, 33 pages, (Catalog 2005-2006).
NOF Corporation, PEG Derivatives, Phospholipid and Drug Delivery Materials for Pharmaceuticals, 46 pages, Catalogue 2003-$1^{st}$, (Jan. 2003).
NOF Corporation, PEG Derivatives, Phospholipid and Drug Delivery Materials for Pharmaceuticals, 27 pages, Catalogue 2003-$2^{nd}$, (Mar. 2004).
NOF Corporation, PEG Derivatives, Phospholipids and Drug Delivery Materials for Pharmaceutical Products and Formulations, 60 pages, Catalogue Ver. 8, (Apr. 2006).
POLYPURE Products, PEG amines; PEG acids and amino acids; PEG thiols and disulfides; BIOTINS, 5 pages, (Apr. 2004).
POLYPURE Products, PEG amines; PEG acids and amino acids; PEG thiols and disulfides; BIOTINS, 5 pages, (Apr. 2005).
QUANTA Biodesign, Labeling, Derivatization and Crosslinking Reagents for Biological and Related Materials with dPEG™, 38 pages, (Mar. 12, 2004).
Quanta Biodesign, Labeling, Modification and Crosslinking Reagents incorporating our unique monodispersed dPEG™ Technology, 31 pages, (Nov. 5, 2004).
Quanta Biodesign, Ltd., Leading innovator, producer and provider of monodisperse discrete PEG™ (dPEG™) derivatives, (Product Catalog), 26 pages, (Updated: Jul. 18, 2005).
Quanta Biodesign, Ltd., Leading innovator, producer and provider of monodisperse discrete PEG™ (dPEG™) derivatives, (Product Catalog), 26 pages, (Updated: Nov. 17, 2005).
Shearwater Polymers, Inc., Polyethylene Glycol Derivatives, 50 pages, Catalog—(Mar. 1995).
Shearwater Polymers, Inc., Polyethylene Glycol Derivatives, 55 pages, Catalog 1997-1998, (Jul. 1997).
Shearwater Polymers, Inc., Polyethylene Glycol and Derivatives: Functionalized Biocompatible Polymers for Research and Pharmaceuticals, 50 pages, Catalog—(Jan. 2000).
Shearwater Corporation, Polyethylene Glycol and Derivatives for Biomedical Applications, 20 pages, Catalog—(Jul. 2001).
English Translation of Notice of Reasons for Rejection in Japanese Patent Application No. 2013-546457 dated Jul. 30, 2015.
International Search Report and Written Opinion in PCT Application No. PCT/US2011/067259 dated May 30, 2012.
International Preliminary Report on Patentability in PCT Application No. PCT/US2011/067259 dated Jul. 4, 2013.
Communication in European Patent Application No. 11 809 055.4 dated Jul. 11, 2016.
Communication in European Patent Application No. 11 811 620.1 dated Jul. 11, 2016.
English Translation of Japanese Notice of Reason for Rejection in Japanese Patent Application No. 2013-546460 dated Aug. 28, 2015.
English Translation of Japanese Notice of Final Rejection in Japanese Patent Application No. 2013-546460 dated Mar. 24, 2016.
Kollmannsberger et al., "Sunitinib therapy for metastatic renal cell carcinoma: recommendations for management of side effects", CUAJ, vol. 1, Issue 2 Suppl., pp. S41-S54, (Jun. 2007).
English Translation of the Notice of Final Rejection corresponding to Japanese Patent Application No. 2013-546457 dated Apr. 12, 2016.

POLYMER-DES-ETHYL SUNITINIB CONJUGATES

CROSS-REFERENCE TO RELATED APPLICATIONS

This application is a 35 U.S.C. § 371 application of International Application No. PCT/US2011/067240, filed Dec. 23, 2011, designating the United States, which claims the benefit of priority under 35 U.S.C. § 119(e) to U.S. Provisional Patent Application Ser. No. 61/426,893 filed Dec. 23, 2010, the disclosures of which are incorporated herein by reference in their entireties.

FIELD OF THE INVENTION

This invention comprises (among other things) chemically modified forms of the receptor tyrosine kinase (RTK) inhibitor, des-ethyl sunitinib, which forms possess certain advantages over des-ethyl sunitinib lacking the chemical modification. The chemically modified forms of des-ethyl sunitinib described herein relate to and/or have application(s) in (among others) the fields of drug discovery, pharmacotherapy, physiology, organic chemistry and polymer chemistry.

BACKGROUND OF THE INVENTION

Protein kinases ("PKs") are enzymes that catalyze the phosphorylation of hydroxy groups on tyrosine, serine and threonine residues within proteins. Phosphorylation of these hydroxy groups is required for the growth, differentiation and proliferation of cells. Thus, virtually all aspects of the cell life cycle depend on normal PK activity. In view of the criticality normal PK activity has on healthy cell functioning, it is perhaps not surprising that abnormal PK activity has been related to a host of disorders, ranging from relatively non-life threatening diseases such as psoriasis to extremely virulent diseases such as glioblastoma (brain cancer).

Among other categorizations, PKs can be divided into two classes, the cytoplasmic protein tyrosine kinases (PTKs) and the transmembrane receptor tyrosine kinases (RTKs). Briefly, the RTKs comprise a family of transmembrane receptors with diverse biological activity. The HER (human epidermal growth factor receptor) subfamily of RTKs includes EGFR (epithelial growth factor receptor), HER2, HER3 and HER4. These RTKs consist of an extracellular glycosylated ligand binding domain, a transmembrane domain and an intracellular cytoplasmic catalytic domain that can phosphorylate tyrosine residues on proteins.

Another RTK subfamily consists of insulin receptor (IR), insulin-like growth factor I receptor (IGF-1R) and insulin receptor related receptor (IRR). IR and IGF-1R interact with insulin, IGF-I and IGF-II to form a heterotetramer of two entirely extracellular glycosylated alpha subunits and two beta subunits which cross the cell membrane and which contain the tyrosine kinase domain.

A third RTK subfamily is referred to as the "platelet derived growth factor receptor" ("PDGF-R") group, which includes PDGF-R-α, PDGF-R-β, CSFI-R, c-kit and c-fms. These receptors consist of glycosylated extracellular domains composed of variable numbers of immunoglobin-like loops and an intracellular domain wherein the tyrosine kinase domain is interrupted by unrelated amino acid sequences.

Another group, which, because of its similarity to the PDGF-R subfamily (and is sometimes subsumed into the PDGF-R subfamily) is the fetus liver kinase ("a") receptor subfamily. This group is believed to be made up of kinase insert domain-receptor fetal liver kinase-1 (KDR/FLK-1, VEGF-R2), flk-1R, flk-4 and fms-like tyrosine kinase 1 (flt-1).

Still another member of the tyrosine kinase growth factor receptor family is the vascular endothelial growth factor ("VEGF") receptor subgroup. VEGF is a dimeric glycoprotein similar to PDGF but has different biological functions and target cell specificity in vivo. In particular, VEGF is presently thought to play an essential role is vasculogenesis and angiogenesis.

Sunitinib is a multi-targeted RTK marketed by Pfizer Inc. under the brand name SUTENT®. Chemically, sunitinib's systematic name is "N-(2-diethylaminoethyl)-5-[(Z)-(5-fluoro-2-oxo-1H-indol-3-ylidene)methyl]-2,4-dimethyl-1H-pyrrole-3-carboxamide" and its chemical formula is provided below.

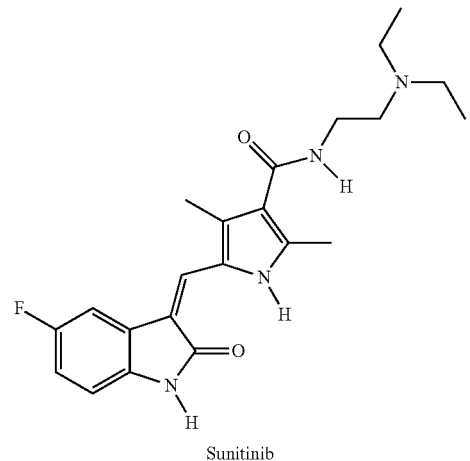 [SMILES: CCN(CC)CCNC(=O)c1c(C)[nH]c(/C=C2\C(=O)Nc3ccc(F)cc32)c1C]

Sunitinib

In vivo, sunitinib inhibits cellular signaling by targeting multiple RTKs, including (VEGFRs) and PDGF-Rs. Both of PDGR-Rs and VEGFRs play a role in tumor proliferation and angiogenesis, and sunitinib's ability to inhibit these targets leads to cancer cell death and reduced tumor vascularization, thereby resulting in tumor shrinkage. Sunitinib also inhibits other RTKs, such as KIT, RET, CSF-1R and flt3, thereby potentially making it clinically useful in the treatment of patients suffering from other cancers.

Also in vivo, sunitinib is metabolized to form a des-ethyl of sunitinib, which is roughly equipotent as sunitinib and has the following structure:

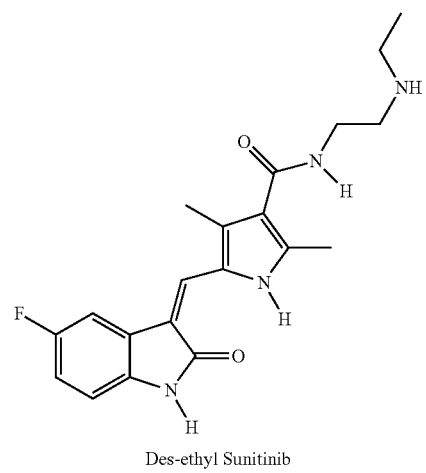 [SMILES: CCNCCNC(=O)c1c(C)[nH]c(/C=C2\C(=O)Nc3ccc(F)cc32)c1C]

Des-ethyl Sunitinib

Treatment with sunitinib (which results in, among other things, the equipotent metabolite des-ethyl sunitinib), however, is not without drawbacks, including hand-foot syndrome, stomatitis, and other toxicities.

Therefore, a need exists to provide compounds that can exert the same pharmacology sunitinib has in vivo, yet has an improved side effect profile. The present invention seeks to address this and/or other needs.

SUMMARY OF THE INVENTION

In one or more embodiments of the invention, a compound is provided, the compound comprising a des-ethyl sunitinib residue covalently attached via a releasable linkage-containing spacer moiety to a water-soluble, non-peptidic polymer.

In one or more embodiments of the invention, a compound is provided, the compound having the following structure:

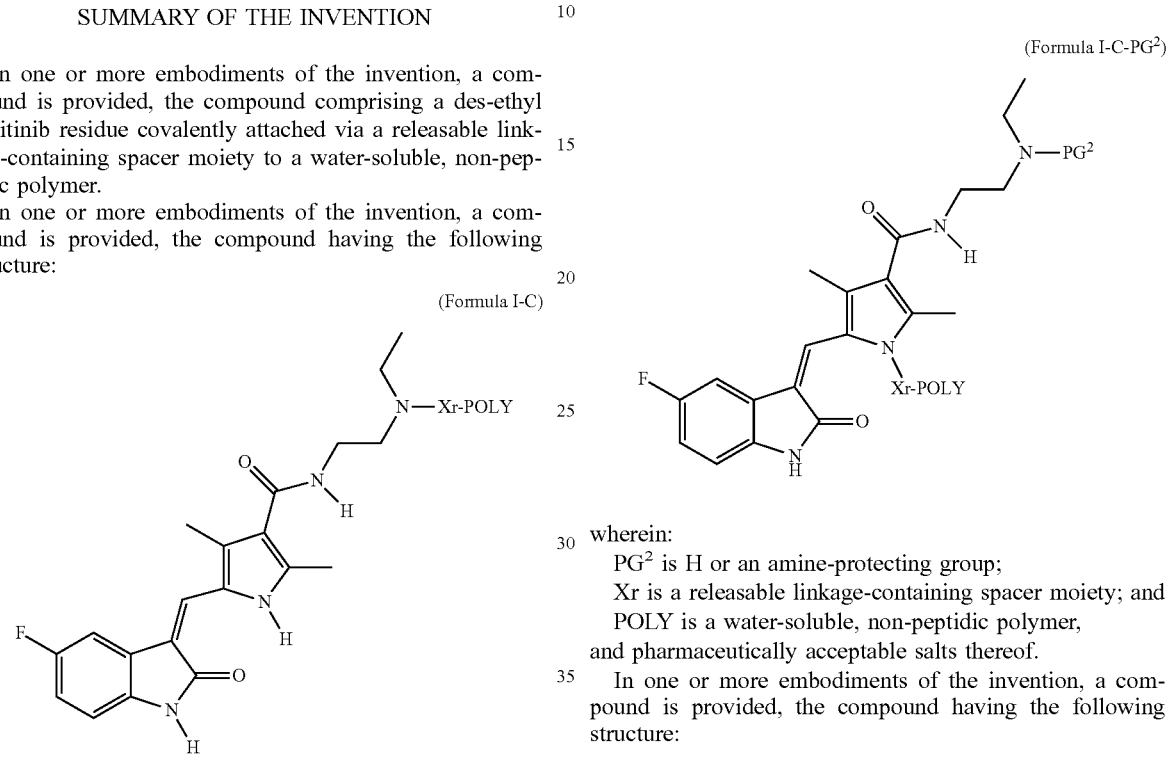

(Formula I-C)

wherein:
Xr is a releasable linkage-containing spacer moiety; and
POLY is a water-soluble, non-peptidic polymer,
and pharmaceutically acceptable salts thereof.

In one or more embodiments of the invention, a compound is provided, the compound having the following structure:

(Formula I-C-PG¹)

wherein:
PG¹ is H or an amine-protecting group;
Xr is a releasable linkage-containing spacer moiety; and
POLY is a water-soluble, non-peptidic polymer,
and pharmaceutically acceptable salts thereof.

In one or more embodiments of the invention, a compound is provided, the compound having the following structure:

(Formula I-C-PG²)

wherein:
PG² is H or an amine-protecting group;
Xr is a releasable linkage-containing spacer moiety; and
POLY is a water-soluble, non-peptidic polymer,
and pharmaceutically acceptable salts thereof.

In one or more embodiments of the invention, a compound is provided, the compound having the following structure:

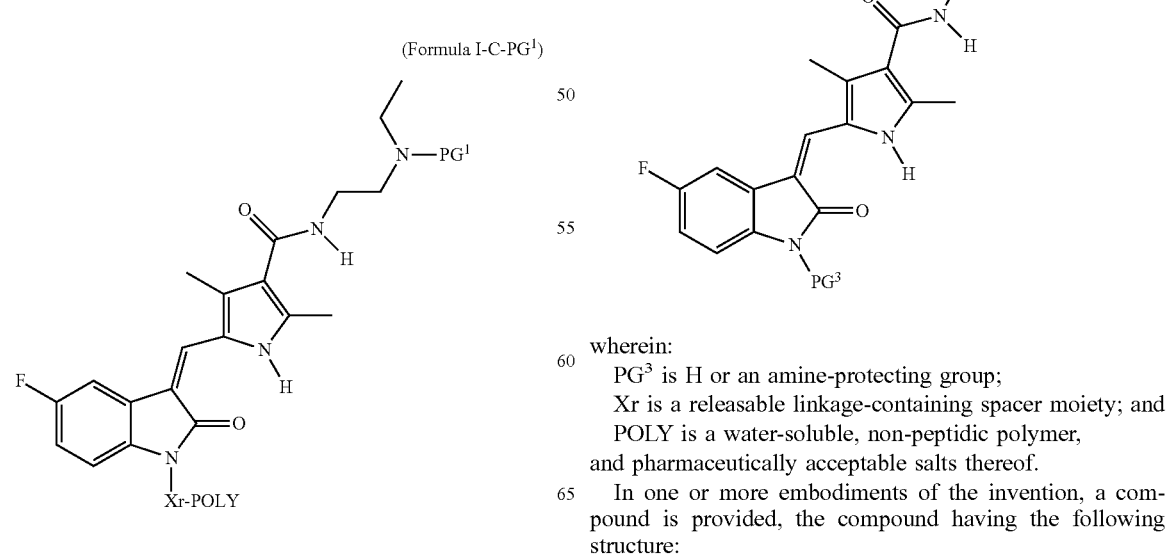

(Formula I-C-PG³)

wherein:
PG³ is H or an amine-protecting group;
Xr is a releasable linkage-containing spacer moiety; and
POLY is a water-soluble, non-peptidic polymer,
and pharmaceutically acceptable salts thereof.

In one or more embodiments of the invention, a compound is provided, the compound having the following structure:

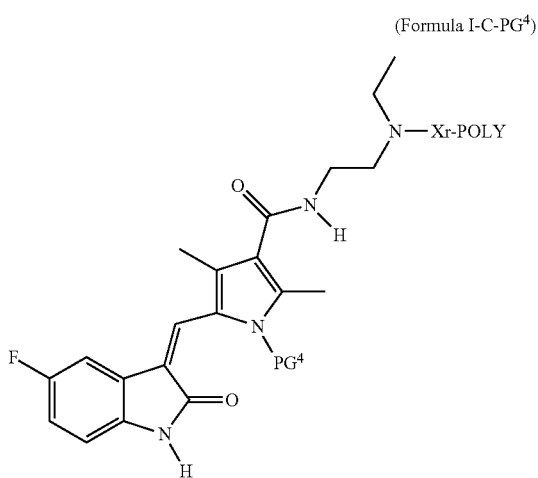

(Formula I-C-PG⁴)

wherein:
PG⁴ is H or an amine-protecting group;
Xr is a releasable linkage-containing spacer moiety; and
POLY is a water-soluble, non-peptidic polymer,
and pharmaceutically acceptable salts thereof.

In one or more embodiments of the invention, a compound is provided, the compound having the following structure:

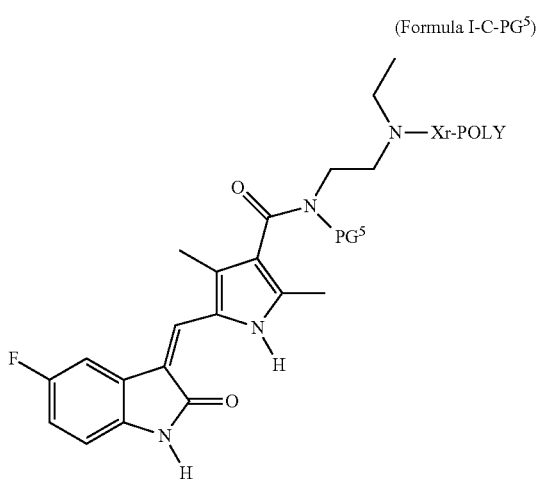

(Formula I-C-PG⁵)

wherein:
PG⁵ is H or an amine-protecting group;
Xr is a releasable linkage-containing spacer moiety; and
POLY is a water-soluble, non-peptidic polymer,
and pharmaceutically acceptable salts thereof.

In one or more embodiments of the invention, a composition is provided, the composition comprising (i) a compound comprising a des-ethyl sunitinib residue covalently attached via a releasable linkage-containing spacer moiety to a water-soluble, non-peptidic polymer, and, optionally, (ii) a pharmaceutically acceptable excipient.

In one or more embodiments of the invention, a dosage form is provided, the dosage form comprising a compound as described herein, wherein the compound is present in a dosage form.

In one or more embodiments of the invention, a method is provided, the method comprising covalently attaching a water-soluble, non-peptidic polymer to des-ethyl sunitinib.

In one or more embodiments of the invention, a method is provided, the method comprising administering a compound as described herein to a mammal in need thereof.

Additional embodiments of the present conjugates, compositions, methods, and the like will be apparent from the following description, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims.

DETAILED DESCRIPTION OF THE INVENTION

Figure 1:
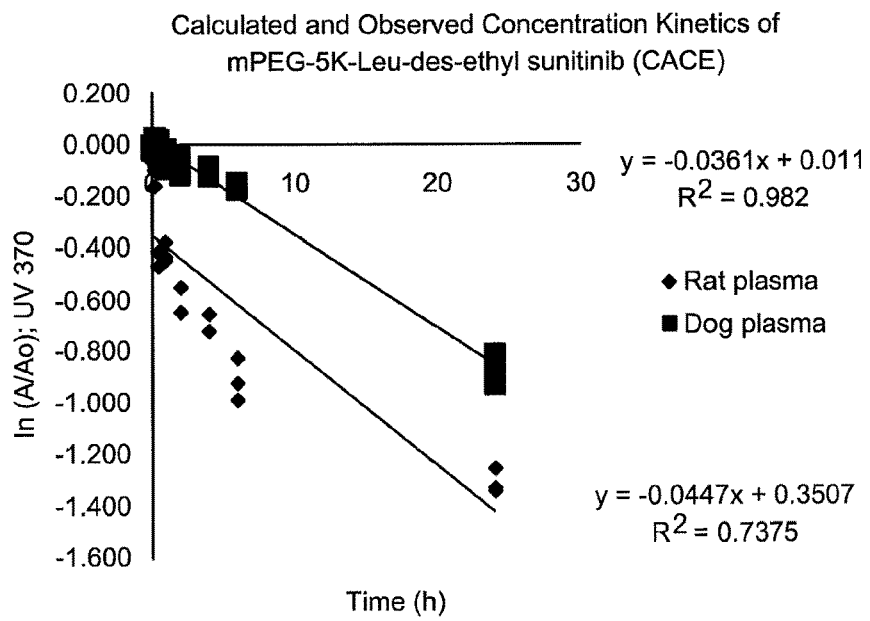
FIG. 1 is a plot of the calculated and observed concentration kinetics of a conjugate of the invention [mPEG-5K-Leu-des-ethyl sunitinib (CACE)], as more fully described in Example 7.

As used in this specification, the singular forms "a," "an," and "the" include plural referents unless the context clearly dictates otherwise.

In describing and claiming the present invention, the following terminology will be used in accordance with the definitions described below.

"Water soluble, non-peptidic polymer" indicates a polymer that is at least 35% (by weight) soluble, preferably greater than 70% (by weight), and more preferably greater than 95% (by weight) soluble, in water at room temperature. Typically, an unfiltered aqueous preparation of a "water-soluble" polymer transmits at least 75%, more preferably at least 95%, of the amount of light transmitted by the same solution after filtering. It is most preferred, however, that the water-soluble polymer is at least 95% (by weight) soluble in water or completely soluble in water. With respect to being "non-peptidic," a polymer is non-peptidic when it has less than 35% (by weight) of amino acid residues.

The terms "monomer," "monomeric subunit" and "monomeric unit" are used interchangeably herein and refer to one of the basic structural units of a polymer. In the case of a homo-polymer (or homopolymer), a single repeating structural unit forms the polymer. In the case of a co-polymer, two or more structural units are repeated—either in a pattern or randomly—to form the polymer. Preferred polymers used in connection with present the invention are homo-polymers. The water-soluble, non-peptidic polymer comprises one or more monomers serially attached to form a chain of monomers. The polymer can be formed from a single monomer type (i.e., is homo-polymeric) or two or three monomer types (i.e., is co- or tri-polymeric).

A "polymer" is a molecule possessing from about 2 to about 2000 or more monomers. Specific polymers for use in the invention include those having a variety of geometries such as linear, branched, or forked, to be described in greater detail below.

"PEG" or "polyethylene glycol," as used herein, is meant to encompass any water-soluble poly(ethylene oxide). Unless otherwise indicated, a "PEG polymer" or any polyethylene glycol is one in which substantially all (preferably all) monomeric subunits are ethylene oxide subunits, though, the polymer may contain distinct end capping moieties or functional groups, e.g., for conjugation. PEG polymers for use in the present invention will comprise one of the two following structures: "—$(CH_2CH_2O)_n$—" or "—$(CH_2CH_2O)_{n-1}CH_2CH_2$—," depending upon whether or not the terminal oxygen(s) has been displaced, e.g., during a synthetic transformation. As stated above, for the PEG polymers, the variable (n) ranges from about 2 to 2000, and the terminal groups and architecture of the overall PEG can vary. When PEG further comprises a functional group, A, for linking to, e.g., a small molecule drug, the functional group when covalently attached to a PEG polymer does not result in formation of an oxygen-oxygen bond (—O—O—, a peroxide linkage).

The terms "end-capped" or "terminally capped" are interchangeably used herein to refer to a terminal or endpoint of a polymer having an end-capping moiety. Typically, although not necessarily, the end-capping moiety comprises a hydroxy or $C_{1-20}$ alkoxy group. Thus, examples of end-capping moieties include alkoxy (e.g., methoxy, ethoxy and benzyloxy), as well as aryl, heteroaryl, cyclo, heterocyclo, and the like. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) of interest to which the polymer is coupled, can be determined by using a suitable detector. Such labels include, without limitation, fluorescers, chemiluminescers, moieties used in enzyme labeling, colorimetric moieties (e.g., dyes), metal ions, radioactive moieties, and the like. Suitable detectors include photometers, films, spectrometers, and the like. In addition, the end-capping group may contain a targeting moiety.

The term "targeting moiety" is used herein to refer to a molecular structure that helps the conjugates of the invention to localize to a targeting area, e.g., help enter a cell, or bind a receptor. Preferably, the targeting moiety comprises a vitamin, antibody, antigen, receptor, DNA, RNA, sialyl Lewis X antigen, hyaluronic acid, sugars, cell-specific lectins, steroid or steroid derivative, RGD peptide, ligand for a cell surface receptor, serum component, or combinatorial molecule directed against various intra- or extracellular receptors. The targeting moiety may also comprise a lipid or a phospholipid. Exemplary phospholipids include, without limitation, phosphatidylcholines, phospatidylserine, phospatidylinositol, phospatidylglycerol, and phospatidylethanolamine. These lipids may be in the form of micelles or liposomes and the like. The targeting moiety may further comprise a detectable label or alternately a detectable label may serve as a targeting moiety. When the conjugate has a targeting group comprising a detectable label, the amount and/or distribution/location of the polymer and/or the moiety (e.g., active agent) to which the polymer is coupled can be determined by using a suitable detector. Such labels include, without limitation, fluorescers, chemiluminescers, moieties used in enzyme labeling, colorimetric (e.g., dyes), metal ions, radioactive moieties, gold particles, quantum dots, and the like.

"Branched," in reference to the geometry or overall structure of a polymer, refers to a polymer having two or more polymers "arms" extending from a branch point.

"Forked," in reference to the geometry or overall structure of a polymer, refers to a polymer having two or more functional groups (typically through one or more atoms) extending from a branch point.

A "branch point" refers to a bifurcation point comprising one or more atoms at which a polymer branches or forks from a linear structure into one or more additional arms.

The term "reactive" or "activated" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

"Not readily reactive," with reference to a functional group present on a molecule in a reaction mixture, indicates that the group remains largely intact under conditions that are effective to produce a desired reaction in the reaction mixture.

A "protecting group" is a moiety that prevents or blocks reaction of a particular chemically reactive functional group in a molecule under certain reaction conditions. The protecting group may vary depending upon the type of chemically reactive group being protected as well as the reaction conditions to be employed and the presence of additional reactive or protecting groups in the molecule. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

A functional group in "protected form" refers to a functional group bearing a protecting group. As used herein, the term "functional group" or any synonym thereof encompasses protected forms thereof.

A "releaseable linkage" is a relatively labile bond that cleaves under physiological conditions. An exemplary releasable linkage is a hydrolyzable bond that cleaves upon reaction with water (i.e., is hydrolyzed). The tendency of a bond to hydrolyze in water may depend not only on the general type of linkage connecting two atoms but also on the substituents attached to these atoms. Appropriate hydrolytically unstable or weak linkages include but are not limited to carboxylate ester, phosphate ester, anhydrides, acetals, ketals, acyloxyalkyl ether, imines, orthoesters, peptides, oligonucleotides, thioesters, and carbonates. Certain functional groups have atoms that may be chemically degraded by a process other than hydrolysis. Exemplary releaseable linkages in this category include certain carbamates and Fmoc derivatives. Certain molecules containing these kinds of functionalities appropriately bonded may undergo chemical degradation (release) upon action of a base. In such cases "release" may occur at higher values of pH or through the action of biological molecules that contain basic moieties (e.g. histidines). Another exemplary releasable linkage is an enzymatically releasable linkage. An "enzymatically releasable linkage" means a linkage that is subject to cleavage by one or more enzymes.

A "stable" linkage or bond refers to a chemical bond that is substantially stable in water and, that is to say, does not undergo hydrolysis under physiological conditions to any appreciable extent over an extended period of time. Examples of hydrolytically stable linkages include but are not limited to the following: carbon-carbon bonds (e.g., in aliphatic chains) and non-special forms of the following functional types: ethers, amides, urethanes, amines, and the like. Generally, a stable linkage is one that exhibits a rate of hydrolysis of less than about 1-2% per day under physiological conditions. Hydrolysis rates of representative chemical bonds can be found in most standard chemistry textbooks.

"Substantially" or "essentially" means nearly totally or completely, for instance, 95% or greater, more preferably 97% or greater, still more preferably 98% or greater, even more preferably 99% or greater, yet still more preferably 99.9% or greater, with 99.99% or greater being most preferred of some given quantity.

"Alkyl" refers to a hydrocarbon chain, ranging from about 1 to 20 atoms in length. Such hydrocarbon chains are preferably but not necessarily saturated and may be branched or straight chain. Exemplary alkyl groups include methyl, ethyl, n-propyl, n-butyl, n-pentyl, 2-methyl-1-butyl, isopropyl, 3-methyl-1-pentyl, and the like. As used herein, "alkyl" includes cycloalkyl when three or more carbon atoms are referenced. An "alkenyl" group is an alkyl of 2 to 20 carbon atoms with at least one carbon-carbon double bond.

The terms "substituted alkyl" or "substituted $C_{q-r}$ alkyl" where q and r are integers identifying the range of carbon atoms contained in the alkyl group, denotes the above alkyl groups that are substituted by one, two or three halo (e.g., F, Cl, Br, I), trifluoromethyl, hydroxy, $C_{1-7}$ alkyl (e.g., methyl, ethyl, n-propyl, isopropyl, n-butyl, t-butyl, and so forth), $C_{1-7}$ alkoxy, $C_{1-7}$ acyloxy, $C_{3-7}$ heterocyclic, amino, phenoxy, nitro, carboxy, acyl, cyano. The substituted alkyl groups may be substituted once, twice or three times with the same or with different substituents.

"Lower alkyl" refers to an alkyl group containing from 1 to 7 carbon atoms, and may be straight chain or branched, as exemplified by methyl, ethyl, n-butyl, i-butyl, t-butyl. "Lower alkenyl" refers to a lower alkyl group of 2 to 6 carbon atoms having at least one carbon-carbon double bond.

"Non-interfering substituents" are those groups that, when present in a molecule, are typically non-reactive with other functional groups contained within the molecule.

"Alkoxy" refers to an —O—R group, wherein R is alkyl or substituted alkyl, preferably $C_1$-$C_{20}$ alkyl (e.g., methoxy, ethoxy, propyloxy, etc.), preferably $C_1$-$C_7$. For the purpose of this invention, alkoxy groups may also include aryl substituents when such substituents follow at least one alkyl group, e.g. benzyloxy. The latter are also called "arylalkoxy" substituents.

"Pharmaceutically acceptable excipient" or "pharmaceutically acceptable carrier" refers to component that may be included in the compositions of the invention causes no significant adverse toxicological effects to a patient.

The term "aryl" means an aromatic group having up to 14 carbon atoms. Aryl groups include phenyl, naphthyl, biphenyl, phenanthrenyl, naphthalenyl, and the like. "Substituted phenyl" and "substituted aryl" denote a phenyl group and aryl group, respectively, substituted with one, two, three, four or five (e.g., 1-2, 1-3 or 1-4 substituents) chosen from halo (F, Cl, Br, I), hydroxy, cyano, nitro, alkyl (e.g., $C_{1-6}$ alkyl), alkoxy (e.g., $C_{1-6}$ alkoxy), benzyloxy, carboxy, aryl, and so forth.

"Pharmacologically effective amount," "physiologically effective amount," and "therapeutically effective amount" are used interchangeably herein to mean the amount of a compound described herein that is needed to provide a desired level of active agent and/or conjugate in the bloodstream or in the target tissue. The precise amount may depend upon numerous factors, e.g., the particular active agent, the components and physical characteristics of the composition, intended patient population, patient considerations, and may readily be determined by one skilled in the art, based upon the information provided herein and available in the relevant literature.

A basic reactant or an acidic reactant described herein include neutral, charged, and any corresponding salt forms thereof which have basic or acidic character under any definition (i.e. Bronsted, Lewis, etc.).

The term "patient," refers to a living organism suffering from or prone to a condition that can be prevented or treated by administration of a conjugate as described herein, and includes both humans and animals.

"Optional" or "optionally" means that the subsequently described circumstance may but need not necessarily occur, so that the description includes instances where the circumstance occurs and instances where it does not.

As indicated above, the present invention is directed to (among other things) a compound comprising a des-ethyl sunitinib residue covalently attached via a releasable linkage-containing spacer moiety to a water-soluble, non-peptidic polymer. Following administration to a patient, the releasable linkage between the des-ethyl sunitinib residue and the water-soluble, non-peptidic polymer cleaves. Depending on the releasable linkage within the compound, des-ethyl sunitinib or des-ethyl sunitinib with a relatively small molecular fragment (or "tag") is released following cleavage.

The des-ethyl sunitinib residue is a residue of des-ethyl sunitinib, and refers to that portion of a polymer-des-ethyl sunitinib conjugate that corresponds to des-ethyl sunitinib.

In one or more embodiments of the invention, a compound is provided, the compound having the following structure:

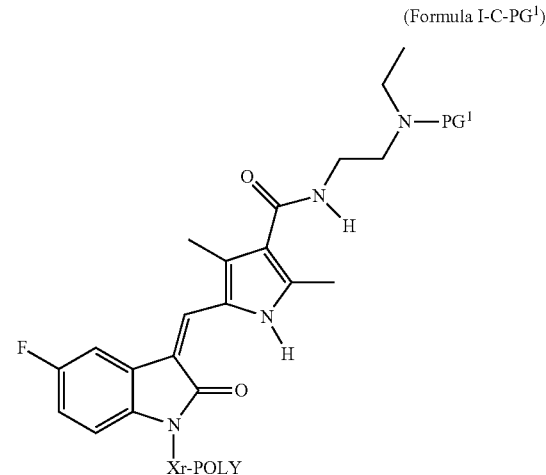

(Formula I-C-PG¹)

wherein:
PG¹ is H or an amine-protecting group;
Xr is a releasable linkage-containing spacer moiety; and
POLY is a water-soluble, non-peptidic polymer,
and pharmaceutically acceptable salts thereof.

In one or more embodiments of the invention, a compound is provided, the compound having the following structure:

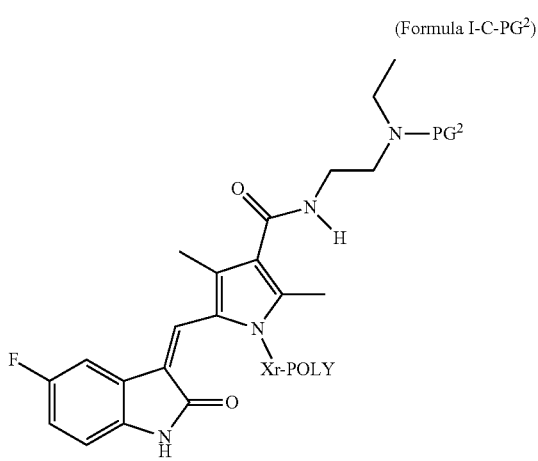

(Formula I-C-PG²)

wherein:
PG² is H or an amine-protecting group;
Xr is a releasable linkage-containing spacer moiety; and
POLY is a water-soluble, non-peptidic polymer,
and pharmaceutically acceptable salts thereof.

In one or more embodiments of the invention, a compound is provided, the compound having the following structure:

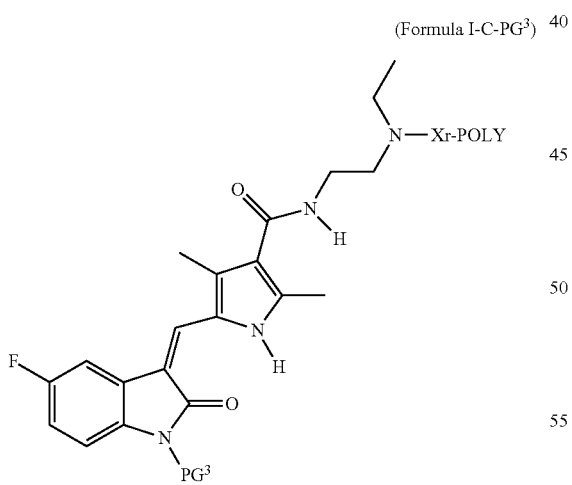

(Formula I-C-PG³)

wherein:
PG³ is H or an amine-protecting group;
Xr is a releasable linkage-containing spacer moiety; and
POLY is a water-soluble, non-peptidic polymer,
and pharmaceutically acceptable salts thereof.

In one or more embodiments of the invention, a compound is provided, the compound having the following structure:

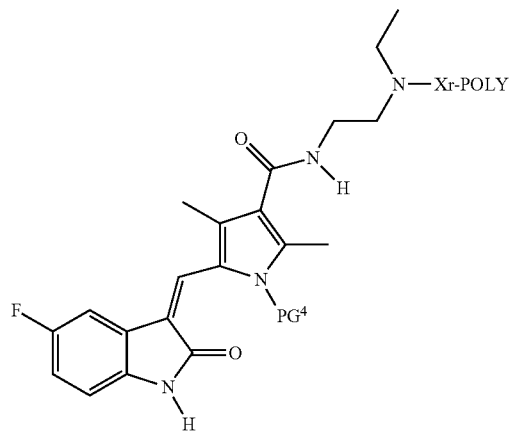

(Formula I-C-PG⁴)

wherein:
PG⁴ is H or an amine-protecting group;
Xr is a releasable linkage-containing spacer moiety; and
POLY is a water-soluble, non-peptidic polymer,
and pharmaceutically acceptable salts thereof.

In one or more embodiments of the invention, a compound is provided, the compound having the following structure:

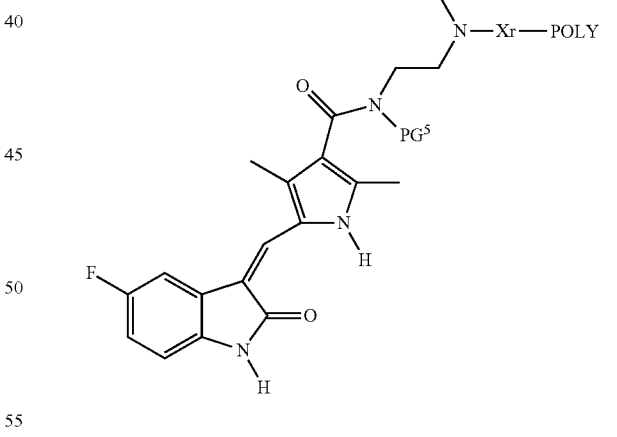

(Formula I-C-PG⁵)

wherein:
PG⁵ is H or an amine-protecting group;
Xr is a releasable linkage-containing spacer moiety; and
POLY is a water-soluble, non-peptidic polymer,
and pharmaceutically acceptable salts thereof.

Preferred exemplary compounds of the invention are encompassed by the following structure:

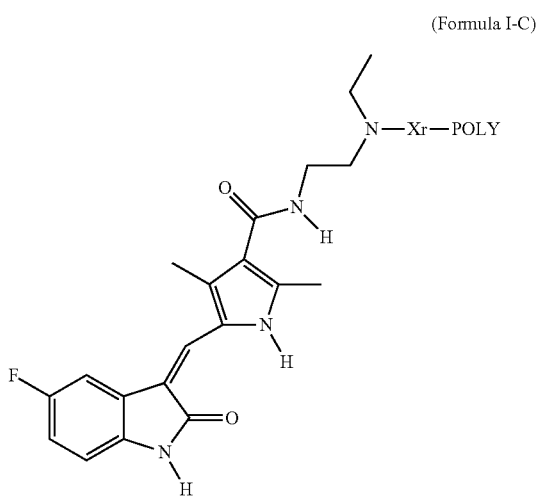

(Formula I-C)

wherein:
Xr is a releasable linkage-containing spacer moiety; and
POLY is a water-soluble, non-peptidic polymer,
and pharmaceutically acceptable salts thereof.

The Releasable Linkage-Containing Spacer Moiety, "Xr"

In order to effect release of des-ethyl sunitinib (or des-ethyl sunitinib with a relatively small molecular fragment), the compounds of the invention include a releasable linkage-containing spacer moiety between the des-ethyl sunitinib residue and the water-soluble, non-peptidic polymer. Thus, the releaseable linkage must be one that cleaves in vivo following administration to a patient. In this regard, releasable linkages are known to those of ordinary skill in the art. In addition, whether a given linkage can serve as a releasable linkage in connection with the compounds provided herein can be tested through experimentation (e.g., by administering a compound having the proposed releasable linkage to a patient and testing, e.g., via chromatographic techniques, periodically obtained blood samples for indications of cleavage).

Releasable linkages for use in connection with the compounds provided herein include functional groups that, when attached to an amine or amide group, undergo cleavage (release) by a chemical or enzymatic action. Thus such groups, which are often used as part of protecting groups for amines and amides, are candidates for linkages in the invention. Exemplary releasable linkages include, without limitation, thioether, carbamate, ester, carbonate, urea and enzyme-cleavable peptidic linkages. Thioether, carbamate, ester, carbonate and urea linkages can cleave via a β-elimination reaction (with or without the enzymatic coordination, e.g., an ester can serve as a releaseable linkage herein regardless of whether the ester will be cleaved via an esterase). While the rates of β-elimination reactions in vitro are often controlled by the pH of the medium, there are many basic species (e.g., proton acceptors) in biomolecules that may act as bases to accelerate release in vivo. One may consider this an enzymatic process although the base involved may be acting in a chemical capacity. Likewise there are many acidic species (e.g., proton donors) in biomolecules in vivo that may act to cause or accelerate hydrolysis.

With respect to enzyme-cleavable peptidic linkages, the spacer moiety can include a series of amino acids known to be a substrate for an enzyme present in the intended patient population. In this way, upon administration to the patient, the enzyme-cleavable peptidic linkage-containing compound of the invention, will cleave the enzyme-cleavable peptidic linkage via enzymatic cleavage, thereby releasing des-ethyl sunitinib (or des-ethyl sunitinib with a relatively small molecular fragment). Examples of peptidic linkages subject to enzymatic cleavage in a given patient population have been described (see, for example, U.S. Patent Application Publication No. 2005/0079155) and can be determined experimentally.

In one or more embodiments of the invention, the releasable linkage-containing spacer moiety, "Xr," can take the following structure:

(Formula III)

wherein:
(a) is either zero or one;
(b) is either zero or one;
$X^1$, when present, is a first spacer;
Lr is the releasable linkage; and
$X^2$, when present, is a second spacer.

In those instances of Formula III wherein both (a) and (b) are zero, it will be understood that the releasable linkage-containing spacer moiety is made up of only the releasable linkage. That is, the releasable linkage-containing spacer moiety only contains the releasable linkage and no other atoms are present between the des-ethyl sunitinib residue and the water-soluble, non-peptidic polymer. Nevertheless, the releaseable linkage may rely on surrounding atoms to activate the linkage to degrade, the principles of which are well known in the art.

In those instances of Formula III wherein either or both of (a) and (b) are one, it will be understood that the releasable linkage-containing spacer moiety contains one or more additional atoms other than those that make up the releasable linkage. Nonlimiting exemplary spacers (e.g., $X^1$ and $X^2$) that may flank the releasable linkage include —O—, —NH—, —S—, —S—S—, —N═N—, —C(O)—, —C(O)O—, —OC(O)—, —OC(O)O—, —OC(S)O—, —OC(O)S—, —OC(S)S—, —CH$_2$—C(O)O—, —CH$_2$—OC(O)—, —C(O)O—CH$_2$—, —OC(O)—CH$_2$—, C(O)—NH, NH—C(O)—NH, O—C(O)—NH, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$, —CH$_2$—CH$_2$—NH—C(O)—CH$_2$—CH$_2$, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, bivalent cycloalkyl group, —N(R$^6$)—, R$^6$ is H or an organic radical selected from the group consisting of alkyl, substituted alkyl, alkenyl, substituted alkenyl, alkynyl, substituted alkynyl, aryl and substituted aryl. Additional spacers include, acylamino, acyl, aryloxy, alkylene bridge containing between 1 and 5 inclusive carbon atoms, alkylamino, dialkylamino having about 2 to 4 inclusive carbon atoms, piperidino, pyrrolidino, N-(lower alkyl)-2-piperidyl, morpholino, 1-piperizinyl, 4-(lower alkyl)-1-piperizinyl, 4-(hydroxyl-lower alkyl)-1-piperizinyl, 4-(methoxy-lower alkyl)-1-piperizinyl, fluorenyl, and guanidine. For purposes of the present invention, however, a group of atoms is not considered a spacer when it is immediately adjacent to an polymeric segment, and the group of atoms is the same as a monomer of the polymer such that the group would represent a mere extension of the polymer chain.

When present, a spacer is typically but is not necessarily linear in nature. In addition, a spacer is typically but is not necessarily hydrolytically stable and/or is enzymatically stable. In one or more embodiments of the invention, the spacer, when present, has a chain length of less than about 12 atoms (e.g., less than about 10 atoms, less than about 8 atoms, and less than about 5 atoms). With respect to determining length of a particular spacer, length herein is defined as the number of atoms in a single chain, not counting substituents. For instance, a urea linkage such as this, R$_{polymer}$—NH—(C=O)—NH—R'$_{drug}$, is considered to have a chain length of three atoms (—NH—C(O)—NH—).

The Water-Soluble, Non-Peptidic Polymer, "POLY"

The compounds of the invention include a water-soluble, non-peptidic polymer. A wade array of polymers can be used and the invention is not limited with respect to the type (e.g., polyethylene oxide, polyoxazoline, and so forth), size (e.g., from 2 to 4000 monomers in size) and geometry (e.g., linear, branched, multi-armed, and so forth) used.

With respect to type, the water-soluble, non-peptidic polymer can be understood as a series of repeating monomers, wherein the type of monomer(s) dictates the type of water-soluble, non-peptidic polymer. Exemplary monomers include, but are not limited to the group consisting of: alkylene oxides, such as ethylene oxide or propylene oxide; olefinic alcohols, such as vinyl alcohol, 1-propenol or 2-propenol; vinyl pyrrolidone; hydroxyalkyl methacrylamide and hydroxyalkyl methacrylate, where, in each case, alkyl is preferably methyl; α-hydroxy acids, such as lactic acid or glycolic acid; phosphazene, oxazoline, carbohydrates such as monosaccharides, alditol such as mannitol; and N-acryloylmorpholine. In one or more embodiments, the water-soluble, non-peptidic polymer is a co-polymer of two monomer types selected from this group, or, more preferably, is a homo-polymer of one monomer type selected from this group. With respect to co-polymers, the two monomer types in a co-oligomer may be of the same monomer type, for example, two alkylene oxides, such as ethylene oxide and propylene oxide.

With respect to size, the water-soluble, non-peptidic polymer can be a relatively small or the water-soluble, non-peptidic polymer can be relatively large.

In those embodiments in which a relatively small water-soluble, non-peptidic polymer is present, exemplary values of molecular weights include: below about 2000; below about 1500; below about 1450; below about 1400; below about 1350; below about 1300; below about 1250; below about 1200; below about 1150; below about 1100; below about 1050; below about 1000; below about 950; below about 900; below about 850; below about 800; below about 750; below about 700; below about 650; below about 600; below about 550; below about 500; below about 450; below about 400; below about 350; below about 300; below about 250; below about 200; and below about 100 Daltons. Exemplary ranges for a relatively small water-soluble, non-peptidic polymer include from about 100 to about 1400 Daltons; from about 100 to about 1200 Daltons; from about 100 to about 800 Daltons; from about 100 to about 500 Daltons; from about 100 to about 400 Daltons; from about 200 to about 500 Daltons; from about 200 to about 400 Daltons; from about 75 to 1000 Daltons; and from about 75 to about 750 Daltons.

For relatively small water-soluble, non-peptidic polymers, the number of monomers in will typically fall within one or more of the following ranges: between 1 and about 30 (inclusive); between about 2 and about 25; between about 2 and about 20; between about 2 and about 15; between about 2 and about 12; between about 2 and about 10. In certain instances, the number of monomers in series in the polymer (and the corresponding conjugate) is one of 1, 2, 3, 4, 5, 6, 7, or 8. In additional embodiments, the polymer (and the corresponding conjugate) contains 9, 10, 11, 12, 13, 14, 15, 16, 17, 18, 19, or 20 monomers. In yet further embodiments, the polymer (and the corresponding conjugate) possesses 21, 22, 23, 24, 25, 26, 27, 28, 29 or 30 monomers in series. Thus, for example, when the water-soluble, non-peptidic polymer includes CH$_3$—(OCH$_2$CH$_2$)$_n$—, "n" is an integer that can be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, and can fall within one or more of the following ranges: between about 1 and about 25; between about 1 and about 20; between about 1 and about 15; between about 1 and about 12; between about 1 and about 10.

When the water-soluble, non-peptidic polymer has 1, 2, 3, 4, 5, 6, 7, 8, 9, or 10 monomers, these values correspond to a methoxy end-capped poly(ethylene oxide) having a molecular weights of about 75, 119, 163, 207, 251, 295, 339, 383, 427, and 471 Daltons, respectively. When the polymer has 11, 12, 13, 14, or 15 monomers, these values correspond to methoxy end-capped poly(ethylene oxide) having molecular weights corresponding to about 515, 559, 603, 647, and 691 Daltons, respectively.

When the molecular weight of the water-soluble, non-peptidic polymer in the compound is relatively large (e.g., greater than 2,000 Daltons), the weight can fall within the range of 2,000 Daltons to about 150,000 Daltons. Exemplary ranges, however, include molecular weights in the range of from about 3,000 Daltons to about 120,000 Daltons; in the range of from about 5,000 Daltons to about 110,000 Daltons; in the range of from greater than 5,000 Daltons to about 100,000 Daltons, in the range of from about 6,000 Daltons to about 90,000 Daltons, in the range of from about 10,000 Daltons to about 85,000 Daltons, in the range of greater than 10,000 Daltons to about 85,000 Daltons, in the range of from about 20,000 Daltons to about 85,000 Daltons, in the range of from about 53,000 Daltons to about 85,000 Daltons, in the range of from about 25,000 Daltons to about 120,000 Daltons, in the range of from about 29,000 Daltons to about 120,000 Daltons, in the range of from about 35,000 Daltons to about 120,000 Daltons, and in the range of from about 40,000 Daltons to about 120,000 Daltons.

Exemplary molecular weights for relatively large water-soluble, non-peptidic polymers include about 2,200 Daltons, about 2,500 Daltons, about 3,000 Daltons, about 4,000 Daltons, about 4,400 Daltons, about 4,500 Daltons, about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, and about 75,000 Daltons. Branched versions of the water-soluble, non-peptidic polymer (e.g., a branched 40,000 Dalton water-soluble polymer comprised of two 20,000 Dalton polymers) and multi-arm versions of the water-soluble, non-peptidic polymer (e.g., a four-armed 40,000 Dalton water-soluble polymer comprised of four 10,000 Dalton polymers) having a total molecular weight of any of the foregoing can also be used.

Thus, regardless of whether a relatively small or large water-soluble, non-peptidic polymer is used, when the water-soluble, non-peptidic polymer is a poly(ethylene oxide), the polymer will comprise a number of ($OCH_2CH_2$) monomers [or ($CH_2CH_2O$) monomers, depending on how the PEG is defined]. As used throughout the description, the number of repeating units is identified by the subscript "n" in "$(OCH_2CH_2)_n$." Thus, the value of (n) typically falls within one or more of the following ranges: from 2 to about 3400, from about 100 to about 2300, from about 100 to about 2270, from about 136 to about 2050, from about 225 to about 1930, from about 450 to about 1930, from about 1200 to about 1930, from about 568 to about 2727, from about 660 to about 2730, from about 795 to about 2730, from about 795 to about 2730, from about 909 to about 2730, and from about 1,200 to about 1,900. For any given polymer in which the molecular weight is known, it is possible to determine the number of repeating units (i.e., "n") by dividing the total weight-average molecular weight of the polymer by the molecular weight of the repeating monomer.

With respect to geometry, any geometry (e.g., linear, branched, multi-armed) can be used in connection with the conjugates of the invention and the invention is not limited in this regard.

With respect to linear water-soluble, non-peptidic polymers, typically, although not necessarily, a linear water-soluble, non-peptidic polymer will be terminally end capped with a substantially inert group (e.g., with a methyl or methoxy group) on the terminus not attached to releasable linkage-containing spacer moiety. In one or more embodiments, however, compounds of invention having a linear, water-soluble, non-peptidic polymer will not be terminally end capped with a substantially inert group and will instead have a functional group. In such embodiments, the linear, water-soluble, non-peptidic polymer can afford compounds of the invention having two sunitinib residues attached to it. In another form of such embodiments, the linear, water-soluble, non-peptidic polymer can afford compounds of the invention having a single sunitinib residue and a residue of a different moiety (e.g., a targeting moiety).

With respect to branched water-soluble, non-peptidic polymers, these polymers typically contain a two discernable end capped water-soluble, non-peptidic polymers connected via a branch point, which is connected through a spacer to either a functional group (prior to conjugation) or sunitinib residue. Exemplary branched forms of water-soluble, non-peptidic polymers are described herein and in WO 2005/107815, WO 2005/108463, U.S. Pat. Nos. 5,932,462 and 7,026,440, and U.S. Patent Application Publication No. 2005/0009988. Among other benefits, branched water-soluble, non-peptidic polymers—given the presence of two discernable water-soluble, non-peptidic polymers—have the potential to provide greater polymer character compared to, for example, a linear polymer having a single water-soluble, non-peptidic polymer.

As used herein, reference to a "water-soluble, non-peptidic polymer" (e.g., "POLY") is considered to include branched and multi-arm forms even though two or more discernable water-soluble, non-peptidic polymers can be identified.

With respect to multi-arm water-soluble, non-peptidic polymers, these polymers typically contain three or more discernable water-soluble, non-peptidic polymers, each having the ability to covalently attach to a moiety of interest, and each typically connected to a central core moiety (e.g., a residue of a polyol). Among other benefits, multi-arm water-soluble, non-peptidic polymers—given the ability of each arm to covalently attach to a drug—have the potential to provide greater drug character compared to, for example, a linear polymer having a single drug attached thereto.

Methods for Synthesizing Compounds of the Invention

The compounds discussed herein can be prepared in a variety of methods and the invention is not limited in this regard.

In one or more embodiments, the compounds of the invention are prepared by a method comprising covalently attaching a water-soluble, non-peptidic polymer to des-ethyl sunitinib, which is available commercially.

With respect to the water-soluble, non-peptidic polymer, such polymers can be obtained commercially in a form bearing one or more reactive groups, thereby providing a reagent suited for facile covalent attachment to des-ethyl sunitinib. In this form, the water-soluble, non-peptidic polymer is sometimes conventionally referred to as a polymeric reagent. Commercial suppliers for polymeric reagents include Nektar Therapeutics (Huntsville, Ala.), Sigma-Aldrich (St. Louis, Mo.), Creative PEGWorks (Winston Salem, N.C. USA), SunBio PEG-Shop (SunBio USA, Orinda, Calif.), JenKem Technology USA (Allen, Tex.), and NOF America Corporation (White Plains, N.Y.). Using routine experimentation, one of ordinary skill in the art can identify polymeric reagents having sizes, geometries, and reactive groups and so forth for preparing the compounds of the invention. For example, it is possible to prepare a series of compounds wherein each member in the series differs in a feature (e.g., the size of the water-soluble, non-peptidic polymer, the type of reactive groups, the ability of a linkage to release, and so forth) and then administer one member in the series to a patient followed by periodic detection and quantification (e.g., using chromatographic techniques) of blood and/or urine samples. Each member of the series is administered and quantified in a similar way to a naïve patient. Once each member of the series is tested, the results can be reviewed to determine which feature(s) provided compounds having the desired effect(s).

Covalently attaching the polymeric reagent to des-ethyl sunitinib is typically conducted under conjugation conditions, which conditions include combining des-ethyl sunitinib with a polymeric reagent (often a molar excess of polymeric reagent relative to des-ethyl sunitinib) under conditions of temperature, pH, time and solvent that allow for covalent attachment between a reactive group of the polymeric reagent to the preferred site, i.e. the "terminal amine" of des-ethyl sunitinib. For reference, the terminal amine of des-ethyl sunitinib is indicated below.

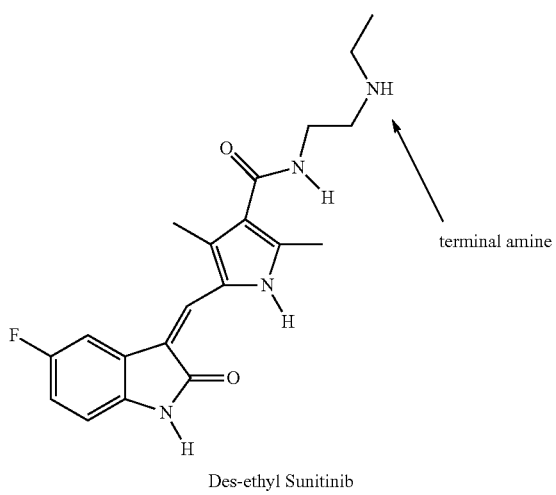 [SMILES: CCNCCNC(=O)c1c(C)[nH]c(/C=C2\C(=O)Nc3ccc(F)cc32)c1C]

Des-ethyl Sunitinib ← terminal amine

In one or more embodiments, the polymeric reagent used is selected such that (i) the reactive group of the polymeric reagent will form a covalent attachment at the terminal amine of des-ethyl sunitinib, and (ii) the polymeric reagent includes a releasable linkage (e.g., prior to being covalently attached) or will include a releasable linkage (e.g., following covalent attachment to des-ethyl sunitinib.

Exemplary conjugation conditions between a given polymeric reagent bearing a reactive group and des-ethyl sunitinib's terminal amine will be known to one of ordinary skill in the art based upon the disclosure provided herein and in the context of the relevant literature. See, for example, Poly(ethylene glycol) *Chemistry and Biological Applications*, American Chemical Society, Washington, D.C. (1997).

Exemplary linear polymeric reagents (along with exemplary conjugation conditions for those polymeric reagents) along with the releasable linkage-containing compounds formed therefrom are presented in Table 1.

TABLE 1

Exemplary Linear Polymeric Reagents and Releasable Linkage-Containing Compounds Formed Therefrom Exemplary Linear Polymeric Reagent (and exemplary conjugation conditions)

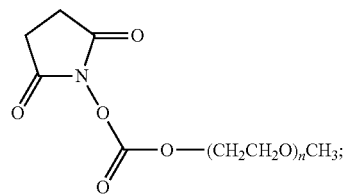

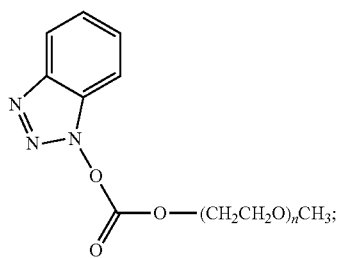

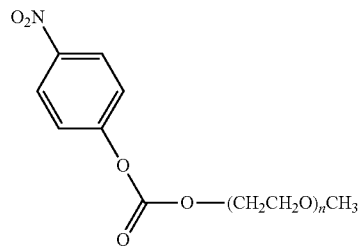

(acetonitrile/$H_2O$, $Na_2CO_3$; DMF, TEA)
wherein n is 4-2000

TABLE 1-continued
Exemplary Linear Polymeric Reagents and Releasable Linkage-Containing Compounds Formed Therefrom
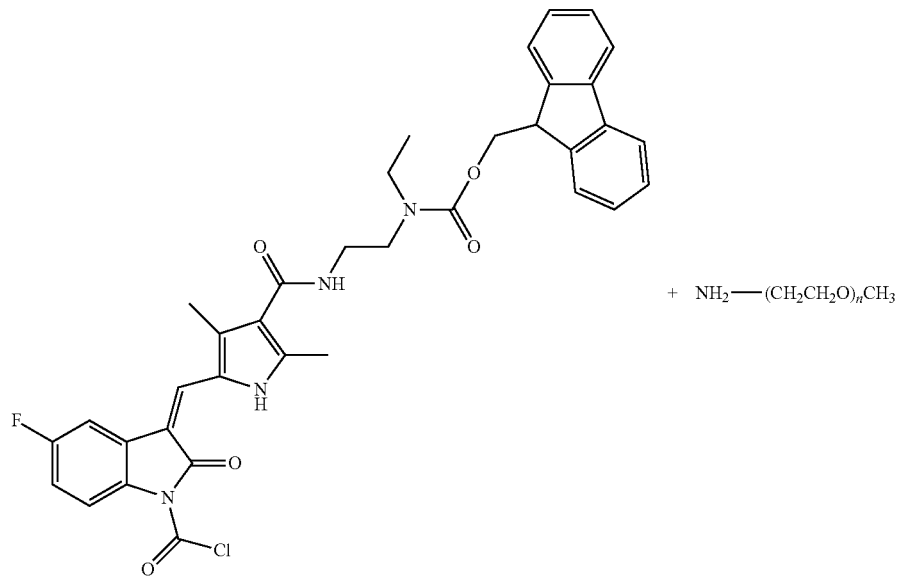
(tetrahydrofuran/acetonitrile, TEA)
wherein n is 4 to 2000
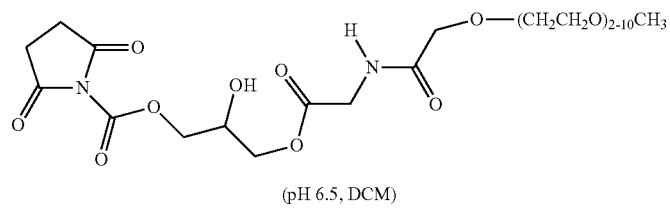
(pH 6.5, DCM)
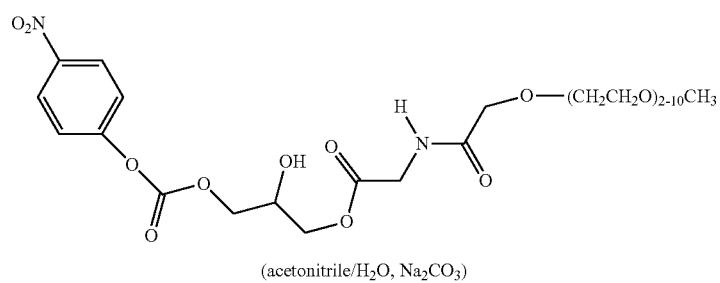
(acetonitrile/$H_2O$, $Na_2CO_3$)

TABLE 1-continued
Exemplary Linear Polymeric Reagents and Releasable Linkage-Containing Compounds Formed Therefrom
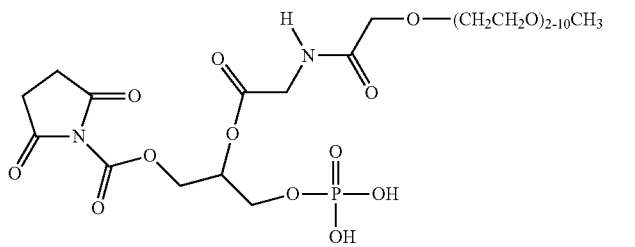
(pH 6.5, DCM)
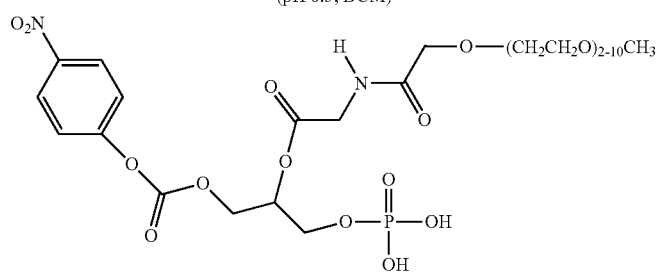
(acetonitrile/H$_2$O, Na$_2$CO$_3$)
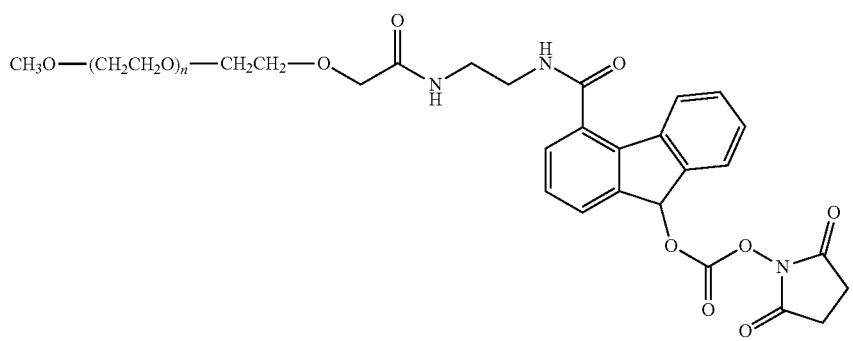
(pH 6.0, DCM)
wherein n is 100 to 2000
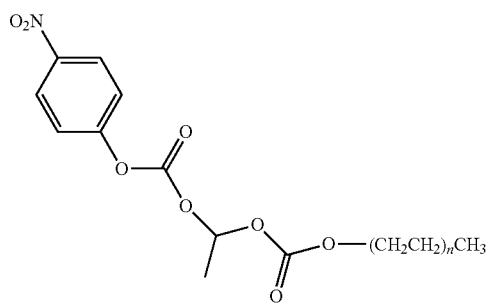
(acetonitrile/H$_2$O, Na$_2$CO$_3$)
wherein n is 100 to 2000
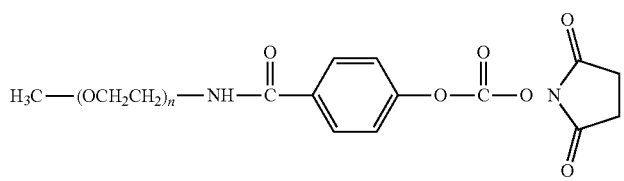
(acetonitrile/H$_2$O, Na$_2$CO$_3$)
wherein n is 100 to 2000

TABLE 1-continued

Exemplary Linear Polymeric Reagents and Releasable Linkage-Containing Compounds Formed Therefrom

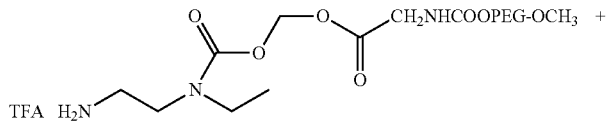

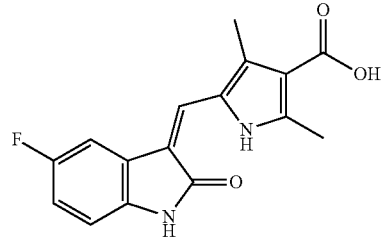 [SMILES: Cc1[nH]c(/C=C2\C(=O)Nc3ccc(F)cc32)c(C)c1C(=O)O]

(DMF, HOBT, TEA, DIC)
wherein PEG is —CH$_2$CH$_2$(OCH$_2$CH$_2$)$_n$ and n is
100 to 2000

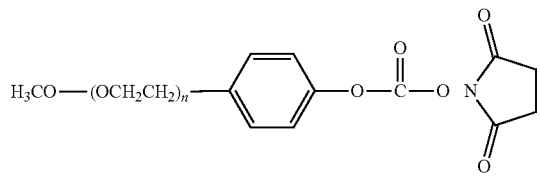

(acetonitrile/H$_2$O, Na$_2$CO$_3$)
wherein n is 100 to 2000

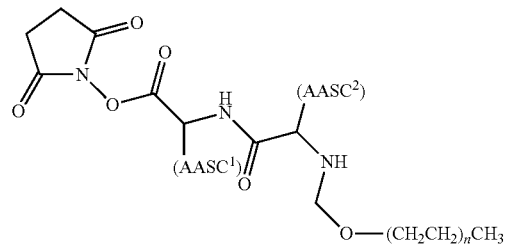

(pH 6.5, DCM)
wherein:
AASC$^1$ is a first amino acid side chain;
AASC$^2$ is a second amino acid side chain; and
AASC$^1$ and AASC$^2$ are defined such the
compound includes an enzymatically cleavable
linkage; and wherein n is 100 to 2000

Releasable Linkage-Containing Compound Formed Therefrom

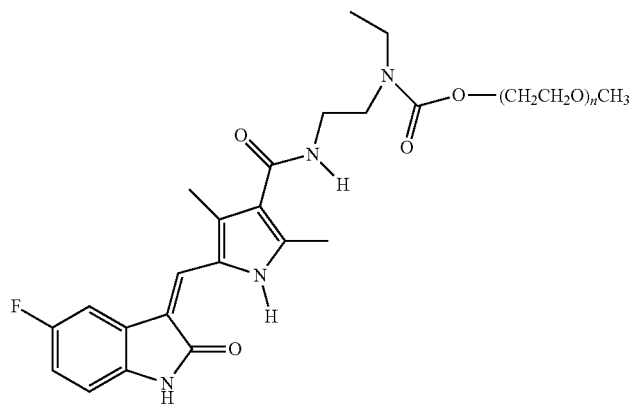

TABLE 1-continued
Exemplary Linear Polymeric Reagents and Releasable Linkage-Containing Compounds Formed Therefrom
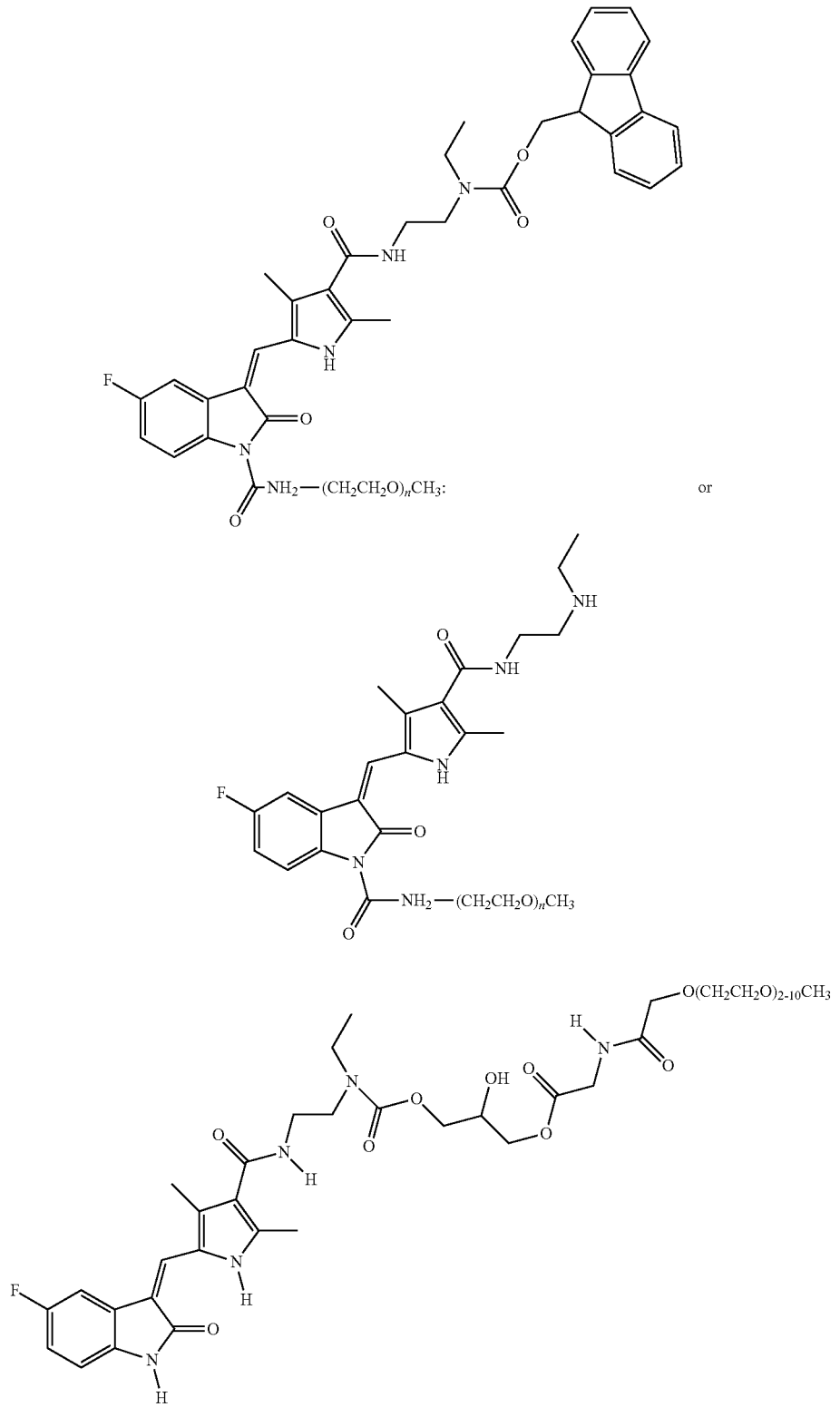

TABLE 1-continued
Exemplary Linear Polymeric Reagents and Releasable Linkage-Containing Compounds Formed Therefrom
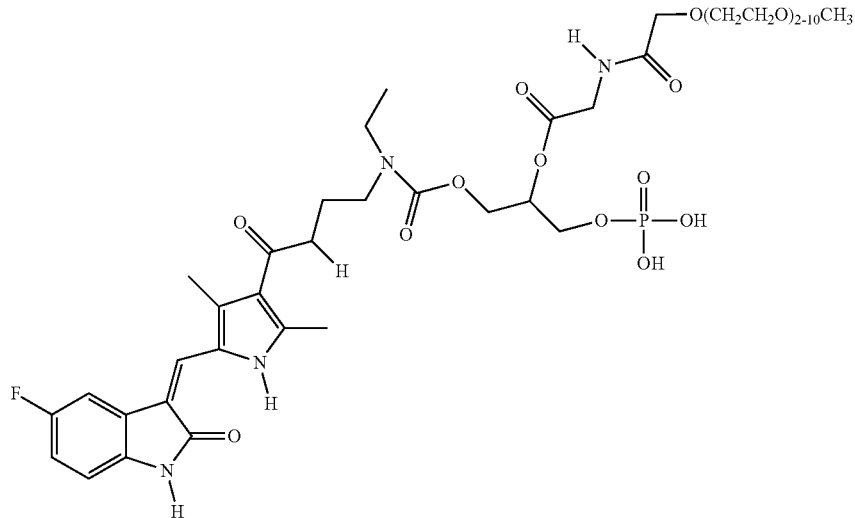
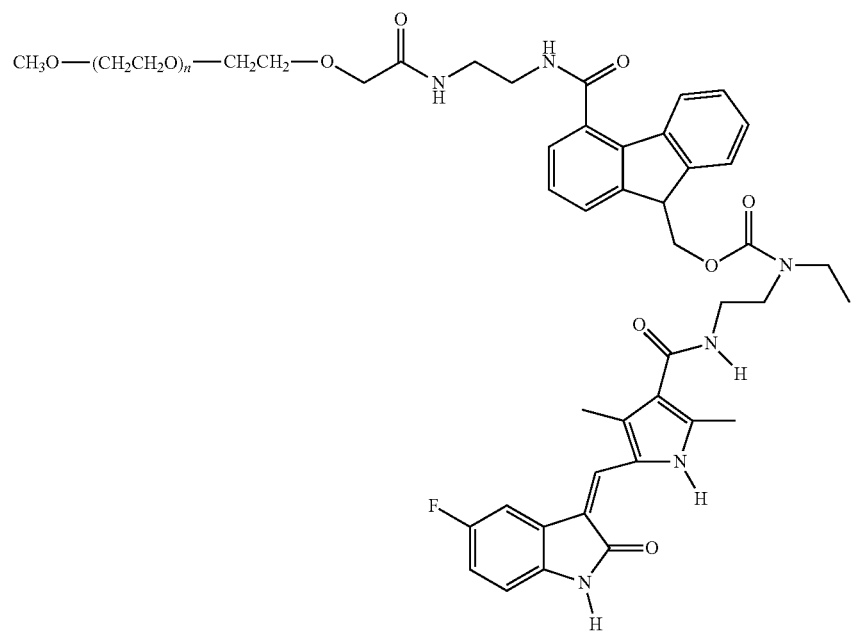
wherein n is 100 to 2000

TABLE 1-continued
Exemplary Linear Polymeric Reagents and Releasable Linkage-Containing Compounds Formed Therefrom
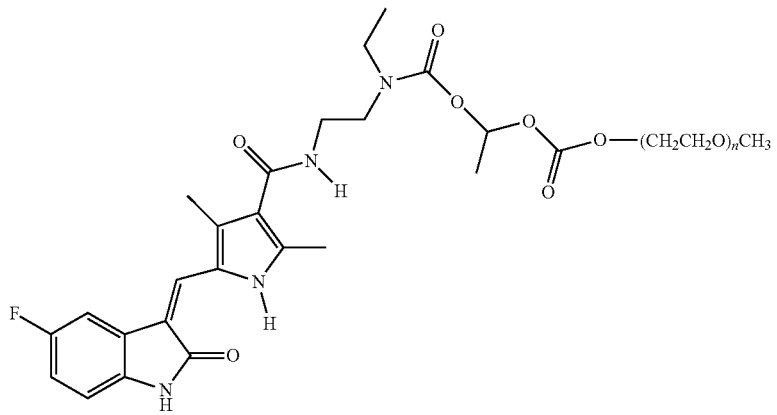
wherein n is 100 to 2000
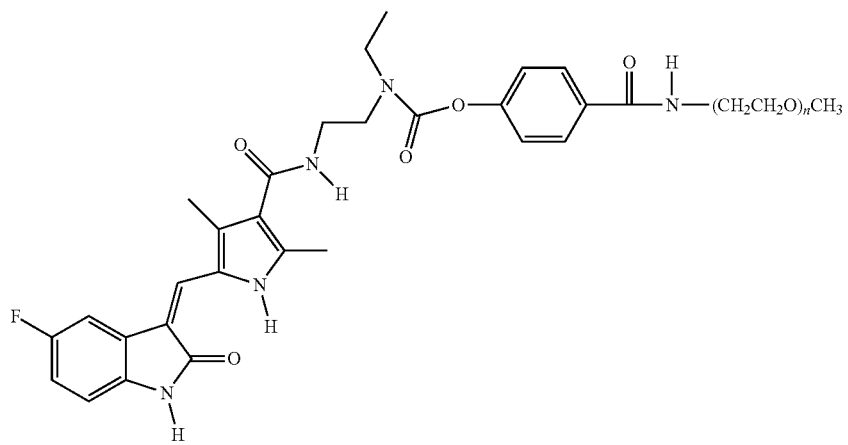
wherein n is 100 to 2000
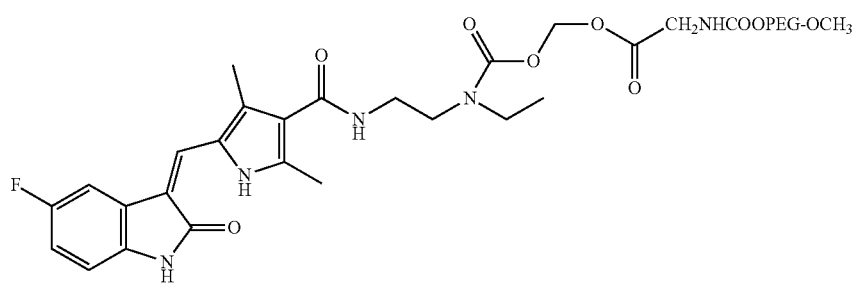

TABLE 1-continued

Exemplary Linear Polymeric Reagents and Releasable Linkage-Containing Compounds Formed Therefrom

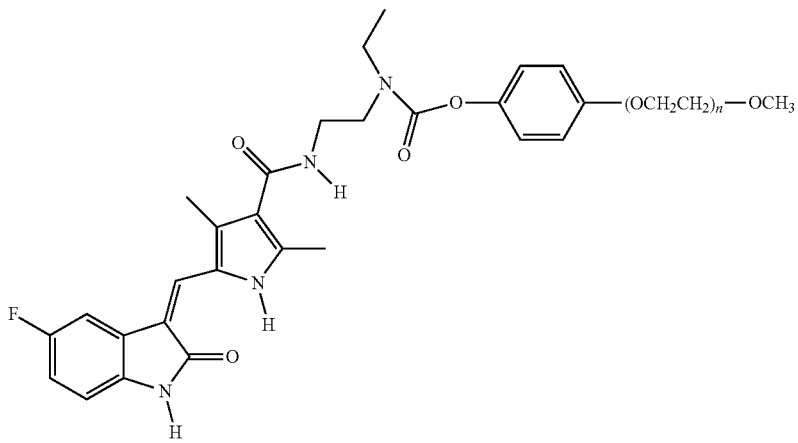

wherein n is 100 to 2000

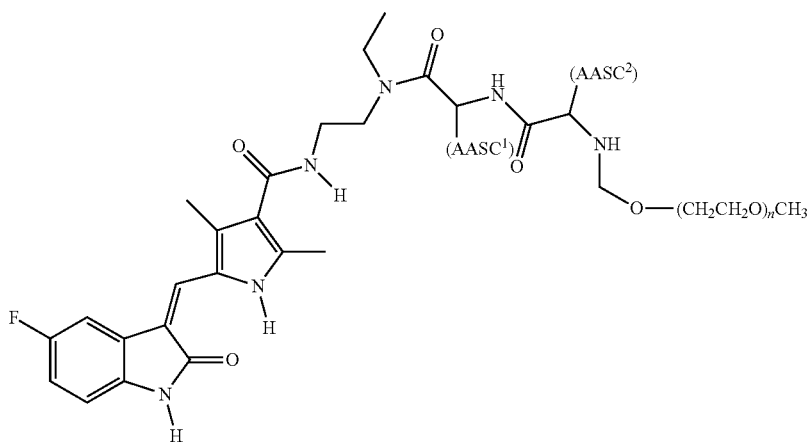

wherein:
AASC$^1$ is a first amino acid side chain;
AASC$^2$ is a second amino acid side chain; and
AASC$^1$ and AASC$^2$ are defined such the
compound includes an enzymatically cleavable
linkage; and wherein n is 100 to 2000

Exemplary branched polymeric reagents (along with exemplary conjugation conditions for those polymeric reagents) along with the releasable linkage-containing compounds formed therefrom are presented in Table 2. The branched polymeric reagents set forth in Table 2 can be prepared as described in U.S. Patent Application Publication No. 2006/0293499.

TABLE 2

Exemplary Linear Polymeric Reagents and Releasable Linkage-Containing Compounds Formed Therefrom

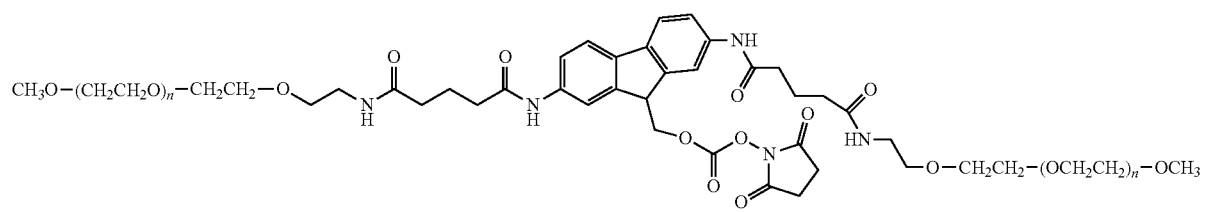

(pH 6.0, DCM)
wherein each n is independently 2 to 2000

TABLE 2-continued
Exemplary Linear Polymeric Reagents and Releasable Linkage-Containing Compounds Formed Therefrom
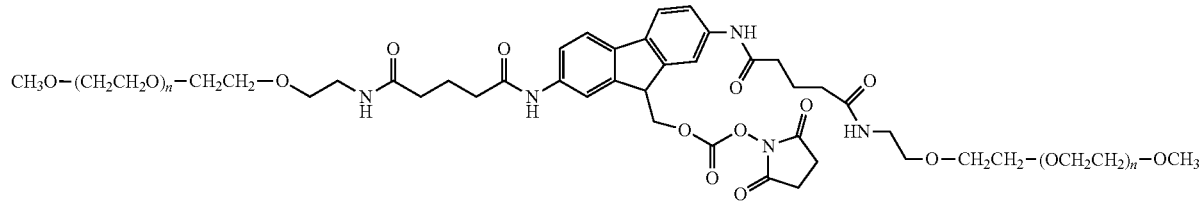
(pH 6.0, DCM)
wherein each n is independently 2 to 2000
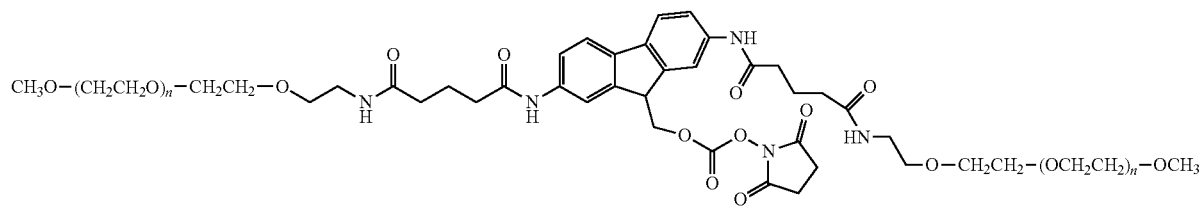
(pH 6.0, DCM)
wherein each n is independently 2 to 2000
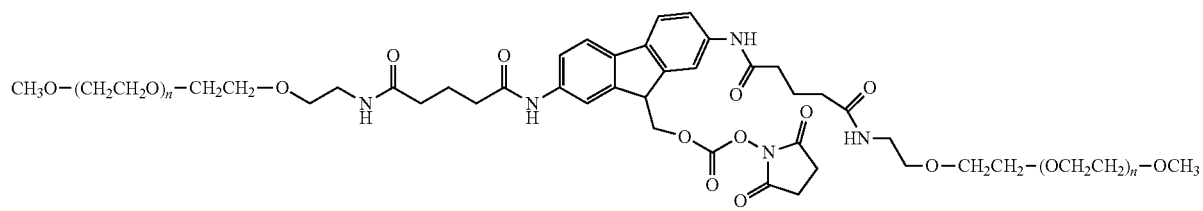
(pH 6.0, DCM)
wherein each n is independently 2 to 2000
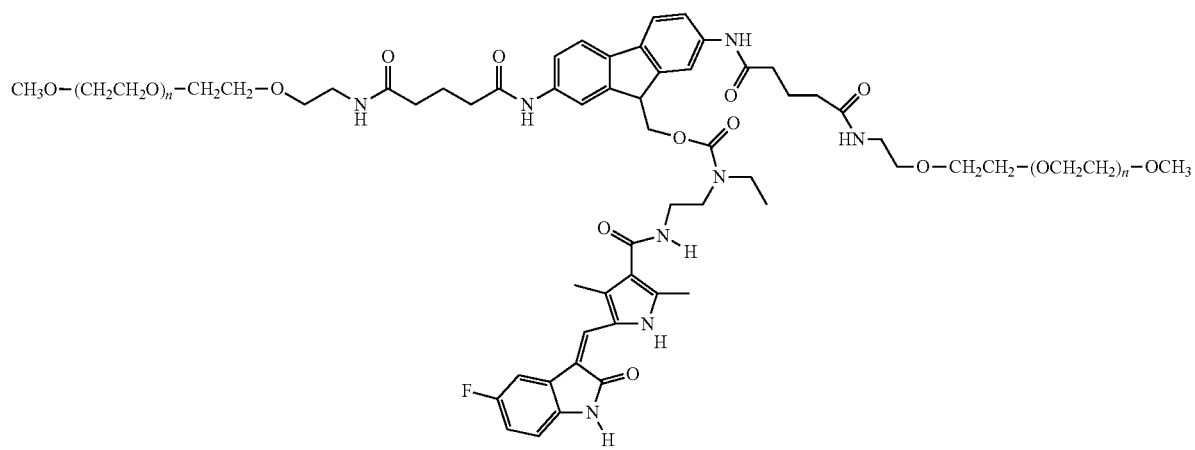
wherein each n is independently 2 to 2000

TABLE 2-continued
Exemplary Linear Polymeric Reagents and Releasable Linkage-Containing Compounds Formed Therefrom
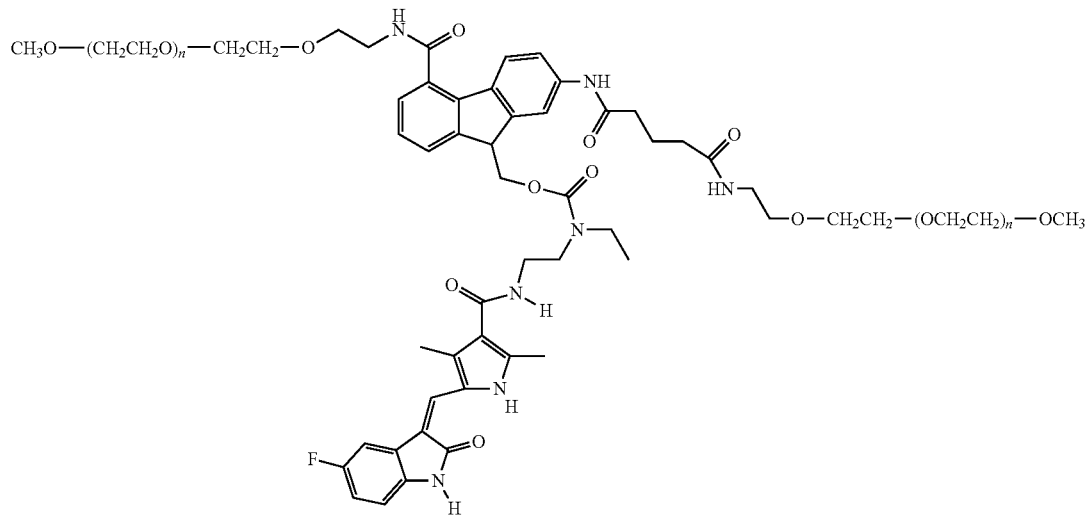
wherein each n is independently 2 to 2000
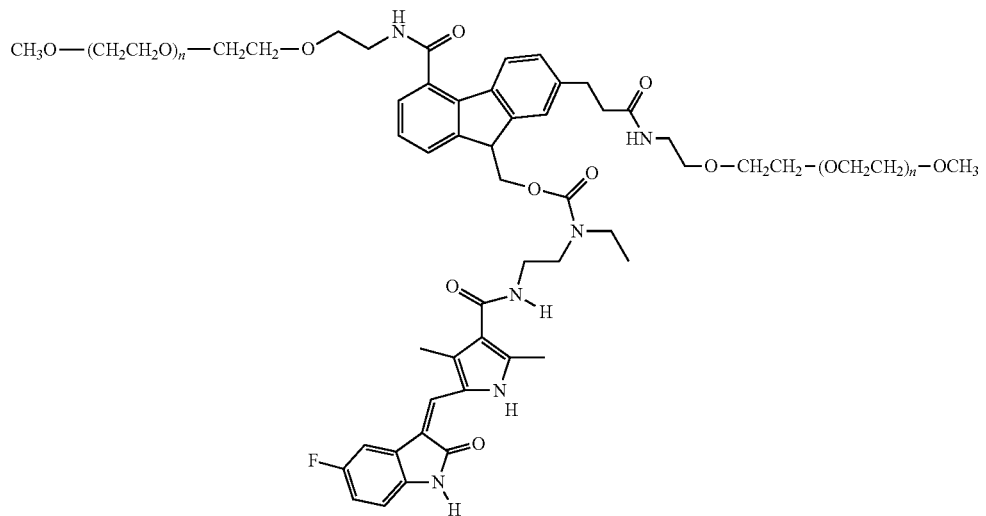
wherein each n is independently 2 to 2000
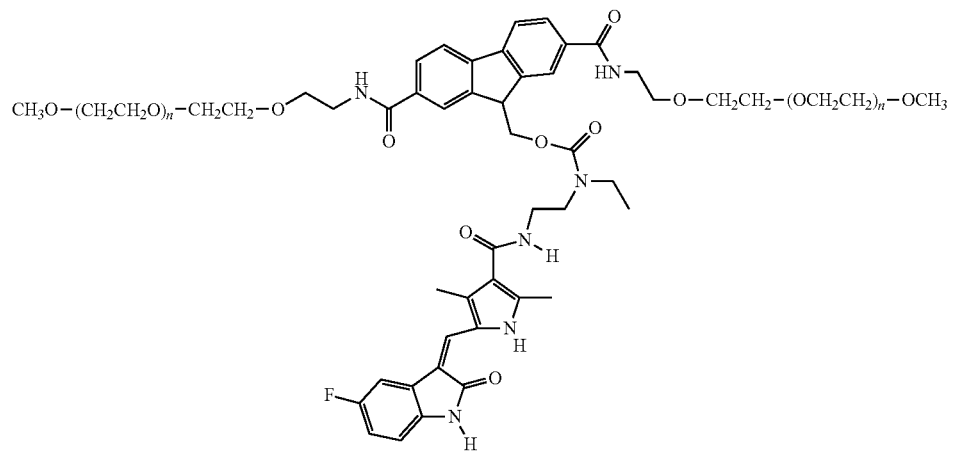
wherein each n is independently 2 to 2000

Exemplary multi-arm versions of compounds of the invention have structures encompassed by the formula:

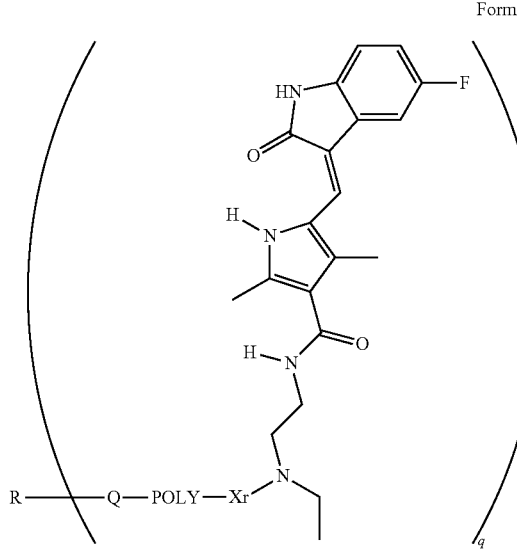

Formula I-C multi-arm
wherein:

R is a residue of polyol, polythiol or polyamine bearing at from 3 to about 50 hydroxyl, thiol or amino groups;

each Q is a linker (and, in one or more embodiments, a hydrolytically stable linker);

each Xr is a releasable linkage-containing spacer moiety;

each POLY is a water-soluble, non-peptidic polymer; and q is a positive integer from 3 to about 50 (e.g., 4), and pharmaceutically acceptable salts thereof.

Due to incomplete conversions, less than 100% yields, and other unavoidable complications routinely encountered during chemical syntheses, exemplary compositions comprising an exemplary "4-arm-PEG" compound can be characterized as compositions comprising four-arm compounds, wherein at least 90% of the four-arm compounds in the composition:

(i) have a structure encompassed by the formula,

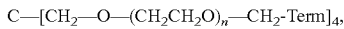

C—[CH$_2$—O—(CH$_2$CH$_2$O)$_n$—CH$_2$-Term]$_4$, wherein n, in each instance, is an integer having a value from 5 to 150 (e.g., about 113), and Term, in each instance, is selected from the group consisting of —OH, —C(O)OH,

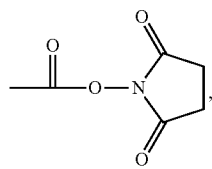

and —NH—CH$_2$—C(O)—O-Sun, wherein Sun is a residue of sunitinib or des-ethyl sunitinib; and (ii) for each Term in the at least 90% of the four-arm compounds in the composition, at least 90% are Sun.

As contemplated by the above structures (i.e., "Formula I-C, multi-arm"), the compound has "q" number of arms, i.e., from 3 to about 50. An exemplary number of arms includes 3, 4, 5, 6, 7, 9, and 10. In one or more embodiments, the compounds of the invention are prepared from multi-armed polymer reagents, which, in turn, are prepared from multi-arm polymers based on a multi-arm core molecule.

For example, in one approach, a multi-arm polymer can be prepared from a multi-arm core molecule by effectively "growing" a polymer onto each terminus of a multi-arm core molecule. By way of non-limiting example, it is possible to synthesize a polymer arm onto a polyol (e.g., pentaerythritol, diglycerol, etc.) via an ethoxylation reaction. In another exemplary approach, a multi-arm polymer can be prepared from a multi-arm core molecule by attaching a water-soluble, non-peptidic polymer onto each terminus of a multi-arm core molecule. The principles of both approaches are described in the literature and in, for example, U.S. Pat. No. 7,026,440. The invention, however, is not limited with regard to the specific approach taken.

In one or more embodiments, the residue of the polyol, polythiol or polyamine, "R," used in connection with the polymer is an organic radical-containing moiety possessing from about 3 to about 150 carbon atoms (e.g., from about 3 to about 50 carbon atoms, such as 3, 4, 5, 6, 7, 8, 9, and 10). The residue may contain one more heteroatoms (e.g., O, S, or N). In addition, the residue may be linear. In some instances, the residue may be cyclic.

As previously indicated, the residue of the polyol, polythiol or polyamine, "R," that forms the basis of the branching for the multi-armed compounds provided herein, originated from a corresponding polyol, polythiol or polyamine (prior to be incorporated into the multi-arm structures containing a water-soluble, non-peptidic polymer). In one or more embodiments, the corresponding polyol, polythiol, or a polyamine bears at least three hydroxyl, thiol, or amino groups, respectively, available for polymer attachment. A "polyol" is a molecule comprising three or more hydroxyl groups. A "polythiol" is a molecule that comprises three or more thiol groups. A "polyamine" is a molecule comprising three or more amino groups.

In one or more embodiments, the polyol, polyamine or polythiol will typically contain 3 to about 25 hydroxyl, or amino groups or thiol groups, respectively, such as from 3 to about 10 (i.e., 3, 4, 5, 6, 7, 8, 9, 10) hydroxyl, amino groups or thiol groups, respectively, preferably from 3 to about 8 (i.e., 3, 4, 5, 6, 7, or 8) hydroxyl, amino groups or thiol groups, respectively. In one or more embodiments, the number of atoms between each hydroxyl, thiol, or amino group will vary, although lengths of from about 1 to about 20 (e.g., from 1 to about 5) intervening atoms, such as carbon atoms, between each hydroxyl, thiol or amino group, are exemplary. In referring to intervening core atoms and lengths, —CH$_2$— is considered as having a length of one intervening atom, —CH$_2$CH$_2$— is considered as having a length of two atoms, and so forth.

Exemplary polyols and polyamines (for which corresponding residues could be present in the compounds provided herein) have (Radical)-(OH)$_q$ and (Radical)-(NH$_2$)$_q$ structures, respectively, where (Radical) corresponds to an organic-containing radical and q is a positive integer from 3 to about 50. Note that in Formula I-C, multi-arm, the variable "Q," when taken together with R, typically represents a residue of the core organic radical as described herein. That is to say, when describing polyols, polythiols and polymer amines, particularly by name, these molecules are being referenced in their form prior to incorporation into a water-soluble polymer-containing structure. So, for example, a compound of Formula I-C, multi-arm wherein R is a residue of the polyol, pentaerythritol [C(CH$_2$OH)$_4$], the residue "R" includes carbon (i.e., "C,") and together with "Q" represents "C(CH$_2$O—)$_4$."

Illustrative polyols include aliphatic polyols having from 1 to 10 carbon atoms and from 3 to 10 hydroxyl groups, including for example, trihydroxyalkanes, tetrahydroxyalkanes, polyhydroxy alkyl ethers, polyhydroxyalkyl polyethers, and the like. Cycloaliphatic polyols include straight chained or closed-ring sugars and sugar alcohols, such as mannitol, sorbitol, inositol, xylitol, quebrachitol, threitol, arabitol, erythritol, adonitol, dulcitol, facose, ribose, arabinose, xylose, lyxose, rhamnose, galactose, glucose, fructose, sorbose, mannose, pyranose, altrose, talose, tagitose, pyranosides, sucrose, lactose, maltose, and the like. Additional examples of aliphatic polyols include derivatives of glucose, ribose, mannose, galactose, and related stereoisomers. Aromatic polyols may also be used, such as 1,1,1-tris(4'-hydroxyphenyl)alkanes, such as 1,1,1-tris(4-hydroxyphenyl)ethane, 2,6-bis(hydroxyalkyl)cresols, and the like. Other core polyols that may be used include polyhydroxycrown ethers, cyclodextrins, dextrins and other carbohydrates (e.g., monosaccharides, oligosaccharides, and polysaccharides, starches and amylase).

Exemplary polyols include glycerol, trimethylolpropane, pentaerythritol, dipentaerythritol, tripentaerythritol, ethoxylated forms of glycerol, trimethylolpropane, pentaerythritol, dipentaerythritol, tripentaerythritol. Also, preferred are reducing sugars such as sorbitol and glycerol oligomers, such as diglycerol, triglycerol, hexaglycerol and the like. A 21-arm polymer can be synthesized using hydroxypropyl-β-cyclodextrin, which has 21 available hydroxyl groups. Additionally, a polyglycerol having an average of 24 hydroxyl groups is also included as an exemplary polyol.

Exemplary polyamines include aliphatic polyamines such as diethylene triamine, N,N',N"-trimethyldiethylene triamine, pentamethyl diethylene triamine, triethylene tetramine, tetraethylene pentamine, pentaethylene hexamine, dipropylene triamine, tripropylene tetramine, bis-(3-aminopropyl)-amine, bis-(3-aminopropyl)-methyl amine, and N,N-dimethyl-dipropylene-triamine. Naturally occurring polyamines that can be used in the present invention include putrescine, spermidine, and spermine. Numerous suitable pentamines, tetramines, oligoamines, and pentamidine analogs suitable for use in the present invention are described in Bacchi et al. (2002) *Antimicrobial Agents and Chemotherapy*, 46(1):55-61, which is incorporated by reference herein.

Provided below are illustrative structures corresponding to residues of polyols [although each structure is depicted with the oxygen atom ("O") derived from the corresponding hydroxyl group, each "O" can be substituted with sulfur ("S") or NH to depict the corresponding residue of a polythiol or polyamine, respectively). Note that the residues shown below would be understood in terms of compounds of Formula I-C, multi-arm as corresponding to "R" and "Q." In any event, conjugates based on any of the illustrative structures set forth below are included as part of the invention.

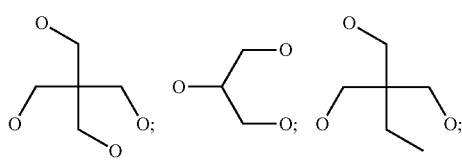

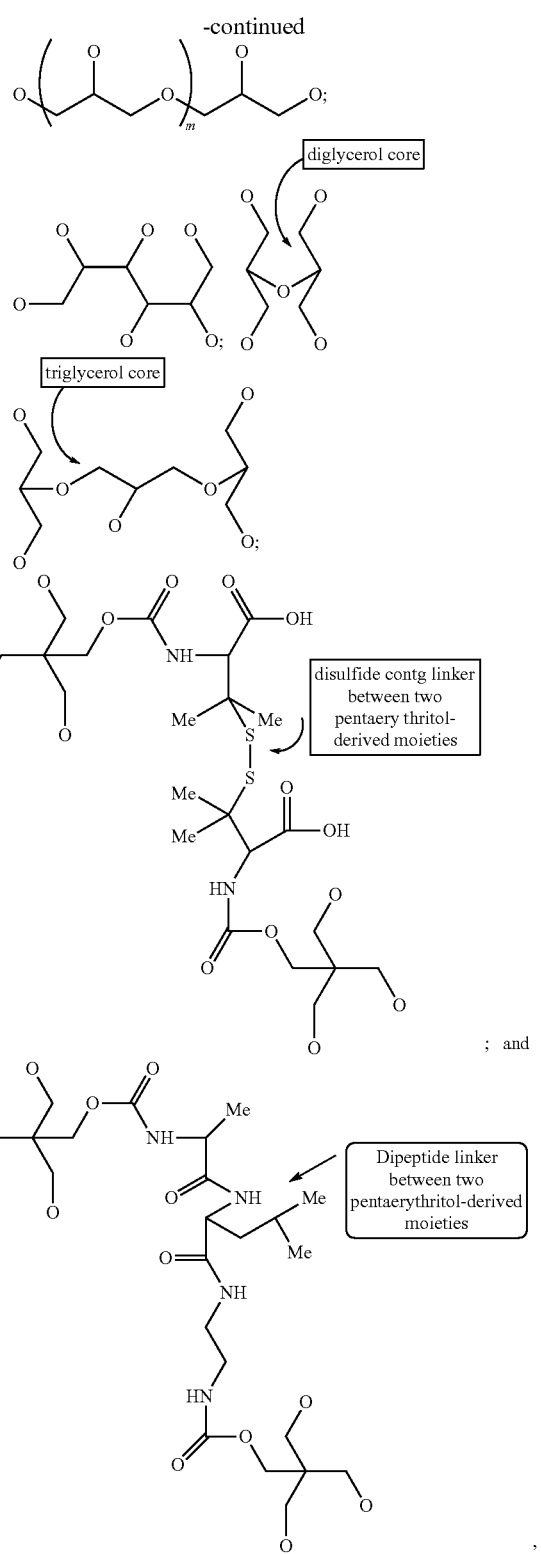

wherein m is a positive integer from 0-40 [e.g., 0-10, for example, 0-5 (i.e., 0, 1, 2, 3, 4, 5)].

Water-soluble, non-peptidic-containing multi-arm polymers (used as, for example, multi-arm polymeric reagents to prepare compounds of the invention) based on the above-described polyols, polythiols and polyamines and others are described in WO 2007/098466, WO 2010/019233 and U.S.

Pat. No. 7,744,861. These references and others describe methods for preparing such multi-arm polymers.

The linker, Q, serves to connect the residue of the polyol, polythiol or polyamine bearing at from 3 to about 50 hydroxyl, thiol or amino groups, "R," to each water-soluble, non-peptidic polymer, POLY, in compounds according to Formula I-C. In this regard, the invention is not limited with respect to the specific linker used. In one or more embodiments, the linker between the residue, "R," and the water-soluble, non-peptidic polymer, POLY, is a hydrolytically stable linker).

In one or more embodiments of the invention, the linker, Q, is influenced by the approach used to form the multi-arm polymer employed in preparing the compounds of the invention. For example, if a water-soluble, non-peptidic polymer bearing a functional group reactive to a hydroxyl, thiol or amine is reacted with a polyol, polythiol or polyamine, respectively, the linker, Q, may include one or more atoms incorporating the bond formed between the termini of the polyol, polythiol or polamine and the beginning of the repeating monomers of the water-soluble, non-peptidic polymer, POLY. Illustrative linking chemistries in this regard (along with the resulting linkers) are described in the literature and in, for example, Wong (1991) "*Chemistry of Protein Conjugation and Crosslinking*", CRC Press, Boca Raton, Fla., and Brinkley (1992) Bioconjug. Chem. 3:2013.

In one or more embodiments of compounds of Formula I-C, multi-arm, Q contains at least one heteroatom such as O, or S, or NH, where the atom proximal to R in Q, when taken together with R, typically represents a residue of an organic radical-containing core of the polyol, polythiol or polyamine. Generally, the linker, Q, contains from 1 to about 10 atoms (e.g., from 1 to about 5 atoms). The linker, Q, typically contains a number of atoms selected from the group consisting of: 1, 2, 3, 4, 5, 6, 7, 8, 9, or 10. Illustrative Qs include O, S, —NH—, —NH—C(O)— and —C(O)—NH—.

The remaining variables in each of Formula I-C, multi-arm include the water-soluble, non-peptidic polymer, POLY and the releasable linkage-containing spacer moiety, both of which have already been discussed. With respect to compounds encompassed by Formula I-C, multi-arm, however, typical molecular weights for the water-soluble, non-peptidic polymer (e.g., each POLY) include: about 200, about 250, about 300, about 400, about 500, about 600, about 700, about 800, about 900, about 1,000, about 1,500, about 2,000, about 3,000, about 4,000, about 5,000, about 6,000, about 7,000, about 7,500, about 8,000, about 9,000, about 10,000, about 12,000, about 15,000, about 17,500, about 18,000, about 19,000 and about 20,000 Daltons.

Utility and Testing of Compounds

Animal models (rodents and dogs) can used to study oral drug transport. In addition, non-in vivo methods include rodent everted gut excised tissue and Caco-2 cell monolayer tissue-culture models. These models are useful in predicting oral drug bioavailability (thereby providing an indication of whether a given compound of the invention can be administered orally).

To test for binding activity, a compound can be tested using in vitro binding studies to receptors using various cell lines expressing these receptors. In vitro binding studies known to those of ordinary skill in the art can be used to test the binding for a receptor of interest.

The following assay may be used to determine the level of activity and effect of a compound on protein kinases. The assay is performed in an ELISA (Enzyme-Linked Immunosorbent Sandwich Assay) format [Voller et al. (1980), "Enzyme-Linked Immunosorbent Assay," Manual of Clinical Immunology, 2d ed., Rose and Friedman, *Am. Soc. Of Microbiology*, Washington, D.C., pp. 359-371]. The general procedure is as follows:

a compound is introduced to cells expressing the test kinase, either naturally or recombinantly, for a selected period of time after which, if the test kinase is a receptor, a ligand known to activate the receptor is added. The cells are lysed and the lysate is transferred to the wells of an ELISA plate previously coated with a specific antibody recognizing the substrate of the enzymatic phosphorylation reaction. Non-substrate components of the cell lysate are washed away and the amount of phosphorylation on the substrate is detected with an antibody specifically recognizing phospho-tyrosine compared with control cells that were not contacted with a test compound. Similar assays can be designed along the same lines for any protein kinase using techniques well known in the art.

Using this basic approach, one can test over 80 protein kinases, including GST-Flk1, pyk2, PYK2, FGFR-1R, EGFR, PDGFR, HER-2, CDK2, and IGF-1.

The compounds of the invention may be tested in animal models of cancers to determine their cancer-inhibition potential. An exemplary model is the xenograft-based assay. In this assay, the ability of human tumors to grow as xenografts in athymic mice (e.g., Balb/c, nu/nu) provides a useful in vivo model for studying the biological response to therapies for human tumors. Since the first successful xeno-transplantation of human tumors into athymic mice [Rygaard et al. (1969) *Acta Pathol. Microbial. Scand.* 77:758-760], many different human tumor cell lines (e.g., mammary, lung, genitourinary, gastro-intestinal, head and neck, glioblastoma, bone, and malignant melanomas) have been transplanted and successfully grown in nude mice.

In addition to an approach as provided in the Experimental, the following assays may be used to determine the level of activity, specificity and effect of the different compounds of the present invention. Three general types of assays are useful for evaluating compounds: cellular/catalytic, cellular/biological and in vivo. The object of the cellular/catalytic assays is to determine the effect of a compound on the ability of a tyrosine kinase to phosphorylate tyrosines on a known substrate in a cell. The object of the cellular/biological assays is to determine the effect of a compound on the biological response stimulated by a tyrosine kinase in a cell. The object of the in vivo assays is to determine the effect of a compound in an animal model of a particular disorder such as cancer.

Suitable cell lines for subcutaneous xenograft experiments include C6 cells (glioma, ATCC #CCL 107), A375 cells (melanoma, ATCC #CRL 1619), A431 cells (epidermoid carcinoma, ATCC #CRL 1555), Calu 6 cells (lung, ATCC #HTB 56), PC3 cells (prostate, ATCC #CRL 1435), SKOV3TP5 cells and NIH 3T3 fibroblasts genetically engineered to overexpress EGFR, PDGFR, IGF-1R or any other kinase. The following protocol can be used to perform xenograft experiments.

Female athymic mice (BALB/c, nu/nu) are maintained under clean-room conditions in micro-isolator cages with Alpha-dri bedding. They receive sterile rodent chow and water ad libitum.

Cell lines are grown in appropriate medium [for example, MEM, DMEM, Ham's F10, or Ham's F12 plus 5%-10% fetal bovine serum (FBS) and 2 mM glutamine (GLN)]. All cells are grown in a humid atmosphere of 90-95% air and 5-10% $CO_2$ at 37° C. All cell lines are routinely subcultured twice a week and are negative for mycoplasma as determined by the Mycotect method (Gibco).

Cells are harvested at or near confluency with 0.05% Trypsin-EDTA and pelleted at 450×g for ten minutes. Pellets are resuspended in sterile PBS or media (without FBS) to a particular concentration and the cells are implanted into the hindflank of the mice (8-10 mice per group, $2\text{-}10 \times 10^6$ cells/animal). Tumor growth is measured over 3 to 6 weeks using venier calipers. Tumor volumes are calculated as a product of length×width×height. P values are calculated using the Students t-test. Test compounds in 50-100 µL excipient (DMSO, or VPD:D5W) can be delivered by IP injection at different concentrations generally starting at day one after implantation.

The compounds of the invention may be administered per se or in the form of a pharmaceutically acceptable salt, and any reference to the compounds of the invention herein is intended to include pharmaceutically acceptable salts. If used, a salt of a compound as described herein should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable salts can be prepared by reaction of the compound with an organic or inorganic acid, using standard methods detailed in the literature. Examples of useful salts include, but are not limited to, those prepared from the following acids: hydrochloric, hydrobromic, sulfuric, nitric, phosphoric, maleic, acetic, salicyclic, p-toluenesulfonic, tartaric, citric, methanesulfonic, formic, malonic, succinic, naphthalene-2-sulphonic and benzenesulphonic, and the like. Also, pharmaceutically acceptable salts can be prepared as alkaline metal or alkaline earth salts, such as sodium, potassium, or calcium salts of a carboxylic acid group.

The compounds of the invention may contain one or more chiral centers and for each chiral center, the invention contemplates each optical isomer as well as any combination or ratio of or an optically active form, for example, a single optically active enantiomer, or any combination or ratio of enantiomers (e.g., scalemic and racemic mixtures). In addition, the small molecule drug may possess one or more geometric isomers. With respect to geometric isomers, a composition can comprise a single geometric isomer or a mixture of two or more geometric isomers.

The present invention also includes pharmaceutical preparations comprising a compound as provided herein in combination with a pharmaceutical excipient. Generally, the compound itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, maltitol, lactitol, xylitol, sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines, fatty acids and fatty esters; steroids, such as cholesterol; and chelating agents, such as EDTA, zinc and other such suitable cations.

Pharmaceutically acceptable acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the conjugate in the composition will vary depending on a number of factors, but will optimally be a therapeutically effective dose when the composition is stored in a unit dose container. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. The optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, excipients will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients and general teachings regarding pharmaceutical compositions are described in "Remington: The Science & Practice of Pharmacy", 19$^{th}$ ed., Williams & Williams, (1995), the "Physician's Desk Reference", 52$^{nd}$ ed., Medical Economics, Montvale, N.J. (1998), and Kibbe, A. H., Handbook of Pharmaceutical Excipients, 3$^{rd}$ Edition, American Pharmaceutical Association, Washington, D.C., 2000.

The pharmaceutical compositions can take any number of forms and the invention is not limited in this regard. Exemplary preparations are most preferably in a form suitable for oral administration such as a tablet, caplet, capsule, gel cap, troche, dispersion, suspension, solution, elixir, syrup, lozenge, transdermal patch, spray, suppository, and powder.

Oral dosage forms are preferred for those conjugates that are orally active, and include tablets, caplets, capsules, gel caps, suspensions, solutions, elixirs, and syrups, and can also comprise a plurality of granules, beads, powders or pellets that are optionally encapsulated. Such dosage forms are prepared using conventional methods known to those in the field of pharmaceutical formulation and described in the pertinent texts.

Tablets and caplets, for example, can be manufactured using standard tablet processing procedures and equipment. Direct compression and granulation techniques are preferred when preparing tablets or caplets containing the conjugates described herein. In addition to the conjugate, the tablets and caplets will generally contain inactive, pharmaceutically acceptable carrier materials such as binders, lubricants, disintegrants, fillers, stabilizers, surfactants, coloring agents, flow agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethylcellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the conjugate-containing composition can be encapsulated in the form of a liquid or gel (e.g., in the case of a gel cap) or solid (including particulates such as granules, beads, powders or pellets). Suitable capsules include hard and soft capsules, and are generally made of gelatin, starch, or a cellulosic material. Two-piece hard gelatin capsules are preferably sealed, such as with gelatin bands or the like.

Included are parenteral formulations in the substantially dry form (as a lyophilizate or precipitate, which can be in the form of a powder or cake), as well as formulations prepared for injection, which are liquid and require the step of reconstituting the dry form of parenteral formulation. Examples of suitable diluents for reconstituting solid compositions prior to injection include bacteriostatic water for injection, dextrose 5% in water, phosphate-buffered saline, Ringer's solution, saline, sterile water, deionized water, and combinations thereof.

In some cases, compositions intended for parenteral administration can take the form of nonaqueous solutions, suspensions, or emulsions, normally being sterile. Examples of nonaqueous solvents or vehicles are propylene glycol, polyethylene glycol, vegetable oils, such as olive oil and corn oil, gelatin, and injectable organic esters such as ethyl oleate.

The parenteral formulations described herein can also contain adjuvants such as preserving, wetting, emulsifying, and dispersing agents. The formulations are rendered sterile by incorporation of a sterilizing agent, filtration through a bacteria-retaining filter, irradiation, or heat.

The compounds of the invention can also be administered through the skin using conventional transdermal patch or other transdermal delivery system, wherein the conjugate is contained within a laminated structure that serves as a drug delivery device to be affixed to the skin. In such a structure, the conjugate is contained in a layer, or "reservoir," underlying an upper backing layer. The laminated structure can contain a single reservoir, or it can contain multiple reservoirs.

The compounds of the invention can also be formulated into a suppository for rectal administration. With respect to suppositories, the compound is mixed with a suppository base material which is (e.g., an excipient that remains solid at room temperature but softens, melts or dissolves at body temperature) such as coca butter (theobroma oil), polyethylene glycols, glycerinated gelatin, fatty acids, and combinations thereof. Suppositories can be prepared by, for example, performing the following steps (not necessarily in the order presented): melting the suppository base material to form a melt; incorporating the compound (either before or after melting of the suppository base material); pouring the melt into a mold; cooling the melt (e.g., placing the melt-containing mold in a room temperature environment) to thereby form suppositories; and removing the suppositories from the mold.

In some embodiments of the invention, the compositions comprising the compounds of the invention may further be incorporated into a suitable delivery vehicle. Such delivery vehicles may provide controlled and/or continuous release of the compounds and may also serve as a targeting moiety. Non-limiting examples of delivery vehicles include, adjuvants, synthetic adjuvants, microcapsules, microparticles, liposomes, and yeast cell wall particles. Yeast cells walls may be variously processed to selectively remove protein component, glucan, or mannan layers, and are referred to as whole glucan particles (WGP), yeast beta-glucan mannan particles (YGMP), yeast glucan particles (YGP), *Rhodotorula* yeast cell particles (YCP). Yeast cells such as *S. cerevisiae* and *Rhodotorula* species are preferred; however, any yeast cell may be used. These yeast cells exhibit different properties in terms of hydrodynamic volume and also differ in the target organ where they may release their contents. The methods of manufacture and characterization of these particles are described in U.S. Pat. Nos. 5,741,495, 4,810,646, 4,992,540, 5,028,703, 5,607,677 and U.S. Patent Application Publication Nos. 2005/0281781 and 2008/0044438.

The invention also provides a method for administering a compound of the invention as provided herein to a patient suffering from a condition that is responsive to treatment with the compound. The method comprises administering, generally orally, a therapeutically effective amount of the compound (preferably provided as part of a pharmaceutical preparation). Other modes of administration are also contemplated, such as pulmonary, nasal, buccal, rectal, sublingual, transdermal, and parenteral. As used herein, the term "parenteral" includes subcutaneous, intravenous, intra-arterial, intraperitoneal, intracardiac, intrathecal, and intramuscular injection, as well as infusion injections.

In instances where parenteral administration is utilized, it may be necessary to employ somewhat bigger oligomers than those described previously, with molecular weights ranging from about 500 to 30K Daltons (e.g., having molecular weights of about 500, 1000, 2000, 2500, 3000, 5000, 7500, 10000, 15000, 20000, 25000, 30000 or even more).

In one or more embodiments of the invention, a method is provided, the method being directed to a method of treating diseases mediated by abnormal protein kinase activity, in particular, receptor tyrosine kinases (RTKs), non-receptor protein tyrosine kinases (CTKs) and serine/threonine protein kinases (STKs), in a patient, in particular humans, which method comprises administering to said patient a pharmaceutical composition comprising a compound of the invention as described herein. Such diseases include, by way of example and not limitation, cancer, diabetes, hepatic cirrhosis, cardiovasacular disease such as atherosclerosis, angiogenesis, immunological disease such as autoimmune disease and renal disease.

In one or more embodiments of the invention. The invention is directed to the use of a compound of the invention as described herein in the preparation of a medicament which is useful in the treatment of a disease mediated by abnormal PK activity.

The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 1000 mg, preferably in doses from 0.01 mg/day to 750 mg/day, and more preferably in doses from 0.10 mg/day to 500 mg/day.

The unit dosage of any given compound of the invention (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All articles, books, patents, patent publications and other publications referenced herein are incorporated by reference in their entireties. In the event of an inconsistency between the teachings of this specification and the art incorporated by reference, the meaning of the teachings in this specification shall prevail.

EXPERIMENTAL

It is to be understood that while the invention has been described in conjunction with certain preferred and specific embodiments, the foregoing description as well as the examples that follow are intended to illustrate and not limit the scope of the invention. Other aspects, advantages and modifications within the scope of the invention will be apparent to those skilled in the art to which the invention pertains.

All non-PEG chemical reagents referred to in the appended examples are commercially available and/or can be prepared using art-known techniques described in the literature unless otherwise indicated.

1H NMR (nuclear magnetic resonance) data was generated by an NMR spectrometer (unless otherwise indicated, NMR data was not collected above ~12.8 ppm).

Example 1

Synthesis of 2-Aminoethyl-FMOC Linked PEG-Des-ethyl Sunitinib Conjugates

In this example, an approach reflected by the reaction scheme set forth in the schematic below was followed.

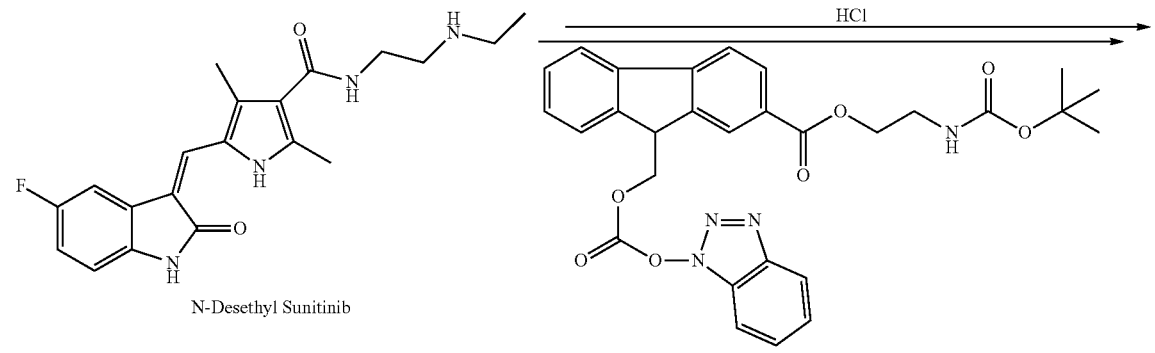

1a

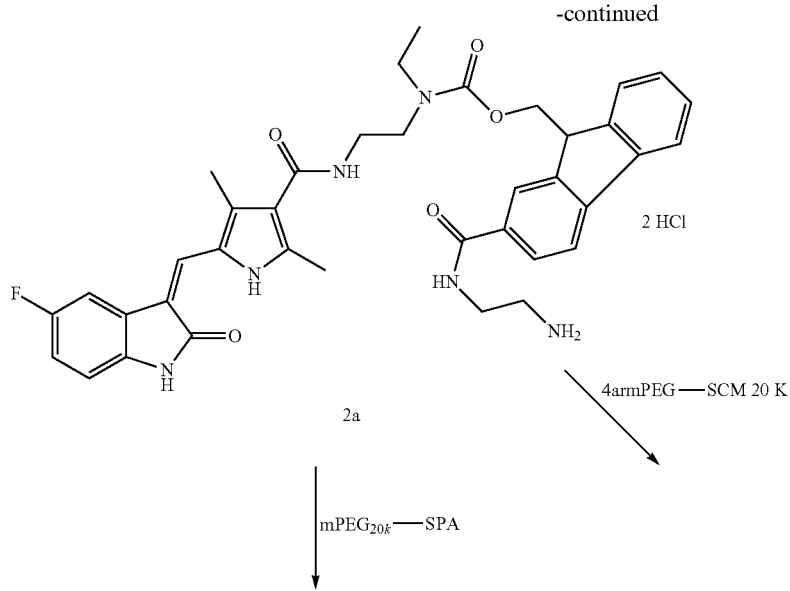
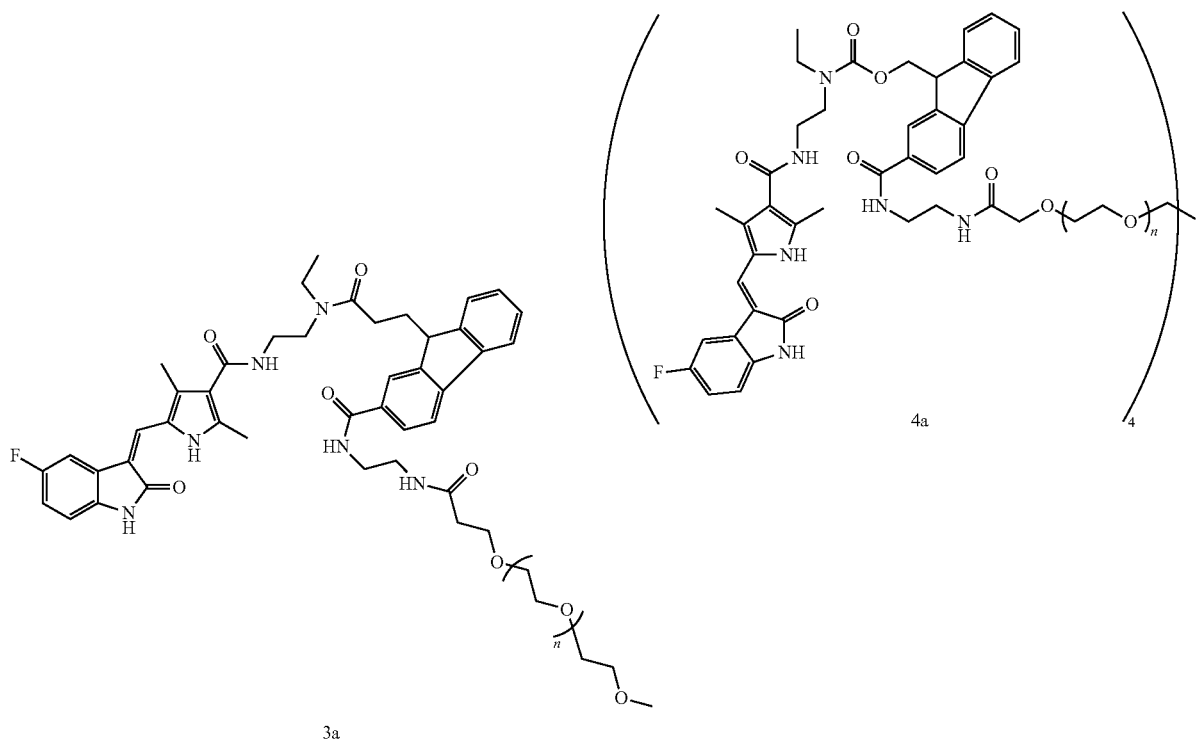
In preparing the linker ("linker a" in the schematic above), the following reaction scheme set forth in the schematic below was followed.
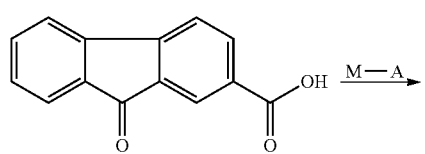
-continued
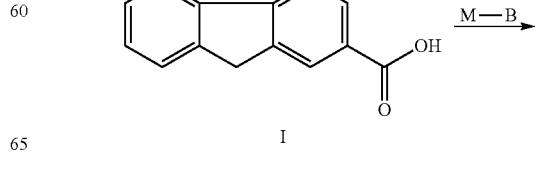

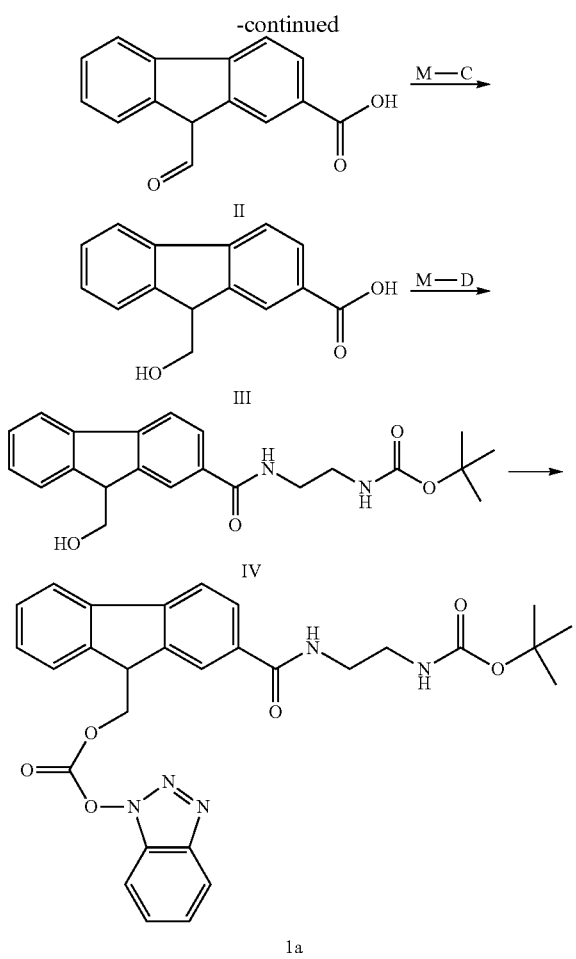

Method A ("M-A")

Synthesis of 9H-fluorene-2-carboxylic acid (Compound I)

In a 250 mL round bottomed flask was added 9-oxo-9H-fluorene-2-carboxylic acid (9.82 g, 43.8 mmol) in diethylene glycol (70 mL) to give a yellow suspension. Sodium hydroxide (6.1 g, 1.5 mol) and hydrazine hydrate (80% in water, 7.5 mL, 187 mmol) were added. The solution was heated in an oil bath with stirring at 120° C. Yellow solids were present therefore more diethylene glycol (150 mL) was added. The temperature was increased to 165° C. Two hours later the reaction mixture was cooled to room temperature and allowed to stand overnight. Approximately 12 hours later, deionized water (200 mL) was added to reaction mixture and all solids dissolved. The clear, yellow solution was heated at 120° C. and acidified with concentrated hydrochloric acid to pH 2. The precipitated yellow solids were filtered and washed with deionized water (700 mL). The wet solids were redissolved in 0.2M NaOH (500 mL) and heated at 60° C. The solution was acidified with concentrated hydrochloric acid to pH 2. The yellow solids were filtered and washed with deionized water (500 mL). The product was placed under reduced pressure with phosphorus pentoxide present. Yield: 7.1 g (77%). HPLC analysis was on C18 applying an acetonitrile gradient with 0.1% TFA; retention time was 8.6 min with >99% purity at 320 nm. $^1$H-NMR (DMSO-d$_6$, 500 MHz): δ (ppm) 8.1 (s, 1H, —CH); 8.0 (m, 3H, 3-CH); 7.6 (d, 1H, —CH); 7.4 (m, 2H, 2-CH); 4.0 (s, 2H, —CH$_2$).

Method B ("M-B")

Synthesis of 9-formyl-9H-fluorene-2-carboxylic acid (Compound II)

In a 250 mL round bottom flask was added 9H-fluorene-2-carboxylic acid (4.24 g, 20.15 mmol) in anhydrous dimethyl sulfoxide (86 mL). Ethyl formate (26.5 mL, 326 mmol) and potassium tert-butoxide (18.5 g, 165 mmol) were added. Gas evolution was observed and the solution was brownish black in color. After 40 minutes, deionized water (200 mL) was slowly added to the reaction mixture. Concentrated hydrochloric acid was added until pH was approximately 2. The product was extracted with ethyl acetate. The ethyl acetate layer was washed with 5% sodium chloride (6×200 mL). The ethyl acetate layer was dried with sodium sulfate and filtered. The solution was evaporated to dryness. Yield: 4.96 g (100%). HPLC analysis was on C18 applying an acetonitrile gradient with 0.1% TFA; retention time was 6.6 and 7.3 min (two forms of formyl group) with >99% purity at 320 nm.

Method C ("M-C")

Synthesis of 9-(hydroxymethyl)-9H-fluorene-2-carboxylic acid (Compound III)

In a 250 mL round bottom flask was added sodium borohydride (8.02 g, 212 mmol) and deionized water (59 mL, pre-sparged with nitrogen gas). The solution was placed in an ice bath to cool. The cold sodium borohydride solution was added slowly to a 250 mL round bottom flask containing 9-formyl-9H-fluorene-2-carboxylic acid (4.96 g, 20.82 mmol). The reaction was maintained at 0° C. for 15 minutes then was allowed to come to room temperature. One hour later at room temperature, the reaction solution was chilled in an ice bath. Deionized water (200 mL) and methanol (200 mL) were added. Concentrated hydrochloric acid was added slowly until the pH was approximately 2 while maintaining a cold reaction mixture. (The purpose for low temperature is to avoid fulvene formation that can occur with elevated temperatures in aqueous basic conditions.) The product was extracted with ethyl acetate (400, 100 mL). The extracts were combined and washed with 5% sodium chloride (200 mL×2). The ethyl acetate extract was dried with anhydrous sodium sulfate. The solution was filtered and evaporated to dryness. The product was placed under reduced pressure to remove residual solvents. Yield: 4.91 g (98%). HPLC analysis was on C18 applying an acetonitrile gradient with 0.1% TFA; retention time was 3.6 min with >99% purity at 320 nm. $^1$H-NMR (DMSO-d$_6$, 500 MHz): δ (ppm) 8.2 (s, 1H, —CH); 8.0 (m, 3H, 3-CH); 7.7 (d, 1H, —CH); 7.5 (m, 2H, 2-CH); 4.1 (t, 1H, —CH); 3.9, 3.7 (t, 2H, —CH$_2$).

Method D ("M-D")

Synthesis of tert-butyl 2-(9-(hydroxymethyl)-9H-fluorene-2-carboxamido)ethylcarbamate (Compound IV)

To a 100 mL round bottom flask was added 9-(hydroxymethyl)-9H-fluorene-2-carboxylic acid (2.424 g, 10.09 mmol) and anhydrous dimethylformamide (25 mL). Tert-butyl 2-aminoethylcarbamate (2.435 g, 14.47 mmol), anhydrous hydroxybenzotriazole (1.459 g, 10.80 mmol) and N1-((ethylimino)methylene)-N3,N3-dimethylpropane-1,3-diamine hydrochloride (2.44 g, 12.73 mmol) were added. Anhydrous dimethylformamide (5 mL) was added to rinse wall of round bottom flask. After 24 hours, ethyl acetate (150 mL) was added to the reaction mixture. The solution was washed with a solution of 0.1 M hydrochloric acid/5% sodium chloride (3×150 mL) and 5% sodium chloride (150 mL). The ethyl acetate extract was dried with anhydrous sodium sulfate and filtered. The filtrate was evaporated under reduced pressure. The product was placed under vacuum to dry. Yield: 3.79 g (98%). HPLC analysis was on C18 applying an acetonitrile gradient with 0.1% TFA; retention time was 6.7 minutes with >99% purity at 300 nm. $^1$H-NMR (CDCl$_3$, 500 MHz): δ (ppm) 8.1 (s, 1H, —CH); 7.8 (m, 3H, 3-CH); 7.7 (d, 1H, —CH); 7.4 (m, 2H, 2-CH); 4.1 (m, 2H, —CH$_2$); 4.0 (m, 2H, —CH); 3.6 (t, 2H, —CH$_2$); 3.4 (t, 2H, —CH$_2$); 1.4 (s, 9H, —(CH$_3$)$_3$).

Synthesis of 2-(tert-butoxycarbonylamino)ethyl 9-(((1H-benzo[d][1,2,3]triazol-1-yloxy)carbonyloxy) methyl)-9H-fluorene-2-carboxylate (Compound 1a)

To a 500 mL round bottom flask was added tert-butyl 2-(9-(hydroxymethyl)-9H-fluorene-2-carboxamido)ethylcarbamate (3.5 g, 9.15 mmol) in anhydrous acetonitrile (220 mL). Di(1H-benzo[d][1,2,3]triazol-1-yl)carbonate, 66.7% by weight (4.28 g, 9.64 mmol) was added to the reaction solution with anhydrous acetonitrile (45 mL). Anhydrous pyridine (2.22 mL, 27.4 mmol) was added. Approximately two hours later, more di(1H benzo[d][1,2,3]triazol-1-yl) carbonate, 66.7% weight (0.84 g, 1.891 mmol) was added. The product was not isolated. HPLC analysis was on C18 applying an acetonitrile gradient with 0.1% TFA; 2.37 min with 91% purity at 280 nm. A portion of the reaction solution (120 mL) was evaporated to dryness and redissolved in anhydrous THF (230 mL) to prepare Compound 1a.

Synthesis of (Z)—N-(2-(ethylamino)ethyl)-5-((5-fluoro-2-oxoindolin-3-ylidene)methyl)-2,4-dimethyl-1H-pyrrole-3-carboxamide dihydrochloride (N-Desethyl Sunitinib)

In a 50 mL round bottom flask was added (Z)-5-((5-fluoro-2-oxoindolin-3-ylidene)methyl)-2,4-dimethyl-1H-pyrrole-3-carboxylic acid (120.8 mg, 0.402 mmol) in anhydrous dimethylformamide (10 mL). Tert-butyl 2-aminoethyl (ethyl)carbamate) (158.1 mg, 0.840 mmole), anhydrous hydroxybenzotriazole (56.7 mg, 0.420 mmol) and N1-((ethylimino)methylene)-N3,N3-dimethylpropane-1,3-diamine hydrochloride (141.0 mg, 0.736 mmol) were added. At 24 hours, N1-((ethylimino)methylene)-N3,N3-dimethylpropane-1,3-diamine hydrochloride (14.3 mg, 0.075 mmol). After 31 hours total reaction time, deionized water (30 mL) was added to the reaction mixture. The product was extracted once with dichloromethane (60 mL). The dichloromethane extract was washed three times with 0.1 M hydrochloric acid (30, 60, 60 mL). The dichloromethane extract was then dried with sodium sulfate and filtered. The filtrate evaporated and product was placed under reduced pressure to dry. HPLC analysis was on C18 applying an acetonitrile gradient with 0.1% TFA; retention time was 11.5 minutes with >99% purity at 370 nm. No evidence for tert-butyl 2-aminoethyl(ethyl)carbamate or other ninhydrin positive impurities were shown by the TLC. The solids (158.4 mg, 84% yield) were dissolved in anhydrous methanol (10 mL) at 35° C. Once completely dissolved, 4M hydrochloric acid in 1,4-dioxane (20 mL) was added to the reaction solution. After one hour, the solvents were evaporated under reduced pressure. The dry product was suspended in anhydrous acetonitrile and distilled to dryness again. Yield: approximately 149 mg (theoretical yield). HPLC analysis was on C18 applying an acetonitrile gradient with 0.1% TFA; retention time was 2.5 minutes with >99% purity at 370 nm.

Synthesis of (Z)-(tert-butyl 2-(9-(hydroxymethyl)-9H-fluorene-2-carboxamido)ethylcarbamate) ethyl (2-(5-((5-fluoro-2-oxoindolin-3-ylidene)methyl)-2,4-dimethyl-1H-pyrrole-3-carboxamido)ethyl) carbamate (Compound 1a)

In a 2 L flask was added (Z)—N-(2-(ethylamino)ethyl)-5-((5-fluoro-2-oxoindolin-3-ylidene)methyl)-2,4-dimethyl-1H-pyrrole-3-carboxamide dihydrochloride (N-Des-ethyl sunitinib) (1.51 g, 3.41 mmol) with THF (750 mL) and 100 mM sodium phosphate buffer pH: 10.75 (500 mL). Saturated sodium chloride in water (250 mL) was added. After mixing, the THF layer was removed and dried with magnesium sulfate (75 g). The solution was filtered and evaporated to dryness. The yield for the free base form of compound 1 was 1.34 g. To the flask was added a solution of 2-(tert-butoxycarbonylamino)ethyl 9-(((1H-benzo[d][1,2,3]triazol-1-yloxy)carbonyloxy)methyl)-9H-fluorene-2-carboxylate (linker a)) (2.0 g, 3.68 mmol) in anhydrous THF (230 mL). Anhydrous THF (300 mL) was added to completely dissolve all materials. After approximately 18 hours, the reaction mixture was filtered. The filtrate was reacted with another portion of N-Desethyl Sunitinib free base (292.4 mg, 0.79 mmol, predissolved in 33 mM sodium phosphate buffer pH: 10.75—THF mixture). At four hours, the crude solution was evaporated to dryness. The product was triturated with anhydrous methanol (50, 30, 30 mL). The solids were washed anhydrous methanol (30 mL). The product was placed under reduced pressure to dry. Yield: 1.55 g (54.1%). HPLC analysis was on C18 applying an acetonitrile gradient with 0.1% TFA; retention time was 12.3 minutes with 98.5% purity at 370 nm. Analysis by LC-MS ([C$_{43}$H$_{47}$FN$_6$O$_7$]$^+$ expected M+H=779.9. found M+H=779.3).

Synthesis of (Z)—(N-(2-aminoethyl)-9-(hydroxymethyl)-9H-fluorene-2-carboxamide hydrochloride) ethyl(2-(5-((5-fluoro-2-oxoindolin-3-ylidene) methyl)-2,4-dimethyl-1H-pyrrole-3-carboxamido) ethyl)carbamate dihydrochloride (Compound 2a)

In round bottom flask was added (Z)-(tert-butyl 2-(9-(hydroxymethyl)-9H-fluorene-2-carboxamido)ethylcarbamate) ethyl(2-(5-((5-fluoro-2-oxoindolin-3-ylidene)methyl)-2,4-dimethyl-1H-pyrrole-3-carboxamido)ethyl)carbamate (Compound 1a) (801.4 mg, 1.029 mmol) in dioxane (140 mL). A solution of dioxane 4M HCl (140 mL) was added. After 1.5 hour, the reaction solvent was evaporated at reduced pressure. The solids were suspended with 1,4 dioxane (60 mL) and evaporated again. The solvent was evaporated to dryness. Yield: ~950 mg. HPLC analysis was on C18 applying an acetonitrile gradient with 0.1% TFA; retention time was 9.97 minutes with 96.7% purity at 370 nm. LC-MS data provided from another experiment performed under same conditions at smaller scale (5.6 mg). Analysis by LC-MS ([C$_{38}$H$_{39}$FN$_6$O$_5$]$^+$ expected M+H=679.3. found M+H=679.3).

Synthesis of (Z)-(9-(hydroxymethyl)-N-(2-(3-(mPEG 20,000)propanamido)ethyl)-9H-fluorene-2-carboxamide) ethyl(2-(5-((5-fluoro-2-oxoindolin-3-ylidene)methyl)-2,4-dimethyl-1H-pyrrole-3-carboxamido)ethyl)carbamate (Compound 3a)

In a 10 mL round bottom flask was added (Z)—(N-(2-aminoethyl)-9-(hydroxymethyl)-9H-fluorene-2-carboxamide hydrochloride) ethyl(2-(5-((5-fluoro-2-oxoindolin-3-ylidene)methyl)-2,4-dimethyl-1H-pyrrole-3-carboxamido)ethyl)carbamate dihydrochloride (Compound 2a) (4.83 mg, 6.42 μmol). The solids were dissolved in anhydrous tetrahydrofuran (0.4 mL) and 1,4 dioxane (0.2 mL). mPEG-SPA 20K (100.4 mg, 5.02 mop was added. Anhydrous acetonitrile (0.2 mL) was added to dissolve the PEG. After the PEG dissolved, triethylamine (5.2 μL, 0.037 mmol) was added. At 1 hour, the reaction solvent was evaporated at reduced pressure to a dry solid. The product was redissolved in anhydrous acetonitrile (0.5 mL) and precipitated by slow addition of anhydrous IPA (8 mL total). The product was washed with anhydrous IPA (50 mL) and diethyl ether. Residual solvent was evaporated at reduced pressure. Yield was 75 mg yellow powder (75% yield). HPLC analysis was on C18 applying an acetonitrile gradient with 0.1% TFA; retention times were desethyl sunitinib (compound 1) 2.5 minutes and product at 10.7 minutes. Buffer hydrolysis was performed to monitor the release of des-ethyl sunitinib (100 mM phosphate, 37° C.): 36 days at pH 7.5, 3.6 days at pH 8.5.

Synthesis of (Z)-(9-(hydroxymethyl)-N-(2-(3-(4arm-PEG 20,000)propanamido)ethyl)-9H-fluorene-2-carboxamide) ethyl(2-(5-((5-fluoro-2-oxoindolin-3-ylidene)methyl)-2,4-dimethyl-1H-pyrrole-3-carboxamido)ethyl)carbamate (Compound 4a)

In a round bottom flask was added 4armPEG-SCM 20K (2.80 g, 0.140 mmol) and anhydrous acetonitrile (40 mL). (Z)—(N-(2-aminoethyl)-9-(hydroxymethyl)-9H-fluorene-2-carboxamide hydrochloride) ethyl(2-(5-((5-fluoro-2-oxoindolin-3-ylidene)methyl)-2,4-dimethyl-1H-pyrrole-3-carboxamido)ethyl)carbamate dihydrochloride (Compound 2a) (647.2 mg, 0.672 mmol) was added. Diisopropylethylamine (0.838 mL, 4.80 mmol) was added. At 1 hour, more Diisopropylethylamine (0.172 mL, 0.985 mmol) was added. At 1 hour later, the reaction solution was added to anhydrous ethyl ether (700 mL, with BHT). The solids were washed with anhydrous isopropanol (500 mL, with BHT) and diethyl ether (with BHT). The product was redissolved in anhydrous dichloromethane (5 mL) and precipitated by slow addition of anhydrous IPA (200 mL, with BHT). The product was washed with anhydrous IPA (2×60 mL, with BHT) and diethyl ether (60 mL, with BHT). Residual solvent was evaporated at reduced pressure. Yield was 2.38 g yellow powder (~71% yield). HPLC analysis was on C18 applying an acetonitrile gradient with 0.1% TFA; retention time for product at 11.5 minutes with 97.6% purity at 370 nm. $^1$H-HMR (CD$_2$Cl$_2$): δ (ppm) 0.8-1.4 (12H, t, CH$_3$); 2.0-2.8 (24H, s, CH$_3$); 3.5 (H, s, PEG backbone); 4.0 (8H, s, —CH$_2$); 6.2-8.6 (AR, NH); 13.6 (4H, d, NH).

Example 2

Synthesis of 4-Aminoethyl-FMOC Linked PEG-Des-ethyl Sunitinib Conjugates

In this example, an approach reflected by the reaction scheme set forth in the schematic below was followed.

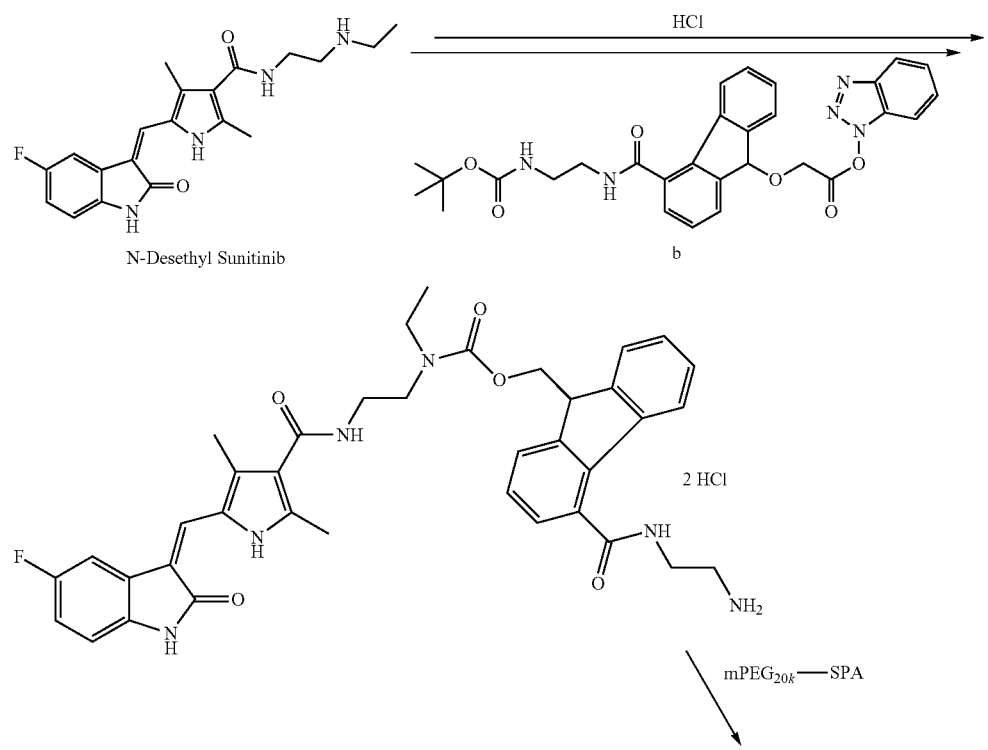

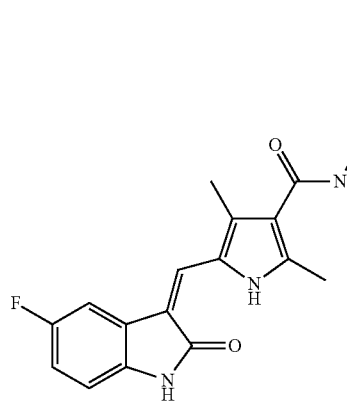
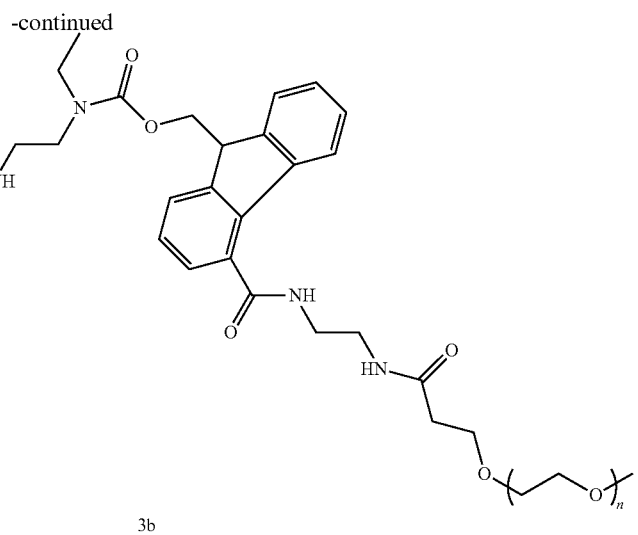

3b

In preparing the linker ("linker b"), the following reaction scheme set forth in the schematic below was followed.

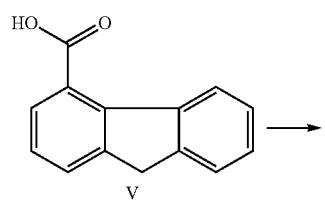

V

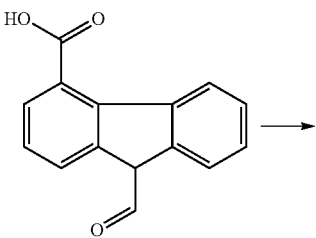

VI

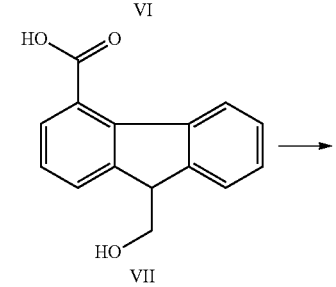

VII

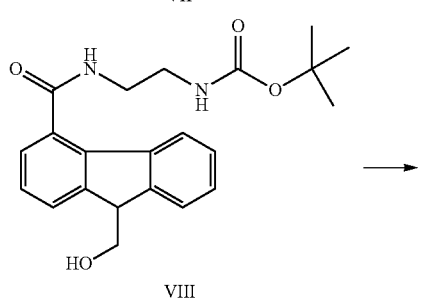

VIII

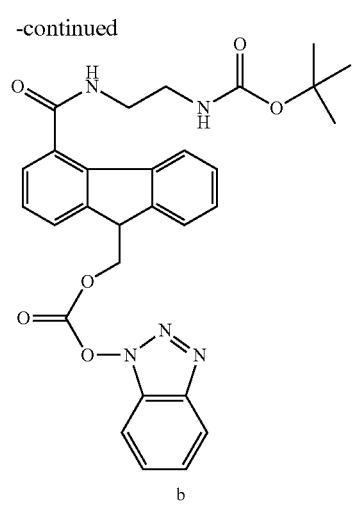

b

Synthesis of 9H-fluorene-4-carboxylic acid (Compound V)

Synthesis was conducted as described in Method A from Example 1, except 9-oxo-9H-fluorene-4-carboxylic acid (35.5 g, 158 mmol) was substituted for 9-oxo-9H-fluorene-2-carboxylic acid. Yield: 30.6 g (92%). HPLC analysis was on C18 applying an acetonitrile gradient with 0.1% TFA; retention time was 7.2 minutes with >99% purity at 300 nm. $^1$H-NMR (DMSO-$d_6$, 500 MHz): δ (ppm) 8.3-7.3 (Ar, 6H, 6-CH); 4.0 (s, 2H, —CH$_2$); 7.7 (d, 1H, —CH); 7.5 (m, 2H, 2-CH); 4.1 (t, 1H, —CH); 3.9, 3.7 (t, 2H, —CH$_2$).

Synthesis of 9-formyl-9H-fluorene-4-carboxylic acid (Compound VI)

Synthesis was conducted as described in Method B from Example 1, except substituting 9H-fluorene-4-carboxylic acid (10.17 g, 48.4 mmol) was substituted for 9H-fluorene-2-carboxylic acid. Yield: 15.5 g (approximately 100%). HPLC analysis was on C18 applying an acetonitrile gradient with 0.1% TFA; retention time was 3.5 minutes (split peak shows two forms of formyl) with >99% purity at 320 nm.

Synthesis of 9-(hydroxymethyl)-9,1-fluorene-4-carboxylic acid (Compound VII)

Synthesis was conducted as described in Method C from Example 1, except 9-formyl-9H-fluorene-4-carboxylic acid (11.5 g, 48.3 mol) was substituted for 9-formyl-9H-fluorene-2-carboxylic acid. Yield: 11.4 g (98%). HPLC analysis was on C18 applying an acetonitrile gradient with 0.1% TFA; retention time was 1.9 minutes with 99% purity at 300 nm. $^1$H-NMR (DMSO-$d_6$, 500 MHz): δ (ppm) 8.3-7.4 (Ar, 6H, 6-CH); 4.1 (t, 1H, —CH); 3.79, 3.82 (t, 2H, —CH$_2$).

Synthesis of tert-butyl 2-(9-(hydroxymethyl)-9H-fluorene-4-carboxamido)ethylcarbamate (Compound VIII)

Synthesis was conducted as described in Method D from Example 1, except 9-(hydroxymethyl)-9H-fluorene-4-carboxylic acid (3.15 g, 12.46 mol) was substituted for 9-(hydroxymethyl)-9H-fluorene-2-carboxylic acid. Yield: 4.8 g (77%). HPLC analysis was on C18 applying an acetonitrile gradient with 0.1% TFA; retention time was 2.7 minutes (also 3.4 minutes for different gradient) with 90% purity at 280 nm. $^1$H-NMR (DMSO-$d_6$, 500 MHz): δ (ppm) 8.5 (t, 1H, —NH); 7.8-7.3 (Ar, 7H, 7-CH); 6.9 (t, 1H, —NH); 5.1 (t, 1H, —OH) 4.1 (m, 2H, —CH$_2$); 4.0 (m, 1H, —CH); 3.4 (t, 2H, —CH$_2$); 3.2 (t, 2H, —CH$_2$); 1.4 (s, 9H, —(CH$_3$)$_3$).

Synthesis of tert-butyl 2-(9-(((1H-benzo[d][1,2,3]triazol-1-yloxy)carbonyloxy)methyl)-9H-fluorene-4-carboxamido)ethylcarbamate (Linker b)

To a 50 mL round bottom flask was added tert-butyl 2-(9-(hydroxymethyl)-9H-fluorene-4-carboxamido)ethylcarbamate (0.2320 g, 0.607 mmol) in 10 mL anhydrous acetonitrile and 1,4 dioxane (3 mL). Di(1H-benzo[d][1,2,3]triazol-1-yl)carbonate, 66.7% weight (119 mg, 0.268 mmol) was added to the reaction solution with anhydrous acetonitrile (1.6 mL). Anhydrous pyridine (150 μL, 1.855 mmol) was added. After 2.5 hours, more di(1H benzo[d][1,2,3]triazol-1-yl)carbonate, 66.7% weight (85.1 mg, 0.192 mmol) was added. Approximately 3 hours later, the reaction solution was not isolated and stored at −20° C. HPLC analysis was on C18 applying an acetonitrile gradient with 0.1% TFA; retention time was 4.4 minutes with a purity of 85% at 280 nm.

Synthesis of (Z)-(tert-butyl 2-(9-(hydroxymethyl)-9H-fluorene-4-carboxamido)ethylcarbamate) ethyl (2-(5-((5-fluoro-2-oxoindolin-3-ylidene)methyl)-2,4-dimethyl-1H-pyrrole-3-carboxamido)ethyl) carbamate To a 50 mL round bottom flask, N-Des-ethyl Sunitinib (56.4 mg, 0.127 mmol) and linker b (3.287 mL of a 283.8 mg/14.6 mL acetonitrile-dioxane solution, 63.89 mg, 0.127 mmol) were added. Triethylamine (82 μL, 0.588 mmol) was added. The reaction mixture was diluted with anhydrous tetrahydrofuran (THF) (5 mL). One hour later, the reaction mixture was cooled to −20° C. The next day, the solvents were evaporated and the dry material was dissolved in tetrahydrofuran (27 mL) and 100 mM phosphate buffer pH 8.5 (9 mL). The solution was clear and orange in color. To the solution, linker b (4.5 mL of a 283.8 mg/14.6 mL acetonitrile-dioxane solution, 84.47 mg, 0.161 mmol) was added. The temperature of the reaction solution was increased to 37° C. After 2.5 hours, saturated sodium chloride (80 mL) was added to the reaction mixture. The THF layer was removed and dried with sodium sulfate. The solution was filtered and the filtrate was evaporated. The crude product was partially dissolved in anhydrous acetonitrile (8 mL) and stored at −20° C. for two days. The supernatant was removed and the remaining solids were triturated with cold anhydrous acetonitrile (3×3 mL). The product was evaporated to dryness. Yield: ~60 mg (65% orange solids). HPLC analysis was on C18 applying an acetonitrile gradient with 0.1% TFA; retention time was 5.4 minutes with a purity of 95% at 370 nm.

Synthesis of (Z)-(4-(2-aminoethylcarbamoyl)-9H-fluoren-9-yl)methyl ethyl(2-(5-((5-fluoro-2-oxoindolin-3-ylidene)methyl)-2,4-dimethyl-1H-pyrrole-3-carboxamido)ethyl)carbamate dihydrochloride (Compound 2b)

In a 10 mL round bottom flask was added (Z)-(tert-butyl 2-(9-(hydroxymethyl)-9H-fluorene-4-carboxamido)ethylcarbamate) ethyl(2-(5-((5-fluoro-2-oxoindolin-3-ylidene)methyl)-2,4-dimethyl-1H-pyrrole-3-carboxamido)ethyl)carbamate (60 mg, 0.077 mmol) in dioxane (5.0 mL). A solution of dioxane 4M NCl (10 mL) was added. After 1.5 hours, the reaction solvent was evaporated at reduced pressure. Theoretical yield: ~63.5 mg. HPLC analysis was on C18 applying an acetonitrile gradient with 0.1% TFA; retention time was 3.5 minutes with a purity of 95% at 370 nm. Analysis by LC-MS ($[C_{38}H_{39}FN_6O_5]^+$ expected M+H=679.3. found M+H=679.3).

Synthesis of (Z)-(9-(hydroxymethyl)-N-(2-(3-(mPEG 20,000)propanamido)ethyl)-9H-fluorene-4-carboxamide) ethyl(2-(5-((5-fluoro-2-oxoindolin-3-ylidene)methyl)-2,4-dimethyl-1H-pyrrole-3-carboxamido)ethyl)carbamate (Compound 3b)

In a 10 mL round bottom flask was added Compound 2b (9.6 mg, 0.013 mmol). The solids were suspended in anhydrous acetonitrile (0.37 mL) and 1,4 dioxane (0.37 mL). mPEG-SPA 20K (181.3 mg, 9.07 mop was added. After the PEG dissolved, triethylamine (9.24 μL, 0.066 mmol) was added. At one hour, the product was precipitated by slow addition of anhydrous IPA (10 mL). The solid was washed with anhydrous IPA (25-30 mL) and then washed with diethyl ether. Residual solvent was evaporated at reduced pressure. Yield was ~120 mg yellow powder. The product was transferred to a 50 mL round bottom flask. More Compound 2b (6.9 mg, 9.18 μmol) was added. Anhydrous acetonitrile (0.25 mL) and anhydrous 1,4 dioxane (0.25 mL) and anhydrous pyridine (2.2 μL, 0.027 mmol) were added. The reagents never fully dissolved, therefore triethylamine (6 μL, 0.043 mmol) was added. The solution was a clear orange color. After 45 minutes, the product was precipitated by slow addition of anhydrous IPA (~10 mL). The solid was washed with anhydrous IPA (~25-30 mL) and then washed with diethyl ether. Residual solvent was evaporated at reduced pressure. Yield was ~68 mg (57%) yellow powder. HPLC analysis was on C18 applying an acetonitrile gradient with 0.1% TFA; retention times were desethyl sunitinib (compound 1) 2.5 min and product at 10.7 min. Buffer hydrolysis was performed to monitor the release of des-ethyl sunitinib (100 mM phosphate, 37° C.): 22 days at pH 7.5, 1.4 days at pH 8.5.

Example 3

Synthesis of mPEG-BA-Des-ethyl Sunitinib (COMPOUND 5)

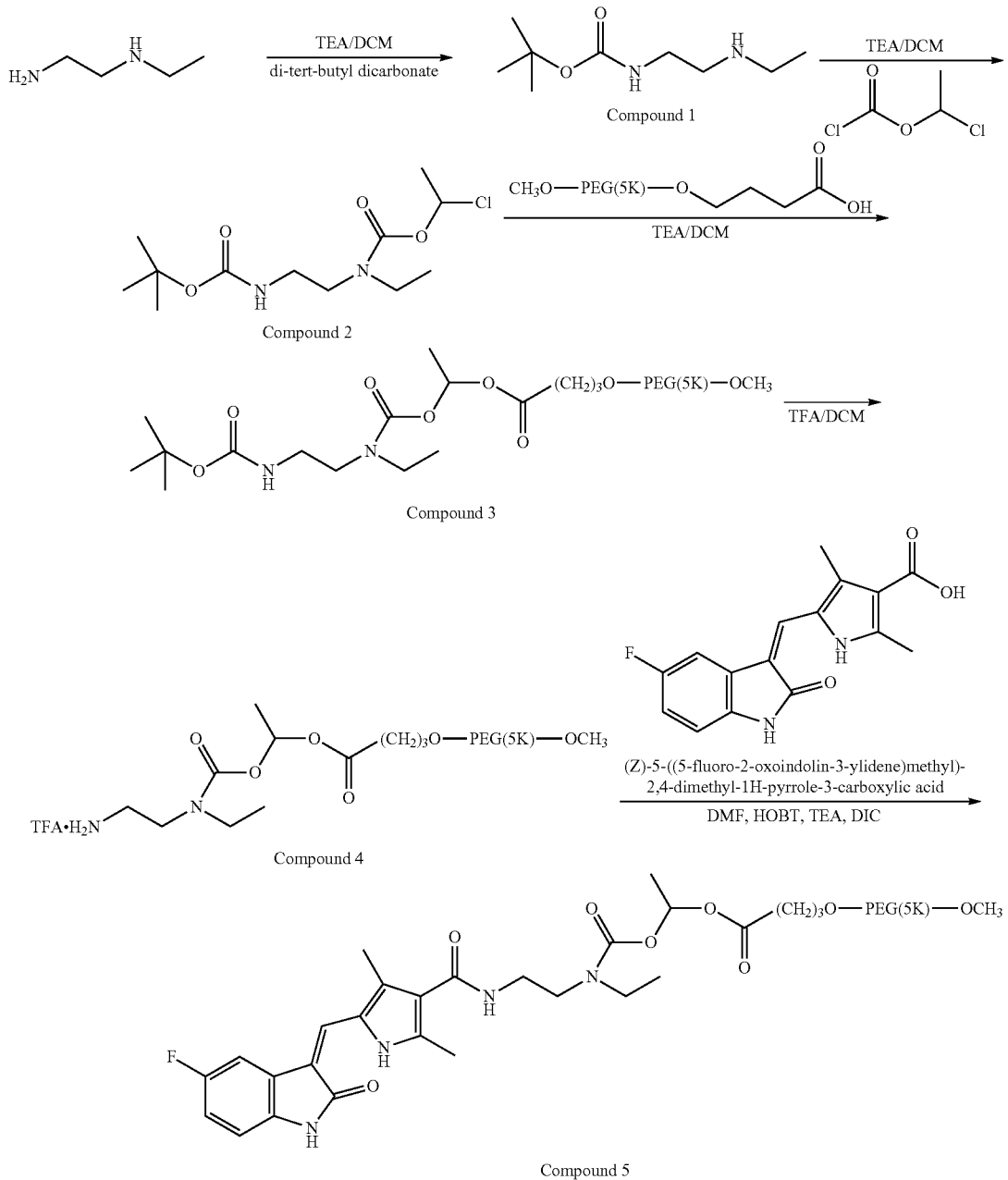

Synthesis of tert-butyl 2-(ethylamino)ethylcarbamate (Compound 1)

In a round bottom flask, N-ethylethylenediamine (8.82 g) was dissolved in 200 ml of anhydrous THF, the solution was cooled to 0-5° C. and di-tert-butyl dicarbonate (6.54 g) dissolved in 60 ml of THF was added during one hour. The mixture was stirred overnight at room temperature. Next, the solvent was distilled off, the residue was dissolved in saturated NaCl solution (60 ml) and the product was extracted with dichloromethane (3×60 ml). The extract was washed with a saturated NaCl solution (60 ml) and dried with anhydrous $MgSO_4$. Next, the solvent was distilled off under reduced pressure and the obtained product was recrystallized from hexane giving 3.2 g of the desired product.

Synthesis of 1-chloroethyl ethyl(2-(Boc-amino)ethyl)carbamate (Compound 2)

In a round bottom flask, Compound 1 (t-Boc-$NHCH_2CH_2NHCH_2CH_3$; 1.50 g) was dissolved in anhydrous dichloromethane (60 ml) and the solution was cooled to 0-5° C. Triethylamine (TEA, 1.2 ml) was added followed by 1-chloroethyl chloroformate (0.79 ml) and the mixture was stirred for three hours at room temperature. Next, the mixture was washed with 0.1M solution of $NaH_2PO_4$ (50 ml and 30 ml) and dried with anhydrous $MgSO_4$. Then, the solvent was distilled under reduced pressure giving 2.15 g of the desired product.

Synthesis of 1-(ethyl(2-(Boc-amino)ethyl)carbamoyloxy)ethyl 4-(mPEG 5,000)butanoate (Compound 3)

In a round bottom flask, Compound 2 (0.50 g) was dissolved in 10 ml of anhydrous dichloromethane (10 ml) and methoxy-poly(ethylene glycol)-butanoic acid MW 5,000 (1.7 g) was added followed by TEA (0.142 ml). The reaction mixture was stirred overnight at room temperature under nitrogen atmosphere. Part of the solvent was distilled off under reduced pressure and the product was precipitated with the mixture of isopropyl alcohol and ethyl ether and purified by ion exchange chromatography giving 0.84 g of the desired product having 99.0% purity determined by HPLC.

Synthesis of 1-((2-aminoethyl)(ethyl)carbamoyloxy)ethyl 4-(mPEG 5,000)butanoate trifluoroacetate (Compound 4)

In a round bottom flask, Compound 3 (0.84 g) was dissolved in the mixture of trifluoroacetic acid and dichloromethane (1:1, 20 ml) and the solution was stirred for one hour at room temperature. The solvents were distilled off under reduced pressure and the obtained product was precipitated with ethyl ether (30 ml) giving 0.79 g of the desired product.

Synthesis of (Z)-1-(ethyl(2-(5-((5-fluoro-2-oxoindolin-3-ylidene)methyl)-2,4-dimethyl-1H-pyrrole-3-carboxamido)ethyl)carbamoyloxy)ethyl 4-(mPEG 5,000)butanoate (Compound 5)

In a round bottom flask, (Z)-5-((5-fluoro-2-oxoindolin-3-ylidene)methyl)-2,4-dimethyl-1H-pyrrole-3-carboxylic acid (0.018 g) and 1-hydroxybenzotriazole (HOBT, 0.081 g) were dissolved in 2 ml of anhydrous DMF. TEA (0.022 ml) was added, followed by N,N-diisopropylcarbodiimide (DIC, 0.062 ml). Next Compound 4 (0.2 g) dissolved 1 ml of anhydrous dichloromethane was added and the mixture was stirred overnight at room temperature under nitrogen atmosphere. The solvents were distilled off under reduced pressure and residue was precipitated with the mixture of isopropyl alcohol and ethyl ether (3:7, 30 ml) giving after drying the desired product (0.175 g) as a white solid having ~95% purity determined by HPLC.

Example 4

Synthesis of mPEG-Gly-Des-ethyl Sunitinib (Compound 8)

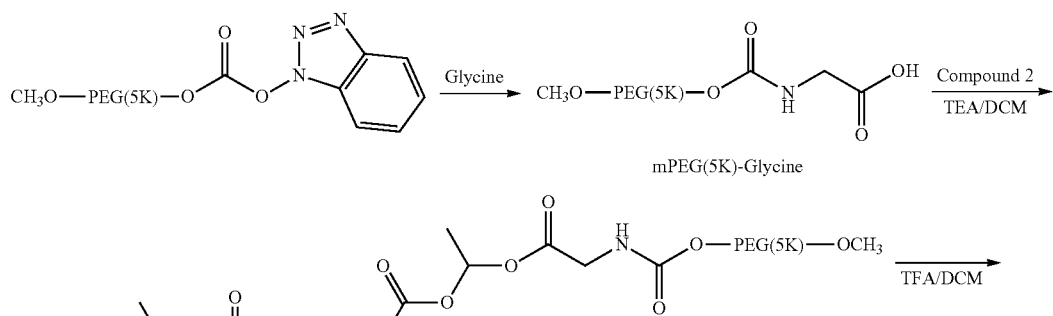

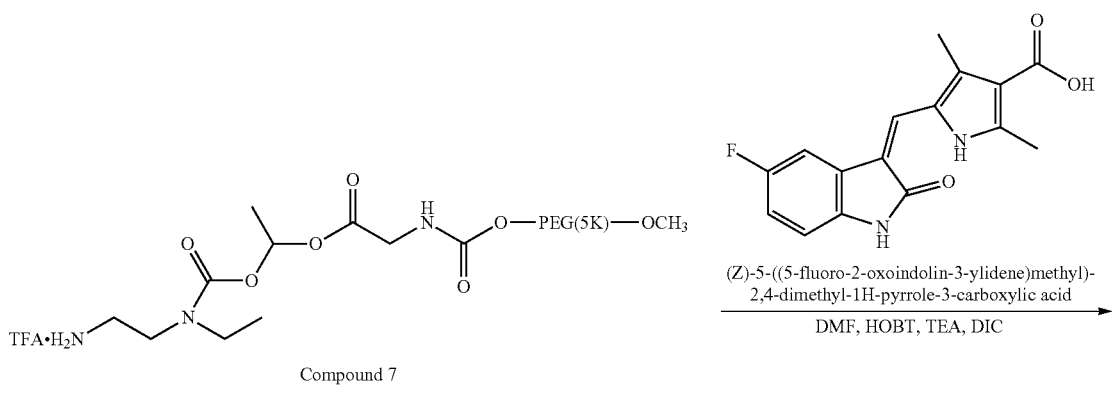

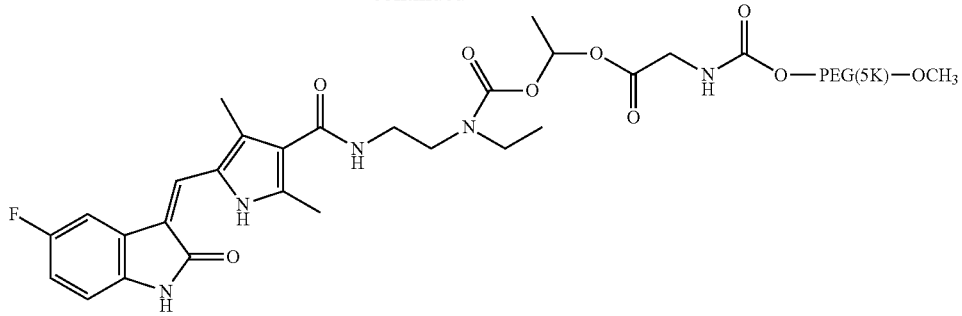

Compound 8

Synthesis of mPEG(5K)-Glycine

Methoxy(polyethylene glycol)-benzotriazolyl carbonate, MW 5,000 (5.0 g) was added slowly to the solution of glycine (0.75 g) dissolved in 50 ml of 0.1N boric buffer (pH 9.0). The mixture was stirred for three hours at room temperature. Next, the pH was adjusted to 2.0 with 5% $H_3PO_4$ and the product was extracted by dichloromethane. The extract was dried ($MgSO_4$) and the solvent was distilled under reduced pressure giving methoxy(polyethylene glycol)-glycine ("mPEG(5K)-Glycine") (4.3 g) having 99.3% purity determined by HPLC.

Synthesis of 1-(ethyl(2-(Boc-amino)ethyl)carbamoyloxy)ethyl 2-((mPEG 5,000)carbonylamino)acetate (Compound 6)

In a round bottom flask, Compound 2 (prepared in accordance with the procedure set forth in Example 3) (0.4 g) was dissolved in anhydrous dichloromethane (5 ml). Next, mPEG(5K)-Glycine (1.35 g) dissolved in anhydrous dichloromethane (10 ml) was added followed by TEA (0.12 ml). The mixture was stirred for two days at room temperature under nitrogen atmosphere. The solvent was distilled off under reduced pressure and the product was precipitated with isopropyl alcohol (80 ml). The precipitate was collected through vacuum filtration and dried under vacuum giving the desired product (1.31 g) having 96% purity determined by HPLC.

Synthesis of 1-((2-aminoethyl)(ethyl)carbamoyloxy)ethyl 2-((mPEG 5,000)carbonylamino)acetate trifluoroacetate (Compound 7)

In a round bottom flask, Compound 6 (1.3 g) was dissolved in the mixture of trifluoroacetic acid and dichloromethane (1:1, 20 ml) and the solution was stirred for one hour at room temperature. The solvents were distilled off under reduced pressure and the resulting product was precipitated with ethyl ether (100 ml). Yield: 1.20 g.

Synthesis of (Z)-1-(ethyl(2-(5-((5-fluoro-2-oxoindolin-3-ylidene)methyl)-2,4-dimethyl-1H-pyrrole-3-carboxamido)ethyl)carbamoyloxy)ethyl 2-((mPEG 5,000)carbonylamino)acetate (Compound 8)

In a round bottom flask, (Z)-5-(5-fluoro-2-oxoindolin-3-ylidene)methyl)-2,4-dimethyl-1H-pyrrole-3-carboxylic acid (0.018 g) and HOBT (0.008 g) were dissolved in 2 ml of anhydrous DMF. Then, 1-Ethyl-3-(3-dimethylaminopropyl) carbodiimide (EDC, 0.038 g) was added followed by Compound 7 (0.2 g), anhydrous dichloromethane (2 ml), and TEA (0.017 ml). The reaction mixture was stirred overnight at room temperature under nitrogen atmosphere. The solvent were distilled under reduced pressure and the product was precipitated with ethyl ether (30 ml), redissolved in dichloromethane (5 ml) and precipitated with isopropyl alcohol (50 ml). The precipitate was filtered off and dried under reduced pressure giving the desired product ("mPEG-Gly-Des-ethyl Sunitinib") (0.125 g).

Example 5

Synthesis of mPEG-Leu-Des-ethyl Sunitinib (Compound 9)

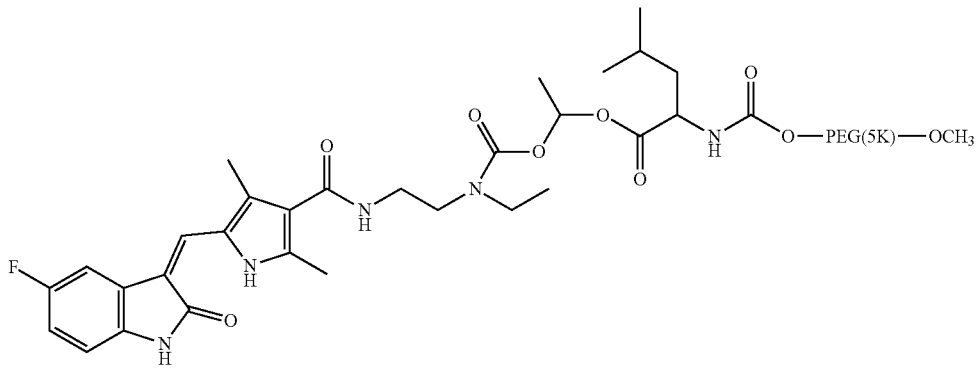

Synthesis of (Z)-1-(ethyl(2-(5-((5-fluoro-2-oxoindo-lin-3-ylidene)methyl)-2,4-dimethyl-1H-pyrrole-3-carboxamido)ethyl)carbamoyloxy)ethyl 2-((mPEG 5,000)carbonylamino)-4-methylpentanoate (Compound 9)

mPEG-Leu-Des-ethyl sunitinib was prepared in a manner similar to the approach used in Example 4 except leucine was used in place of glycine.

Example 6

Synthesis of mPEG-Val-Des-ethyl Sunitinib (Compound 10)

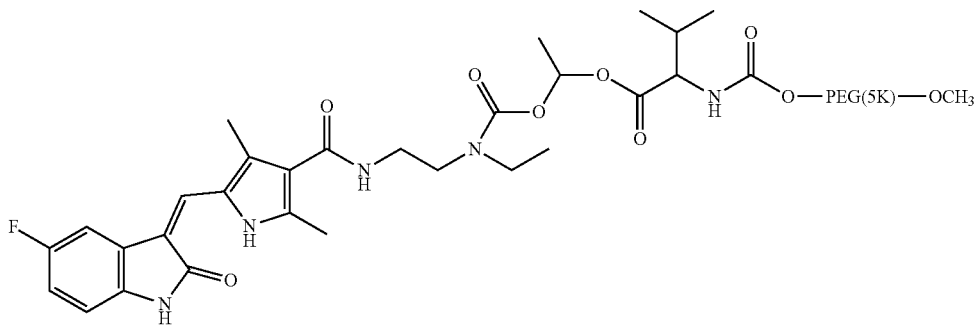

Compound 10

Synthesis of (Z)-1-(ethyl(2-(5-((5-fluoro-2-oxoindo-lin-3-ylidene)methyl)-2,4-dimethyl-1H-pyrrole-3-carboxamido)ethyl)carbamoyloxy)ethyl 2-((mPEG 5,000)carbonylamino)-3-methylbutanoate (Compound 10)

mPEG-Val-Des-ethyl sunitinib was prepared in a manner similar to the approach used in Example 4 except valine was used in place of glycine.

Example 7

Study of Release of Des-ethyl Sunitinib from PEG Conjugates

Figure 2:
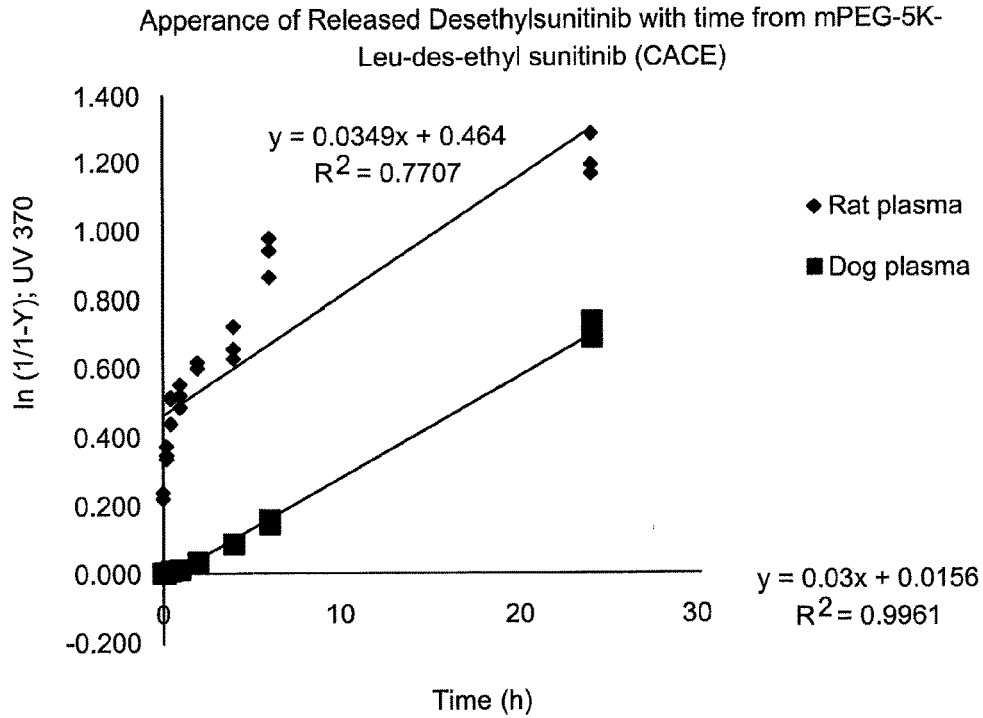
FIG. 2 is a plot of the appearance of released des-ethyl sunitinib from a conjugate of the invention [mPEG-5K-Leu-des-ethyl sunitinib (CACE)], as more fully described in Example 7.

Experiments were carried out to measure drug release from the polymer conjugates. Data are shown in Tabular form in Table 3. A typical plot of the data showing the decay of the polymer conjugate (FIG. 1) and the build-up of drug with time (FIG. 2) are included.

TABLE 3

Plasma Hydrolysis Rates

| Conjugate Name | Rat Plasma | Dog Plasma | Phosphate pH 8.5 | Phosphate pH 7.5 |
|---|---|---|---|---|
| mPEG-5K-BA-Des-ethyl Sunitinib (CACE) (Example 3, Compound 5) | ~4.6 h | ~24 h | | 17 d (25° C.) |
| mPEG-5K-Gly-Des-ethyl Sunitinib (CACE) (Example 4, Compound 8) | (~16-19 h) | (~19-22 h) | | 1.2 d (25° C.) |
| mPEG-5K-Leu-Des-ethyl Sunitinib (CACE) (Example 5, Compound 9) | (~16-20 h) | (~19-24 h) | | 7 d (25° C.) |
| mPEG-5K-Val-Des-ethyl Sunitinib (CACE) (Example 6, Compound 10) | (~4-13 h) | (~73-82 h) | | 41 d (25° C.) |

TABLE 3-continued

| | | Plasma Hydrolysis Rates | | |
|---|---|---|---|---|
| Conjugate Name | Rat Plasma | Dog Plasma | Phosphate pH 8.5 | Phosphate pH 7.5 |
| mPEG-20K-Des-ethyl Sunitinib-3a (FMOC) (Example 1, Compound 3a) | ~19 h | ~19 h | 3.6 d | 30 d |
| mPEG-20K-Des-ethyl Sunitinib-3b (FMOC) (Example 2, Compound 3b) | ~5 h | ~10-15 h | 1.4 d | 25 d |

NOTE:
Italic text indicates poor data fit to first order plot and half lives calculated at 37° C. Unless otherwise indicated, incubations were performed at 37° C.

Example 8

In Vivo Release Kinetics and Tumor Accumulation

Eight to twelve week old female NCr nu/nu mice with were injected subcutaneously with $5\times10^6$ HCT116 colon-rectal cancer cells in 0% Matrigel in a flank. Upon reaching a tumor size of 500 mm³, mice were treated with either 40 mg/kg sunitinib NKT11012 (oral) or 40 mg/kg des-ethyl sunitinib equivalent of examples 1 (compound 4a), example 8 (compound 12), example 9 and example 10 (IV via tail vein). Blood and tumor samples were collected at 6, 12, 24, 48, 72, 120 and 168 hours post dose to determine plasma and tumor des-ethyl sunitinib concentrations.

Figure 3:
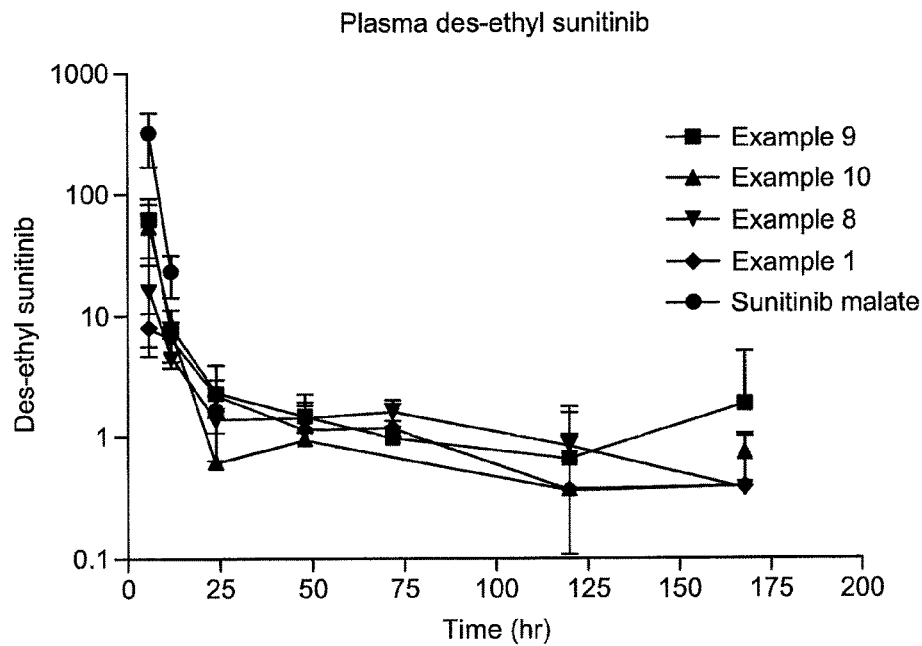
FIG. 3 and FIG. 4 are plots of the mean des-ethyl sunitinib concentration/time curve for compounds of interests in plasma and tumor, respectively, as further described in Example 8.
Figure 4:
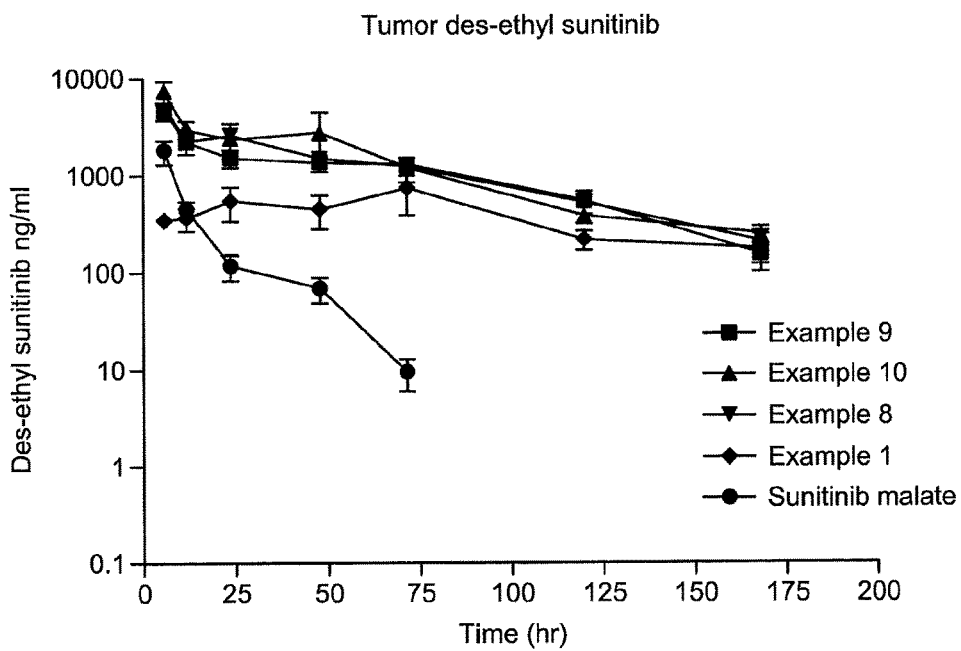

Data is provided in FIG. 3, where mean the plasma concentration of des-ethyl sunitinib following administration of a compound of interest is provided for a series of time points, Turning to FIG. 4, tumor concentration of des-ethyl sunitinib following administration of a compound of interest is provided for a series of time points.

Example 9

Synthesis of 2-mPEG$_3$-7-Aminoethyl-FMOC Linked PEG-Des-Ethyl Sunitinib Conjugates

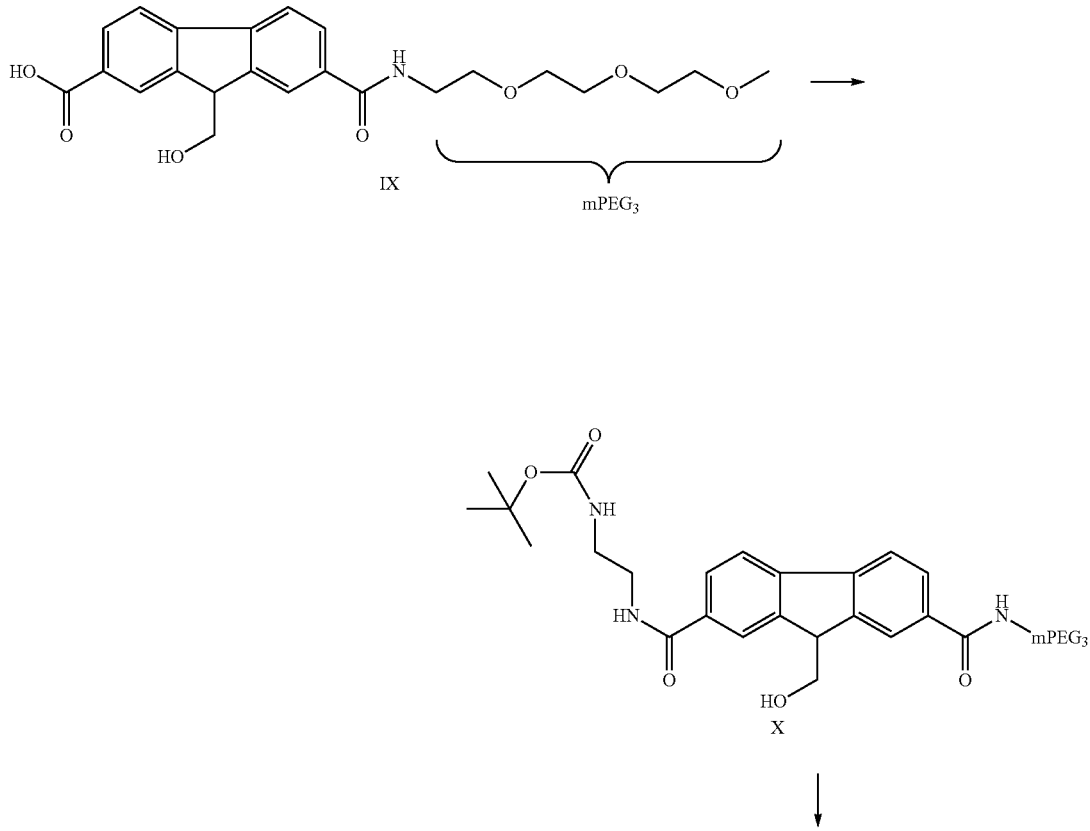

-continued

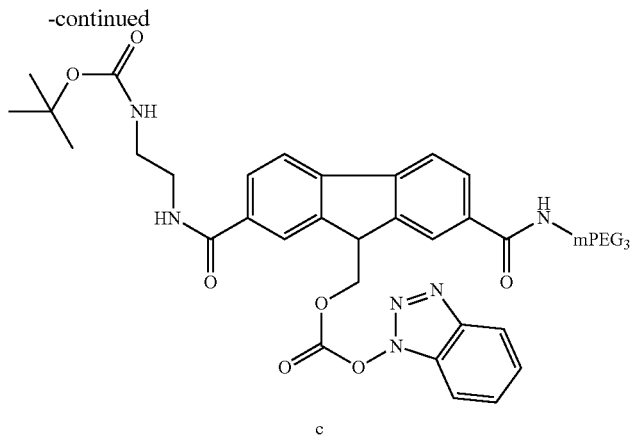

c

Synthesis of 9-(hydroxymethyl)-7-(2-(2-(2-methoxyethoxy)ethoxy)ethylcarbamoyl)-9,1-fluorene-2-carboxylic acid (Compound IX)

In a 100 mL round bottom flask, 2-(2-(2-methoxyethoxy)ethoxy)ethanamine (mPEG$_3$-NH$_2$, 701 mg, 4.29 mmol) was added with anhydrous dichloromethane (12.5 mL) to give a clear solution. A solution of 9-(hydroxymethyl)-9H-fluorene-2,7-dicarboxylic acid (500.4 mg, 1.760 mmol) and 1H-benzo[d][1,2,3]triazol-1-ol (500.4 mg, 3.70 mmol) in anhydrous dimethylformamide (12.5 mL) was added. N,N'-dicyclohexylcarbodiimide (389.1 mg, 1.886 mmol) was added to reaction solution. At 18 hours the solution was filtered and evaporated to an oil. Methanol (10 mL) was added to dissolve the oil. The solution was filtered. The filtrate was evaporated to oil under reduced pressure. The crude product was purified on a Biotage Flash silica column with a dichloromethane/methanol gradient program. Product fractions were combined and evaporated at reduced pressure. Yield: 400 mg (42%). HPLC analysis employed a C18 column using an acetonitrile gradient with 0.1% TFA; retention time was 5.77 minutes with a purity of 91% at 320 nm. Analysis by LC-MS ([$C_{23}H_{27}NO_7$]$^+$ expected M+H=430.2. found M+H=430.2). $^1$H-NMR (DMSO-d$_6$, 500 MHz): δ (ppm) 8.6 (t, 1H, —NH); 8.3-7.9 (Ar, 6H, 6-CH); 5.1 (t, 1H, —OH); 4.1 (t, 1H, —CH); 3.9-3.8 (t, 2H, —CH$_2$). The product contained HOBT that was observed in the NMR spectrum and HPLC chromatogram.

Synthesis of tert-butyl 2-(9-(hydroxymethyl)-7-(2-(2-(2-methoxyethoxy)ethoxy)ethylcarbamoyl)-9H-fluorene-2-carboxamido)ethylcarbamate (Compound X)

In a round bottom flask, 9-(hydroxymethyl)-7-(2-(2-(2-methoxyethoxy)ethoxy)ethylcarbamoyl)-9H-fluorene-2-carboxylic acid (Compound IX) (359.0 mg, 0.702 mmol) was dissolved in anhydrous dimethylformamide (4 mL). To the solution tert-butyl 2-aminoethylcarbamate (168.5 mg, 1.052 mmol) and N1-((ethylimino)methylene)-N3,N3-dimethylpropane-1,3-diamine hydrochloride (252.6 mg, 1.318 mmol) were added. Anhydrous dimethylformamide (1 mL) was used to rinse wall of round bottom flask. At 24 hours, the solution was stored at −20° C. Fifteen hours later, the reaction solution was warmed to room temperature and dichloromethane (125 mL) was added. The solution was washed with 0.1M HCl (3×125 mL) and a final wash with 5% sodium chloride (125 mL). The dichloromethane extract was dried with sodium sulfate, filtered, and evaporated to dryness under reduced pressure. Yield: 323 mg (80%) (a stock solution was prepared by dissolving 323 mg in anhydrous acetonitrile (5.15 mL) and anhydrous 1,4-dioxane (3.15 mL)—concentration: 38.92 mg/mL solution). HPLC analysis employed a C18 column using an acetonitrile gradient with 0.1% TFA; retention time was 3.0 minutes with a purity of 90% at 320 nm. Analysis by LC-MS ([$C_{30}H_{41}N_3O_8$]$^+$ expected M+H=572.3. found M+H=572.3). $^1$H-NMR (CD$_2$Cl$_2$, 500 MHz): δ (ppm) 8.1-7.9 (Ar, 6H, 6-CH); 7.3 (s, 1H, —NH); 7.0 (5.1 s, 1H, —NH); 4.2 (m, 2H, —CH$_2$); 4.0 (t, 1H, —CH); 3.7-3.6 (m, 10H, —CH$_2$ from PEG); 3.55 (t, 2H, —CH$_2$); 3.5 (t, 2H, —CH$_2$); 3.4 (t, 2H, —CH$_2$), 3.2 (s, 3H, —OCH$_3$), 1.4 (s, 9H, —(CH$_3$)$_3$).

Synthesis of tert-butyl 2-(9-(((1H-benzo[d][1,2,3]triazol-1-yloxy)carbonyloxy)methyl)-7-(2-(2-(2-methoxyethoxy)ethoxy)ethylcarbamoyl)-9H-fluorene-2-carboxamido)ethylcarbamate (linker c)

Tert-butyl 2-(9-(hydroxymethyl)-7-(2-(2-(2-methoxyethoxy)ethoxy)ethylcarbamoyl)-9H-fluorene-2-carboxamido)ethylcarbamate (X) (4.5 mL of 38.92 mg/mL solution in acetonitrile:dioxane, 175.1 mg, 0.306 mmol) was added to a round bottom flask. To the solution, Di(1H-benzo[d][1,2,3]triazol-1-yl)carbonate, 66.7% by weight (175 mg, 0.394 mmol) and anhydrous pyridine (78 µL, 0.964 mmol) were added. After four hours and two more additions of di(1H-benzo[d][1,2,3]triazol-1-yl)carbonate, 66.7% by weight (40 mg, 45 mg; 0.090 mmol, 0.101 mmol), the reaction solution was evaporated to dryness under reduced pressure. HPLC analysis employed a C18 column using an acetonitrile gradient with 0.1% TFA; retention time was 3.6 minutes with a purity of approximately 75% at 320 nm.

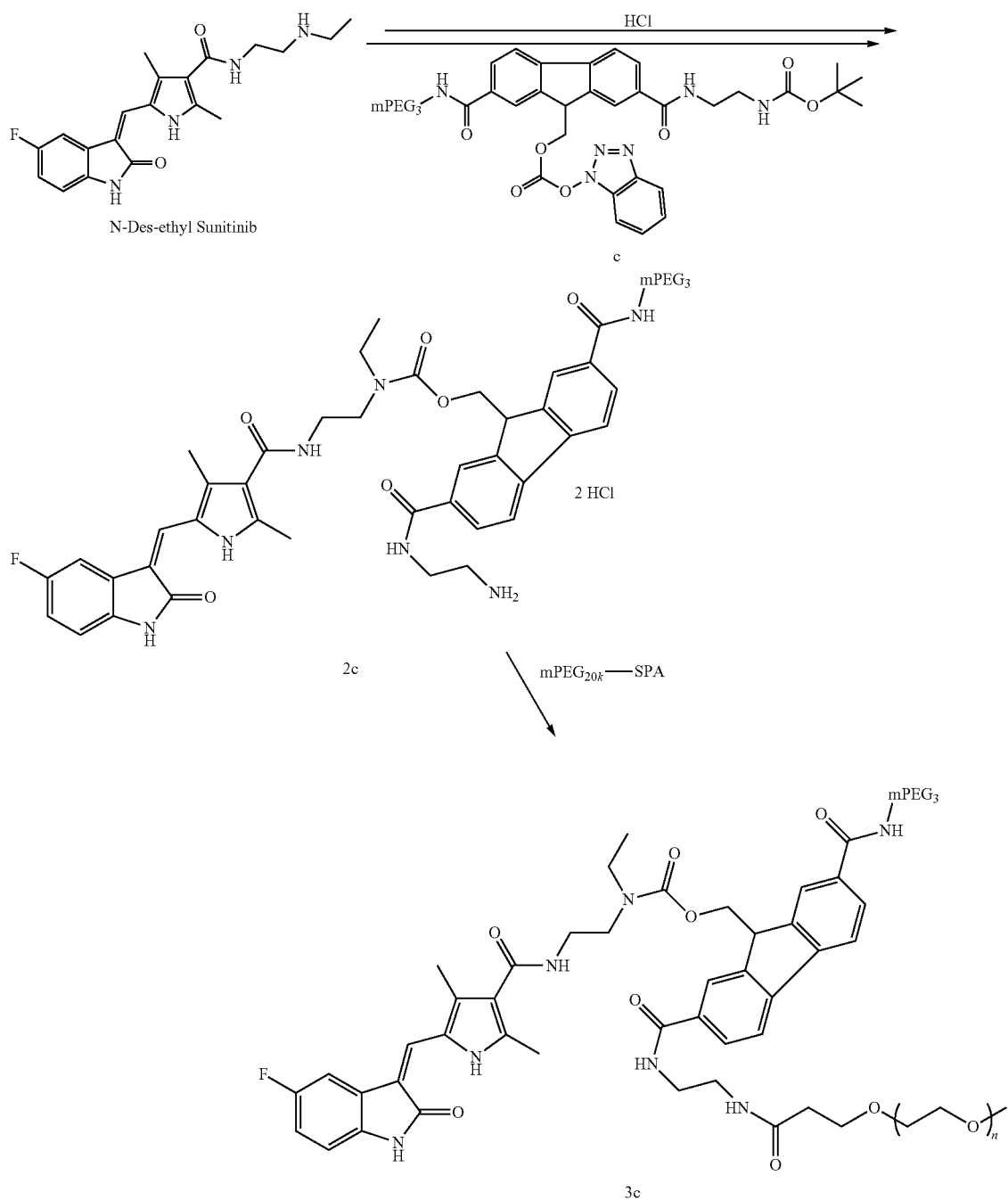

Synthesis of (Z)-(tert-butyl 2-(9-(hydroxymethyl)-7-(2-(2-(2-methoxyethoxy)ethoxy)ethylcarbamoyl)-9H-fluorene-2-carboxamido)ethylcarbamate) ethyl (2-(5-((5-fluoro-2-oxoindolin-3-ylidene)methyl)-2,4-dimethyl-1H-pyrrole-3-carboxamido)ethyl) carbamate (Compound 1c)

In a 100 mL round bottom flask, linker c (224 mg, 0.232 mmol) was dissolved in anhydrous tetrahydrofuran (10 mL). To the solution, 100 mM phosphate buffer pH: 8.5 (3.5 mL) and N-des-ethyl sunitinib (109.85 mg, 0.248 mmol) were added. The reaction temperature was increased to 42° C.). At 3.5 hours, saturated sodium chloride was added to the reaction mixture. The tetrahydrofuran (THF) layer was collected. Tetrahydrofuran (THF) was added to the aqueous extract again to recover more product. The collected THF layers were dried with anhydrous sodium sulfate. The solution was filtered and evaporated to dryness. Water was present in the flask after evaporation and was removed with pipette. The final product was further purified with a methanol tituration and placed under reduced pressure. Yield: 30 mg (13%). HPLC analysis employed a C18 column using an acetonitrile gradient with 0.1% TFA; retention time was 4.5 minutes with a purity of 97% at 370 nm. Analysis by LC-MS was performed on a stored sample (−20° C. for 20 hours in methanol) $[C_{51}H_{62}FN_7O_H]^+$ expected M+H=968.5. found M+H=968.4.

Synthesis of (Z)—(N2-(2-aminoethyl)-9-(hydroxymethyl)-N7-(2-(2-(2-methoxyethoxy)ethoxy)ethyl)-9H-fluorene-2,7-dicarboxamide hydrochloride) ethyl(2-(5-((5-fluoro-2-oxoindolin-3-ylidene)methyl)-2,4-dimethyl-1H-pyrrole-3-carboxamido)ethyl)carbamate (Compound 2c)

In a round bottom flask, Compound 1c (27.8 mg, 0.029 mmol) was suspended in anhydrous 1,4 dioxane (2.5 mL) and dioxane 4M HCl (2.5 mL). Anhydrous methanol (1.0 mL) was added to dissolve solids and give a clear solution. After one hour the reaction solvent was evaporated at reduced pressure. The solids were suspended with 1,4 dioxane and the solvent was evaporated under reduced pressure. Yield: approximately 27 mg (theoretical yield). HPLC analysis employed a C18 column using an acetonitrile gradient with 0.1% TFA; retention time was 3.2 minutes with a purity of 97% at 370 nm.

Synthesis of (Z)-(9-(hydroxymethyl)-N2-(2-(2-(2-methoxyethoxy)ethoxy)ethyl)-N7-(2-(3-(2-(mPEG 20,000))propanamido)ethyl)-9H-fluorene-2,7-dicarboxamide) ethyl(2-(5-((5-fluoro-2-oxoindolin-3-ylidene)methyl)-2,4-dimethyl-M-pyrrole-3-carboxamido)ethyl)carbamate (Compound 3c)

In a 10 mL round bottom flask was Compound 2c (7.4 mg, 7.69 mop was suspended in anhydrous dioxane (0.5 mL) and anhydrous acetonitrile (0.5 mL). mPEG-SPA 20K (100.0 mg, 5.0 mot) was added. After the PEG dissolved, triethylamine (7.2 µL, 0.052 mmol) was added. At thirty minutes, anhydrous acetonitrile (0.5 mL) and anhydrous methanol (0.3 mL) were added. At two hours total reaction time, the product was precipitated by slow addition of anhydrous IPA containing 0.25% phosphoric acid. The product was washed with anhydrous IPA and then washed with diethyl ether. Residual solvent was evaporated at reduced pressure. Yield: 58 mg (58%) yellow powder. HPLC analysis employed a C18 column using an acetonitrile gradient with 0.1% TFA; retention times were des-ethyl sunitinib 2.5 mM and product 10.7 minutes with 41% purity at 320 nm. Buffer hydrolysis was done to monitor the release of desethyl sunitinib (100 mM phosphate, 37° C.): 11 d at pH 7.5, 1.7 d at pH 8.5.

Example 10

Synthesis of 4-Arm-PEG-Ala-Des-ethyl Sunitinib (Compound 14)

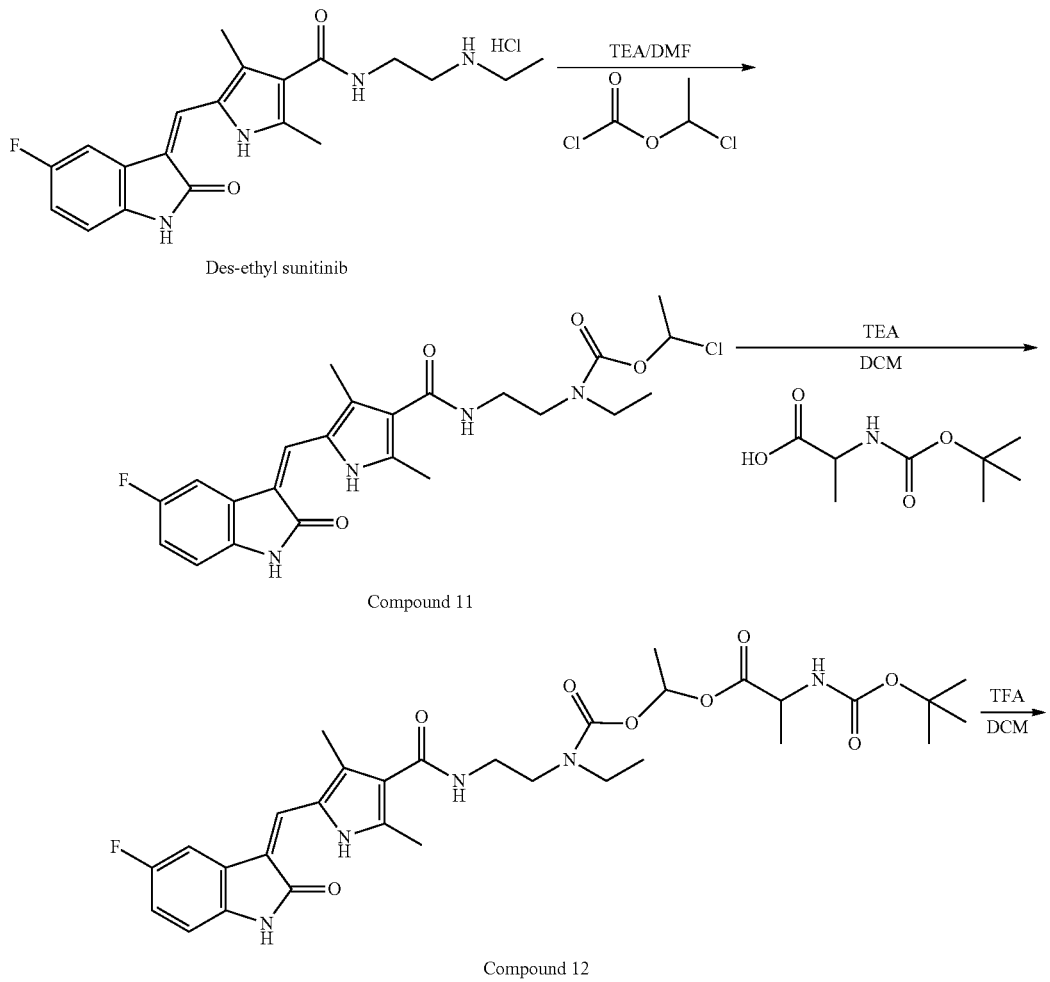

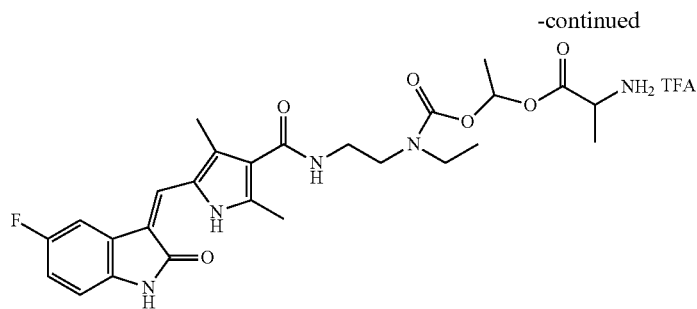
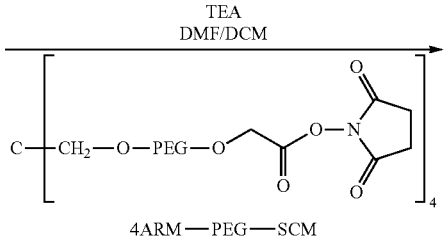

Compound 13

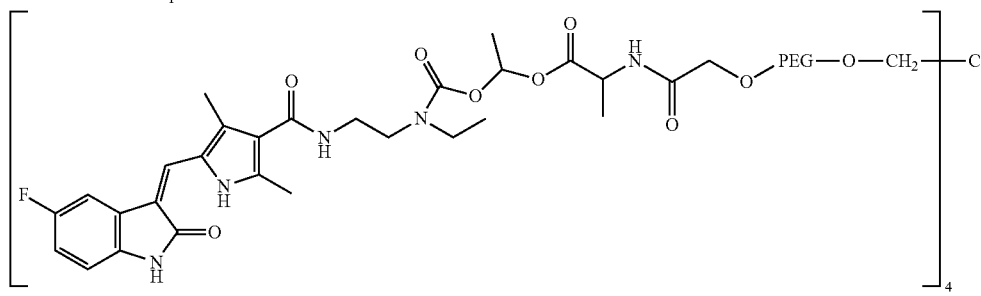

Compound 14

Synthesis of (Z)-1-chloroethyl ethyl(2-(5-((5-fluoro-2-oxoindolin-3-ylidene)methyl)-2,4-dimethyl-1H-pyrrole-3-carboxamido)ethyl)carbamate (Compound 11)

In a round bottom flask, Des-ethyl sunitinib hydrochloride (1.5 g; 0.00369 mol) was dissolved in DMF (150 ml). Next, triethylamine (TEA; 1.54 ml; 0.01106 mol) was added and the mixture was cooled on the ice bath. 1-Chloroethyl chloroformate (0.803 ml; 0.00737 mol) dissolved in 20 ml of anhydrous THF was added slowly at 0-5° C. The mixture was stirred for sixty minutes at room temperature, and then the solvents were distilled off to dryness under reduced pressure at 60° C. The crude product was dissolved in dichloromethane (500 ml) and washed with 0.1 M $NaH_2PO_4$ (150 ml×2) and saturated solution of NaCl (150 ml). The solution was dried with anhydrous $MgSO_4$, filtered and the solvent was distilled off to dryness under reduced pressure. The purity of the product (Compound 11) determined by RP HPLC was 87%.

Synthesis of (Z)-1-(ethyl(2-(5-((5-fluoro-2-oxoindolin-3-ylidene)methyl)-2,4-dimethyl-1H-pyrrole-3-carboxamido)ethyl)carbamoyloxy)ethyl 2-(tert-butoxycarbonylamino)propanoate (Compound 12)

In a round bottom flask, Compound 11 (1.76 g; 0.00369 mol) was dissolved in the mixture of DMF (10 ml) and anhydrous dichloromethane (20 ml). t-Boc-alanine (3.49 g; 0.01845 mol) was added followed by TEA (1.54 ml; 0.01107 mol). The mixture was stirred for two days at room temperature under nitrogen atmosphere. The solvents were distilled off at 55° C. under reduced pressure. The residue was dissolved in dichloromethane (500 ml) and washed with 0.1 M $NaH_2PO_4$ (100 ml×5). The solution was dried with anhydrous $MgSO_4$, filtered and the solvent was distilled off under reduced pressure. The purity of the crude product determined by RP HPLC was 62%. The product was purified by silica gel chromatography using a mixture of dichloromethane-methanol (94:6) as an eluent giving the desired Compound 12 (0.426 g) having 97.3% purity determined by RP HPLC. $^1$H-NMR ($CDCl_3$, 500 MHz): δ (ppm) 8.7 (d, 1H, —NH); 7.32 (s, 1H, —CH); 7.18 (d, 1H, —CH); 6.84 (m, 3H, 3-CH); 6.57 (m, 1H, —NH); 5.04 (d, 1H, —NH); 4.27 (m 1H, —CH); 3.34-3.65 (m 6H, 3-$CH_2$); 2.50 (s, 3H, —$CH_3$); 2.45 (s, 3H, —$CH_3$); 1.53 (d, 3H, —$CH_3$); 1.44-1.33 (m, 12H, 4-$CH_3$); 1.18 (t, 3H, —$CH_3$). Analysis by LC-MS ($[C_{31}H_{40}FN_5O_8]^+$ expected M+H=630. found M+H=630.3).

Synthesis of (Z)-1-(ethyl(2-(5-((5-fluoro-2-oxoindolin-3-ylidene)methyl)-2,4-dimethyl-1H-pyrrole-3-carboxamido)ethyl)carbamoyloxy)ethyl 2-aminopropanoateTFA salt) (Compound 13)

Compound 12 (0.426 g) was dissolved in the mixture of dichloromethane (20 ml) and trifluoroacetic acid (10 ml) and the solution was stirred for one hour at room temperature. The solvents were distilled off under reduced pressure and the wet product was dried under vacuum overnight giving of the desired Compound 13 having 95.9% purity determined by RP HPLC. $^1$H-NMR (DMSO-$d_6$, 500 MHz): δ (ppm) 8.34 (m, 3H, —$NH_2$; —NH); 7.77-7.70 (m, 3H, 2H—NH, 1H—CH); 6.95-6.78 (m, 3H, 3-CH); 4.25 (m, 1H, —CH); 3.39-3.28 (m, 6H, 3-$CH_2$); 2.43 (s 3H, —$CH_3$); 2.41 (s, 3H, —$CH_3$); 1.50-1.44 (m, 3H, —$CH_3$); 1.40-1.32 (m, 3H, —$CH_3$); 1.11-1.07 (m, 3H, —$CH_3$). Analysis by LC-MS ($[C_{26}H_{32}FN_5O_6]$ expected M=529.23. found M=529).

Synthesis of (Z)-1-(ethyl(2-(5-((5-fluoro-2-oxoindolin-3-ylidene)methyl)-2,4-dimethyl-1H-pyrrole-3-carboxamido)ethyl)carbamoyloxy)ethyl 2-(2-(4arm-PEG 20,000)acetamido)propanoate (Compound 14)

In a round bottom flask, Compound 13 (0.322 g; 0.000500 mol) was dissolved in anhydrous DMF (3 ml) then anhydrous dichloromethane (12 ml) was added followed by 4ARM-PEG(20K)-Acetic Acid, Succinimidyl Ester (4ARM-PEG(20K)-SCM; 2.17 g; 0.000109 mol). Next, TEA (0.243 ml; 0.002793 mol) dissolved in dichloromethane (2 ml) was added. The reaction mixture was stirred for three hours at room temperature. Dichloromethane was distilled off under reduced pressure and the product was precipitated with ethyl ether (80 ml). The product was filtered off and dried under vacuum. Next, it was dissolved in dichloromethane (2 ml), precipitated with isopropyl alcohol, and dried under vacuum giving 2.08 g of solid product. NMR analysis confirmed the structure of the desired compound and also showed that 88.5% of 4ARM-PEG end groups were substituted with desethyl sunitinib. $^1$H-NMR (CDCl$_3$, 500 MHz): δ (ppm) 8.3 (d, 4H, —NH); 7.43 (s, 4H, —CH); 7.22 (d, 4H, —CH); 6.85 (m, 12H, 3-CH); 6.54 (m, 4H, —NH); 4.54-4.35 (m, 4H, —CH); 3.85-3.49 (m, PEG); 2.57 (s, 12H, —CH$_3$); 2.49 (s, 12H, —CH$_3$); 1.53 (d, 12H, —CH$_3$); 1.44-1.29 (m, 12H, —CH$_3$); 1.16 (t, 12H, —CH$_3$).

Example 11

Synthesis of 4-Arm-PEG-Gly-Des-ethyl Sunitinib (Compound 15)

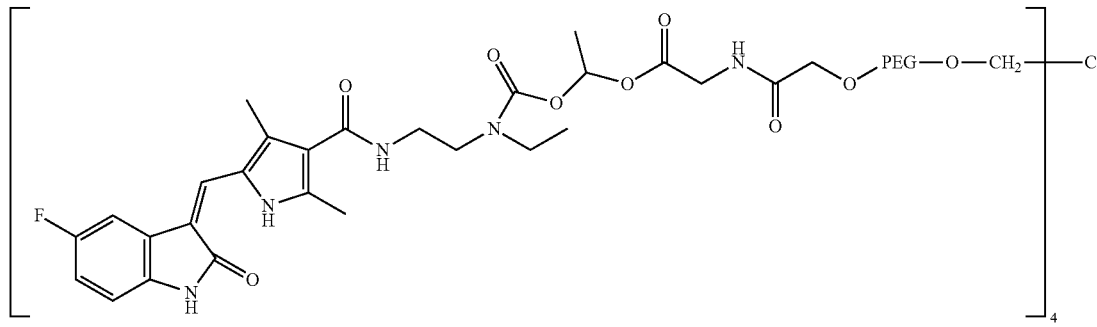

Synthesis of (Z)-1-(ethyl(2-(5-((5-fluoro-2-oxoindolin-3-ylidene)methyl)-2,4-dimethyl-1H-pyrrole-3-carboxamido)ethyl)carbamoyloxy)ethyl 2-(2-(4arm-PEG 20,000)acetamido)acetate (Compound 15)

4ARM-PEG-Gly-Des-ethyl sunitinib was performed in a manner similar to the approach used in Example 10 except t-Boc-glycine was used in place of t-Boc-alanine. NMR analysis confirmed the structure of the desired compound and also showed that 95.2% of 4-arm-PEG end groups were substituted with des-ethyl sunitinib.

Example 12

Synthesis of 4-Arm-PEG-Leu-Des-ethyl Sunitinib (Compound 16)

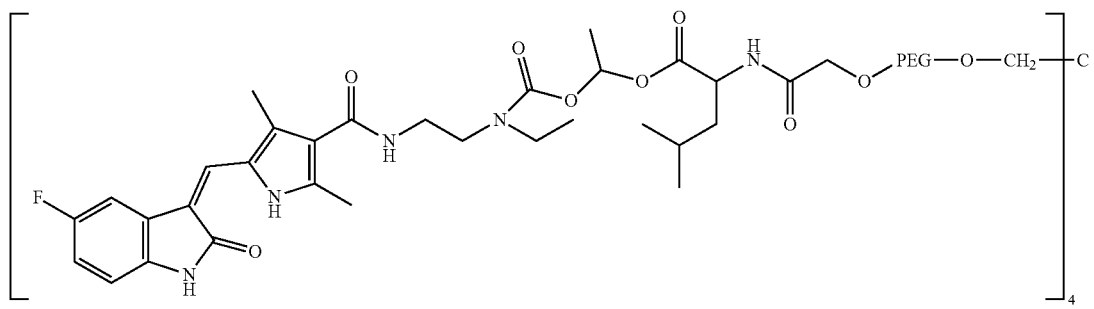

Synthesis of (Z)-1-(ethyl(2-(5-(((5-fluoro-2-oxoindo-lin-3-ylidene)methyl)-2,4-dimethyl-1H-pyrrole-3-carboxamido)ethyl)carbamoyloxy)ethyl 2-((4arm-PEG 20,000)carbonylamino)-4-methylpentanoate (Compound 16)

4-arm-PEG-Leu-Des-ethyl sunitinib was prepared in a manner similar to the approach used in Example 10 except t-Boc-leucine was used in place of t-Boc-alanine. NMR analysis confirmed the structure of the desired compound and also showed that 78.3% of 4-arm-PEG end groups were substituted with des-ethyl sunitinib.

What is claimed is:
1. A compound of Formula I-C, multi-arm:

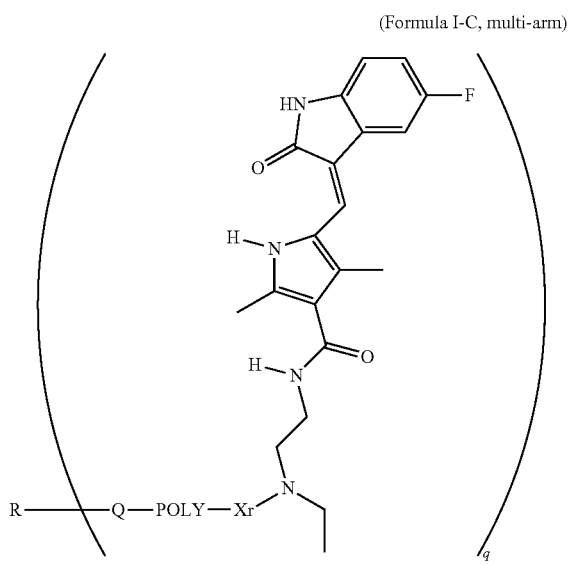

(Formula I-C, multi-arm)

wherein:
  Xr is a releasable linkage-containing spacer moiety;
  POLY is a poly(ethylene oxide);
  R, when taken with Q, is a residue of polyol, polythiol, or polyamine bearing from 3 to about 50 hydroxyl, thiol or amino groups, respectively;
  each Q is a linker selected from O, S, and NH; and
  q is a positive integer from 3 to about 50;
  or a pharmaceutically acceptable salt thereof.

2. The compound of claim 1, wherein Xr comprises a thioether, carbamate, ester, carbonate, urea, or enzyme-cleavable peptidic linkage.

3. The compound of claim 1, wherein Xr is according to Formula III:

(Formula III)

wherein:
  a is zero or one;
  b is zero or one;
  $X^1$, when present, is a first spacer;
  Lr is a releasable linkage; and
  $X^2$, when present, is a second spacer.

4. A compound of claim 1, wherein Xr comprises a structure selected from the group consisting of ~C(O)O—,

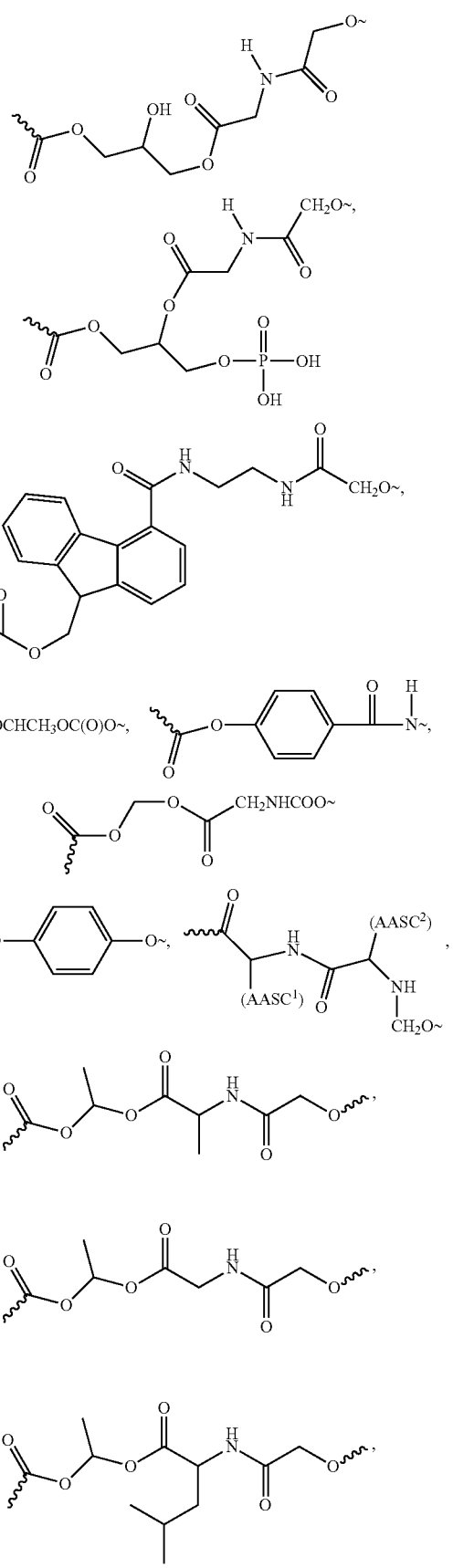

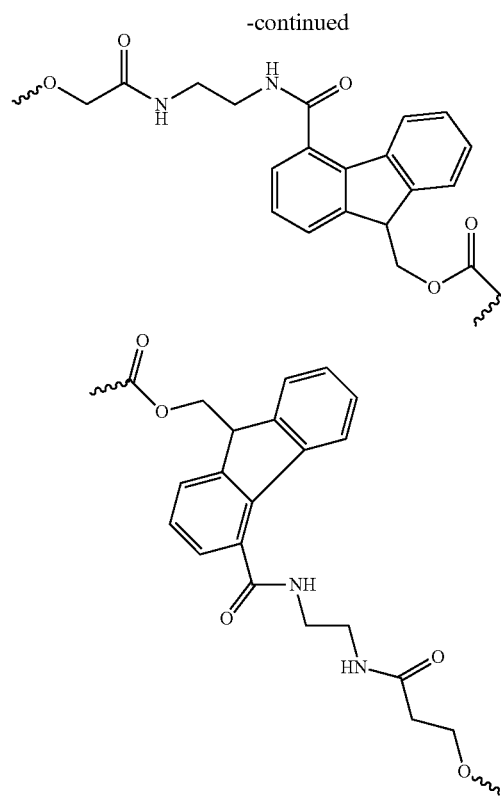

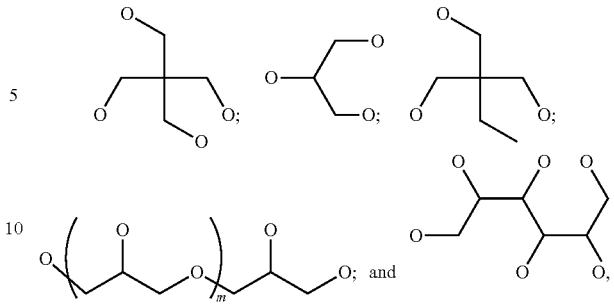

wherein m is a positive integer from 0-40.

11. The compound of claim 1, wherein q is 3.
12. The compound of claim 1, wherein q is 4.
13. The compound of claim 1, wherein q is 5.
14. The compound of claim 1, wherein q is 6.
15. The compound of claim 1, wherein q is 7.
16. The compound of claim 1, wherein q is 9.
17. The compound of claim 1, wherein q is 10.
18. A compound of claim 1, wherein the compound is selected from the group consisting of
   (Z)-1-(ethyl(2-(5-((5-fluoro-2-oxoindolin-3-ylidene)methyl)-2,4-dimethyl-1H-pyrrole-3-carboxamido)ethyl)carbamoyloxy)ethyl 2-(2-(4armPEG 20,000)acetamido)propanoate (Compound 14);
   (Z)-1-(ethyl(2-(5-((5-fluoro-2-oxoindolin-3-ylidene)methyl)-2,4-dimethyl-1H-pyrrole-3-carboxamido)ethyl)carbamoyloxy)ethyl 2-(2-(4armPEG 20,000)acetamido)acetate (Compound 15); and
   (Z)-1-(ethyl(2-(5-((5-fluoro-2-oxoindolin-3-ylidene)methyl)-2,4-dimethyl-1H-pyrrole-3-carboxamido)ethyl)carbamoyloxy)ethyl 2-((4armPEG 20,000)carbonylamino)-4-methylpentanoate (Compound 16).
19. A composition comprising:
   (i) a compound of claim 1; and
   (ii) a pharmaceutically acceptable excipient.
20. A dosage form comprising the composition of claim 19.
21. A method of treating a subject having a condition that is mediated by abnormal protein kinase activity, the method comprising administering to the subject, a therapeutically effective amount of a compound of claim 1.

wherein $AASC^1$ is a first amino acid side chain; $AASC^2$ is a second amino acid side chain; and $AASC^1$ and $AASC^2$ are selected such that the compound includes an enzymatically cleavable linkage.

5. The compound of claim 1, wherein each POLY has a molecular weight of less than 2000 Daltons.
6. The compound of claim 1, wherein each POLY has from about 1 to about 30 monomers.
7. The compound of claim 1, wherein each POLY has from about 1 to about 10 monomers.
8. The compound of claim 1, wherein each POLY has a molecular weight of from 2000 Daltons to about 150,000 Daltons.
9. The compound of claim 1, wherein each POLY includes an alkoxy or hydroxy end-capping moiety.
10. The compound of claim 1, wherein Q is oxygen and wherein R, when taken with Q, has a structure selected from:

* * * * *